US007270827B2

(12) United States Patent
Reddish et al.

(10) Patent No.: US 7,270,827 B2
(45) Date of Patent: Sep. 18, 2007

(54) MULTIVALENT STREPTOCOCCAL VACCINE COMPOSITIONS AND METHODS FOR USE

(75) Inventors: Mark A. Reddish, Woodinville, WA (US); Mary ChaoHong Hu, Edmonds, WA (US); Michael A. Walls, Kenmore, WA (US); James B. Dale, Memphis, TN (US)

(73) Assignees: University of Tennessee Research Foundation, Knoxville, TN (US); ID Biomedical Corporation of Washington, Bothell, WA (US)

( * ) Notice: Subject to any disclaimer, the term of this patent is extended or adjusted under 35 U.S.C. 154(b) by 666 days.

(21) Appl. No.: 10/284,400

(22) Filed: Oct. 28, 2002

(65) Prior Publication Data

US 2003/0143245 A1 Jul. 31, 2003

Related U.S. Application Data

(60) Provisional application No. 60/348,434, filed on Oct. 26, 2001.

(51) Int. Cl.
*A61K 39/09* (2006.01)
*A61K 39/02* (2006.01)
*A61K 39/116* (2006.01)
*A61K 39/00* (2006.01)
*A61K 38/00* (2006.01)
*C07K 1/00* (2006.01)
*C07K 2/00* (2006.01)

(52) U.S. Cl. ............... 424/244.1; 424/234.1; 424/192.1; 424/203.1; 424/190.1; 424/184.1; 514/2; 530/350; 530/300; 530/825; 530/806

(58) Field of Classification Search ............ 424/244.1, 424/234.1, 192.1, 184.1, 190.1, 203.1, 237.1; 514/2; 530/350, 300, 825, 806
See application file for complete search history.

(56) References Cited

U.S. PATENT DOCUMENTS

| 4,284,537 A | 8/1981 | Beachey ............... 260/6 |
|---|---|---|
| 4,399,216 A | 8/1983 | Axel et al. ............ 435/6 |
| 4,411,993 A | 10/1983 | Gillis ................. 435/68 |
| 4,454,121 A | 6/1984 | Beachey ............... 424/177 |
| 4,460,575 A | 7/1984 | d'Hinterland et al. ..... 424/92 |
| 4,521,334 A | 6/1985 | Beachey ............ 260/112.5 R |
| 4,543,439 A | 9/1985 | Frackelton, Jr. et al. ..... 935/92 |
| RE32,011 E | 10/1985 | Zimmerman et al. ... 260/112 B |
| 4,579,821 A | 4/1986 | Palmiter et al. ........ 435/172.3 |
| 4,597,967 A | 7/1986 | Beachey ............... 424/88 |
| 4,704,362 A | 11/1987 | Itakura et al. ........... 435/253 |
| 4,705,684 A | 11/1987 | Beachey ............... 424/88 |
| 4,766,075 A | 8/1988 | Goeddel et al. ........ 435/240.2 |
| 4,784,948 A | 11/1988 | Scott et al. ............ 435/68 |
| 4,784,950 A | 11/1988 | Hagen et al. ........... 435/68 |
| 4,801,542 A | 1/1989 | Murray et al. ........ 435/172.3 |
| 4,902,614 A | 2/1990 | Wakabayashi et al. ...... 435/7 |
| 4,919,930 A | 4/1990 | Beachey et al. .......... 424/88 |
| 4,935,349 A | 6/1990 | McKnight et al. ........ 435/69.5 |
| 4,987,071 A | 1/1991 | Cech et al. ............ 435/91 |
| 5,124,153 A | 6/1992 | Beachey et al. ........ 424/93 P |
| 5,132,405 A | 7/1992 | Huston et al. ......... 530/387.3 |
| 5,162,226 A | 11/1992 | Beachey et al. ........ 435/252.3 |
| 5,219,740 A | 6/1993 | Miller et al. ........... 435/69.6 |
| 5,254,678 A | 10/1993 | Haseloff et al. ......... 536/23.2 |
| 5,334,379 A | 8/1994 | Pillai et al. ............ 424/85.2 |
| 5,359,051 A | 10/1994 | Cook et al. ............ 536/26.7 |
| 5,443,439 A | 8/1995 | Ohshita ................ 601/90 |
| 5,580,563 A | 12/1996 | Tam .................. 424/197.11 |
| 5,686,272 A | 11/1997 | Marshall et al. ......... 435/91.2 |
| 5,726,292 A | 3/1998 | Lowell ................ 530/403 |
| 5,985,284 A | 11/1999 | Lowell ................ 424/234.1 |
| 5,985,654 A | 11/1999 | Fischetti et al. ........ 435/320.1 |
| 6,063,386 A | 5/2000 | Dale et al. ............ 424/244.1 |
| 6,419,932 B1 | 7/2002 | Dale .................. 424/244.1 |
| 6,716,433 B1 * | 4/2004 | Dale .................. 424/244.1 |
| 7,063,850 B1 * | 6/2006 | Dale .................. 424/190.1 |
| 7,074,416 B2 * | 7/2006 | Dale .................. 424/244.1 |
| 2002/0176863 A1 | 11/2002 | Dale .................. 424/184.1 |

FOREIGN PATENT DOCUMENTS

| EP | 612 844 A2 | 8/1994 |
|---|---|---|
| EP | 305279 B1 | 3/1995 |

(Continued)

OTHER PUBLICATIONS

Alan L. Bisno, "The Concept of Rheumatogenic and Nonrheumatogenic Group A Streptococci," in *Streptococcal Diseases and the Immune Response*, New York: Academic Press, 1980, pp. 789-803.

(Continued)

*Primary Examiner*—S. Devi
(74) *Attorney, Agent, or Firm*—Seed IP Law Group PLLC

(57) ABSTRACT

Compositions and methods for making and using therapeutic formulations of multivalent hybrid polypeptides comprising immunogenic peptides of M proteins from various different serotypes of group A streptococci and antibodies thereto are provided. Also provided are nucleic acids encoding such hybrid polypeptides. The hybrid polypeptide formulations may be used, for example, in methods for treating or preventing a microbial infection and eliciting a protective immune response having broadly protective opsonic antibodies in the absence of tissue cross-reactive antibodies.

15 Claims, 22 Drawing Sheets

FOREIGN PATENT DOCUMENTS

| | | |
|---|---|---|
| EP | 360 257 B1 | 11/1996 |
| EP | 618813 B1 | 1/2002 |
| EP | 625043 B1 | 3/2002 |
| EP | 415 731 B1 | 4/2003 |
| WO | WO90/07936 | 7/1990 |
| WO | WO91/02805 | 3/1991 |
| WO | WO92/06693 | 4/1992 |
| WO | WO93/10218 | 5/1993 |
| WO | WO93/11230 | 6/1993 |
| WO | WO93/25234 | 12/1993 |
| WO | WO93/25698 | 12/1993 |
| WO | WO94/03622 | 2/1994 |
| WO | WO94/06421 | 3/1994 |
| WO | WO94/06465 | 3/1994 |
| WO | WO94/26914 | 11/1994 |
| WO | WO95/10607 | 4/1995 |
| WO | WO98/01561 | 1/1998 |
| WO | WO99/13084 | 3/1999 |
| WO | WO 00/37648 | 6/2000 |

OTHER PUBLICATIONS

Beachey and Seyer, "Protective and nonprotective epitopes of chemically synthesized peptides of the NH$_2$-terminal region of type 6 streptococcal M protein," *Journal of Immunology* 136(6): 2287-2292, Mar. 15, 1986.

Beachey, E. et al., "Human Immune Response to Immunization with a Structurally Defined Polypeptide Fragment of Streptococcal M Protein," *Journal of Experimental Medicine* 150: 862-877, Oct. 1979.

Beachey, E.H. et al., "Primary Structure of Protective Antigens of Type 24 Streptococcal M Protein," *The Journal of Biological Chemistry* 255(13): 6284-6289, Jul. 10, 1980.

Beachey, E.H. et al., "Protective Immunogenicity and T Lymphocyte Specificity of a Trivalent Hybrid Peptide Containing NH$_2$-Terminal Sequences of Types 5, 6, and 24 M Proteins Synthesized in Tandem," *Journal of Experimental Medicine* 166: 647-656, Sep. 1987.

Beachey, E.H. et al., "Purification and Properties of M Protein Extracted From Group A Streptococci With Pepsin: Covalent Structure of the Amino Terminal Region of Type 24 M Antigen," *Journal of Experimental Medicine* 145: 1469-1483, 1977.

Beachey, E.H. et al., "Repeating Covalent Structure and Protective Immunogenicity of Native and Synthetic Polypeptide Fragments of Type 24 Streptococcal M Protein," *The Journal of Biological Chemistry* 258(21):13250-13257, Nov. 10, 1983.

Beachey, E.H. et al., "Type-specific protective immunity evoked by synthetic peptide of *Streptococcus pyogenes* M protein," *Nature* 292: 457-459, Jul. 30, 1981.

Beall, B. et al., "Survey of *emm* Gene Sequences and T-Antigen Types from Systemic *Streptococcus pyogenes* Infection Isolates Collected in San Francisco, California; Atlanta, Georgia; and Connecticut in 1994 and 1995," *Journal of Clinical Microbiology* 35(5): 1231-1235, May 1997.

Boyle, M.D. et al., "Role of *emm* and *mrp* genes in the virulence of group A streptococcal isolate 64/14 in a mouse model of skin infection," *J. Infect. Dis.* 177(4): 991-997, Apr. 1998.

Bronze, M.S. et al., "Protective and Heart-Cross Reactive Epitopes Located Within the NH$_2$ Terminus of Type of 19 Streptococcal M Protein," *Journal of Experimental Medicine* 167: 1849-1859, Jun. 1988.

Bronze, M.S. et al., "Protective and heart-cross-reactive epitopes of type 19 streptococcal M protein," *Trans. Assoc. Am. Physicians* 100: 80-84, 1987.

Clements and El-Morshidy, "Construction of a potential live oral bivalent vaccine for typhoid fever and cholera-*Escherichia coli*-related diarrheas," *Infect. Immun.* 46(2): 564-569, Nov. 1984.

Clements, J.D., "Construction of a Nontoxic Fusion Peptide for Immunization against *Escherichia coli* Strains That Produce Heat-Labile and Heat-Stable Enterotoxins," *Infect. Immun.* 58(5): 1159-1166, May 1990.

Cunningham M.W. et al., Peptic Digestion of Streptococcal M Protein. I. Effect of Digestion at Suboptimal pH upon the Biological and Immunochemical Purified M Protein Extracts, *Infection and Immunity* 9(2): 244-248, Feb. 1974.

Cunningham, M.W., "Pathogenesis of Group A Streptococcal Infections," *Clinical Microbiology Reviews* 13(3): 470-511, Jul. 2000.

Dale and Beachey, "Epitopes of Streptococcal M Proteins Shared with Cardiac Myosin," *Journal of Experimental Medicine* 162: 583-591, Aug. 1985.

Dale and Beachey, "Localization of Protective Epitopes of the Amino Terminus of Type 5 Streptococcal M Protein," *Journal of Experimental Medicine* 163: 1191-1202, May 1986.

Dale and Beachey, "Multiple, Heart-Cross-Reactive Epitopes of Streptococcal M Proteins," *Journal of Experimental Medicine* 161: 113-122, Jan. 1985.

Dale and Beachey, "Sequence of Myosin-Crossreactive Epitopes of Streptococcal M Protein," *Journal of Experimental Medicine* 164: 1785-1790, Nov. 1986.

Dale, J.B. et al. "Heterogeneity of type-specific and cross-reactive antigenic determinants within a single M protein of group A streptococci," *Journal of Experimental Medicine* 151: 1026-1038, 1980.

Dale, J.B. et al., "New protective antigen of group A streptococci," *Journal of Clinical Investigation* 103(9): 1261-1268, May 1999.

Dale, J.B. et al., "Protective Antigenic Determinant of Streptococcal M Protein Shared with Sarcolemmal Membrane Protein of Human Heart," *Journal of Experimental Medicine* 156(4): 1165-1176, Oct. 1982.

Dale, J.B. et al., "Recombinant Tetravalent Group A Streptococcal M Protein Vaccine," *Journal of Immunology* 151(4): 2188-2194, Aug. 15, 1993.

Dale, J.B. et al., "Recombinant, octavalent group A streptococcal M protein vaccine," *Vaccine* 14(10): 944-948, Jul. 1996.

Dale, J.B. et al., "Type-specific immunogenicity of a chemically synthesized peptide fragment of type 5 streptococcal M protein," *Journal of Experimental Medicine* 158: 1727-1732, Nov. 1983.

Dale, J.B., "Multivalent group A streptococcal vaccine designed to optimize the immunogenicity of six tandem M protein fragments," *Vaccine* 17:193-200, 1999.

Dochez, A.R. et al., "Studies on the Biology of Streptococcus. I. Antigenic Relationships Between Strains of Streptococcus Haemolyticus," *Journal of Experimental Medicine* 30: 179-213, 1919.

Fischetti, V.A. et al., "Streptococcal M6 Protein Expressed in *Escherichia coli*. Localization, Purification, and Comparison with Streptococcal-derived M Protein," *Journal of Experimental Medicine* 159(4): 1083-1095, Apr. 1984.

Fischetti, V.A. et al., "Surface Proteins from Gram-Positive Cocci Share Unique Structural Features," in *New Perspectives on Streptococci and Streptococcal Infections*, G. Orefici (Ed.), Gustav Fischer, New York, 1992, pp. 165-167.

Fischetti, V.A., "Streptococcal M Protein," *Scientific American* 264(6): 58-65, Jun. 1991.

Goroney-Bermes, P. et al., "Monoclonal antibody to human renal glomeruli cross-reacts with streptococcal M protein," *Infect. Immun.* 55(10): 2416-2419, Oct. 1987.

Haas, J. et al., "Codon usage limitation in the expression of HIV-1 envelope glycoprotein," *Current Biology* 6(3): 315-324, Mar. 1, 1996.

Jones, K.F. et al., "The Importance of the Location of Antibody Binding on the M6 Protein for Opsonization and Phagocytosis of Group A M6 Streptococci," *Journal of Experimental Medicine* 167(3): 1114-1123, Mar. 1, 1988.

Kraus and Beachey, "Renal autoimmune epitope of group A streptococci specified by M protein tetrapeptide Ile-Arg-Leu-Arg," *Proc. Natl. Acad. Sci. USA* 85(12): 4516-4520, Jun. 1988.

Kraus, W. et al., "Sequence and Type-Specific Immunogenicity of the Amino-Terminal Region of Type 1 Streptococcal M Protein," *Journal of Immunology* 139(9): 3084-3090, Nov. 1, 1987.

Lancefield, R.C., "Current Knowlege of Type-specific M Antigens of Group A Streptococci," *Journal of Immunology* 89(3): 307-313, Sep. 1962.

Lancefield, R.C., "Differentiation of Group A Streptococci With a Common R Antigen Into Three Serological Types, With Special Reference to the Bactericidal Test," *J. Exp. Med. 106*: 525-544, 1957.

Lancefield, R.C., "The Antigenic Complex of Streptococcus Haemolyticus. I. Demonstration of a Type-Specific Substance in Extracts of Streptococcus Haemolyticus," *Journal of Experimental Medicine 47*: 91-103, 1928.

McLellan, D.G. et al., "Spa Contributes to the Virulence of Type 18 Group A Streptococci," *Infection and Immunity 69*(5): 2943-2949, May 2001.

Miller, L. et al., "Antigenic Variation among Group A Streptococcal M Proteins. Nucleotide Sequence of the Serotype 5 M Protein Gene and Its Relationship with Gene Encoding Types 6 and 24 M Proteins," *The Journal of Biological Chemistry 263*(12): 5668-5673, Apr. 25, 1988.

Mouw, A.R. et al., "Molecular Evolution of Streptococcal M Protein: Cloning and Nucleotide Sequence of the Type 24 M Protein Gene and Relation to Other Genes of *Streptococcus pyogenes*," *Journal of Bacteriology 170*(2): 676-684, Feb. 1988.

Müller, K.M. et al., "Model and Simulation of Multivalent Binding to Fixed Ligands," *Analytical Biochemistry 261*:149-158, 1998.

Podbielski, A. et al., "A group A streptococcal Enn protein potentially resulting from intergenomic recombination exhibits atypical immunoglobulin-binding characteristics," *Mol. Microbiol. 12*(5): 725-736, 1994.

Podbielski, A. et al., "Application of the polymerase chain reaction to study the M protein(-like) gene family in beta-hemolytic streptococci," *Med. Microbiol Immunol. 180*: 213-227, 1991.

Poirier, T.P. et al., "Protective Immunity Evoked By Oral Administration of Attenuated *aroA Salmonella typhimurium* Expressing Cloned Streptococcal M Protein," *Journal of Experimental Medicine 168*(1): 25-32, Jul. 1, 1988.

Polly, S.M. et al., "Protective studies with a group A streptococcal M protein vaccine. II. Challenge of volunteers after local immunization in the upper respiratory tract," *J. Infect. Dis. 131*(3): 217-224, Mar. 1975.

Sargent, S.J. et al., "Sequence of Protective Epitopes of Streptococcal M Proteins Shared with Cardiac Sarcolemmal Memebranes," *Journal of Immunology 139*(4): 1285-1290, Aug. 15, 1987.

Schuchat, A. et al., "Active Bacterial Core Surveillance of the Emerging Infections Program Network," *Emerging Infectious Diseases 7*(1): 92-99, Jan.-Feb. 2001.

Whatmore and Kehoe, "Horizontal gene transfer in the evolution of group A streptococcal *emm*-like genes: Gene mosaics and variation in Vir regulons," *Molecular Microbiology 11*(2): 363-374, Jan. 1994.

Yang, T.-T. et al., "Optimized codon usage and chromophore mutations provide enhanced sensitivity with green fluorescent protein," *Nucleic Acids Research 24*(22): 4592-4594, 1996.

Zabriskie, J.B. et al., "Heart-reactive antibody associated with rheumatic fever: characterization and diagnostic significance," *Clinical and Experimental Immunology 7*(2): 147-159, Aug. 1970.

Dale, J.B., "New Protective Antigen of Group A Streptococci," U.S. Appl. No. 09/471,817, filed Dec. 22, 1999.

Dale, J.B., "Group A Streptococcal Vaccines," U.S. Appl. No. 09/151,409, filed Sep. 10, 1998.

Alber and Kawasaki, "Nucleotide Sequence of the Triose Phosphate Isomerase Gene of *Saccharomyces cerevisiae*," *Journal of Molecular and Applied Genetics 1*: 419-434,1982.

Altschul, S., "Amino Acid Substitution Matrices from an Information Theoretic Perspective," *J. Mol. Biol. 219*: 555-565, 1991.

Ammerer, G., *Methods in Enzymology*, vol. 101, Academic Press, Inc., New York, Wu et al. (eds.), 1983, Chapeter 11, "Expression of Genes in Yeast Using the ADCI Promoter," pp. 193-201.

Atkinson et al., "Baculoviruses as Vectors for Foreign Gene Expression in Insect Cells," *Pestic. Sci. 28*: 215-224, 1990.

Beggs, J., "Transformation of yeast by a replicating hybrid plasmid," *Nature 275*: 104-108, Sep. 14, 1978.

Beggs et al., "Characterization of *Mycobacterium tuberculosis* Complex Direct Repeat Sequence for Use in Cycling Probe Reaction," *Journal of Clinical Microbiology 34*(12): 2985-2989, Dec. 1996.

Bekkaoui et al., "Cycling Probe Technology with Rnase H Attached to an Oligonucleotide," *BioTechniques 20*(2): 240-248, Feb. 1996.

Bergman et al., "Two regulatory elements for immunoglobulin k light chain gene expression," *Proc. Natl. Acad. Sci. USA 81*: 7041-7045, Nov. 1984.

Bird et al., "Single-Chain Antigen-Binding Proteins," *Science 242*: 423-426, Oct. 21, 1988.

Bolivar et al., "Construction And Characterization Of New Cloning Vehicles II. A Multipurpose Cloning System," *Gene 2*: 95-113, 1977.

Boshart et al., "A Very Strong Enhancer Is Located Upstream of an Immediate Early Gene of Human Cytomegalovirus," *Cell 41*: 521-530, Jun. 1985.

Botstein et al., "Sterile Host Yeasts (SHY): A Eukaryotic System Of Biological Containment For Recombinant DNA Experiments,"0 *Gene 8*: 17-24, 1979.

Bowie, J.U. et al., "Deciphering the Message in Protein Sequences: Tolerance to Amino Acid Substitutions," *Science 247*: 1306-1310, Mar. 16, 1990.

Broach et al., "Tranformation In Yeast: Development Of a Hybrid Cloning Vector And Isolation Of The *CAN1* Gene," *Gene 8*: 121-133, 1979.

Burgess, W.H. et al., "Posssible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," *J. Cell. Biol. 111*: 2129-2138, 1990.

Chadwick et al., "A sensitive and robust method for measles RNA detection," *Journal of Virological Methods 70*: 59-70, 1998.

Chang et al., "Phenotypic expression in *E. coli* of a DNA sequence coding for mouse dihydrofolate reductase," *Nature 275*: 617-624, Oct. 19, 1978.

Chappell and Stuart, "Demonstration of protection in mice from a lethal challenge of three M serotypes of *Streptococcus pyogenes* using an M-negative vaccine," *Vaccine 11*(6): 643-648, 1993.

Chaudhary et al., "A recombinant immunotoxin consisting of two antibody variable domains fused to *Pseudomonas exotoxin*," *Nature 339*: 394-397, Jun. 1, 1989.

Cook and Self, *Monoclonal Antibodies: Production, Engineering, and Clinical Application*, Ritter and Ladyman (eds.), Cambridge University Press, 1995, Chapter 9, "Monoclonal antibodies in diagnostic immunoassays," pp. 180-208.

Czakó and Márton, "The Herpes Simplex Virus Thymidine Kinase Gene as a Conditional Negative-Selection Marker Gene in *Arabidopsis thaliana*," *Plant Physiol. 104*: 1067-1071, 1994.

DeNoto et al., "Human growth hormone DNA sequence and mRNA structure: possible alternative splicing," *Nucleic Acids Research 9*(15): 3719-3730, 1981.

Dyer et al., "Quantitation of human immunodeficiency virus type 1 RNA in cell free seminal plasma: comparison of NASBA™ with Amplicor™ reverse transcription-PCR amplification and correlation with quantitative culture," *Journal of Virological Methods 60*: 161-170, 1996.

Ehricht et al., "Cooperative amplification of templates by cross-hybridization (CATCH)," *Eur. J. Biochem. 243*: 358-364, 1997.

Elvin et al., "Modified basteriophage lambda promoter vectors for overproduction of proteins in *Escherichia coli*," *Gene 87*: 123-126, 1990.

Graham et al., "Characteristics of a Human Cell Line Transformed by DNA from Human Adenovirus Type 5," *J. Gen. Virol. 36*: 59-72, 1977.

Grant et al., "Improved RNA sequencing method to determine immunoglobulin mRNA sequence," *Nucleic Acids Research 15*(13): 5496, 1987.

Henikoff and Henikoff, "Amino acid substitution matrices from protein blocks," *Proc. Natl. Acad. Sci. USA 89*: 10915-10919, Nov. 1992.

Hinnen et al., "Tranformation of yeast," *Proc. Natl. Acad. Sci. USA 75*(4): 1929-1933, Apr. 1978.

Hitzeman et al., "Isolation and Characterization of the Yeast 3-Phosphoglycerokinase Gene (PGK) by an Immunological Screening Technique," *The Journal of Biological Chemistry 255*(24): 12073-12080, Dec. 25, 1980.

Koering et al., "Induced Expression of the Conditionally Cytotoxic Herpes Simplex Virus *thymidine kinase* Gene by Means of a Parvoviral Regulatory Circuit," *Human Gene Therapy 5*: 457-463, 1994.

Larrick et al., "Polymerase Chain Reaction Using Mixed Primers: Cloning Of Human Monoclonal Antibody Variable Region Genes From Single Hybridoma Cells," *BioTechnology 7*: 934-938, Sep. 1989.

Lazar, E. et al., "Transforming Growth Factor α: Mutation of Aspartic Acid 47 and Leucine 48 Results in Different Biological Activities," *Molecular and Cellular Biology 8*(3): 1247-1252, Mar. 1988.

Loh et al., "Molecular Basis of a Mouse Strain-Specific Anti-Hapten Response," *Cell 33*: 85-93, May 1983.

McGuinness, B.T. et al., "Point mutation in meningococcal *por A* gene associated with increased endemic disease," *The Lancet 337*: 514-517, Mar. 2, 1991.

McGuinness, B.T. et al., "Class 1 outer membrane protein of *Neisseria meningitidis*: epitope analysis of the antigenic diversity between stains, implications for subtype definition and molecular epidemiology," *Molecular Microbiology 7*(4): 505-514, 1993.

McKnight et al., "Identification and molecular analysis of a third *Aspergillus nidulans* alcohol dehydrogenase gene," *The EMBO Journal 4*(8): 2093-2099, 1985.

Meehan et al., "Affinity purification and characterization of a fibrinogen-binding protein complex which protects mice against lethal challenge with *Streptococcus equi* subsp. equi," *Microbiology 144*: 993-1003, 1998.

Messing, J., *Methods in Enzymology*, vol. 101, Wu et al. (eds.), Academic Press, Inc., 1983, vol. 101, "New M13 Vectors for Cloning," pp. 20-79.

Nichols and Yanofsky, *Methods in Enzymology*, vol. 101, Wu et al. (eds.), Academic Press, Inc., 1983, "Plasmids Containing the *trp* Promoters of *Escherichia coli* and *Serratia marcescens* and Their Use in Expressing Cloned Genes," pp. 155-164.

Ohno et al., "Gene Therapy for Vascular Smooth Muscle Cell Proliferation After Arterial Injury," *Science 265*: 781-784, Aug. 5, 1994.

Ørskov and Nielsen, "Truncated glucagon-like peptide-1 (proglucagon 78-107 amide), an intestinal insulin-releasing peptide, has specific receptors on rat insulinoma cells (RIN 5 AH)," *FEBS Letters 229*(1): 175-178, Feb. 1988.

Perry, M.J., *Monoclonal Antibodies: Principles and Applications*, Birch and Lennox (eds.), Wiley-Liss, Inc., 1995, Chapter 2.2, "The Role of Monoclonal Antibodies in the Advancement of Immunoassay Technology," pp. 107-120.

Riechmann et al., "Reshaping human antibodies for therapy," *Nature 332*: 323-327, Mar. 24, 1988.

Roberts et al., "Generation of an antibody with enhanced affinity and specificity for its antigen by protein engineering," *Nature 328*: 731-734, Aug. 20, 1987.

Russell and Bennett, "Constuction and analysis of in vivo activity of *E. coli* promoter hybrids and promoter mutants that alter the .35 to .10 spacing," *Gene 20*: 231-243, 1982.

Scatchard, G., "The Attractions of Proteins for Small Molecules and Ions," *Ann. N.Y. Acad. Sci. 51*:660-672, 1949.

Sinkar et al., "Molecular biology of Ri-plasmid—A review," *J. Biosci. 11*(1-4): 47-57, Mar. 1987.

Struhl et al., "High-frequency transformation of yeast: Autonomous replication of hybrid DNA molecules," *Proc. Natl. Acad. Sci. USA 76*(3): 1035-1039, Mar. 1979.

Studier et al., "Use of T7 RNA Polymerase to Direct Expression of Cloned Genes," *Methods in Enzymology 185*: 60-89, 1990.

Subramani et al., "Expression of the Mouse Dihydrofolate Reductase Complementary Deoxyribonucleic Acid in Simian Virus 40 Vectors," *Molecular and Cellular Biology 1*(12): 854-864, 1981.

Verhoeyen et al., "Reshaping Human Antibodies: Grafting an Antilysozyme Activity," *Science 239*: 1534-1536, Mar. 25, 1988.

Vieira and Messing, "The pUC plasmids, an M13mp7-derived system for insertion mutagenesis and sequencing with synthetic universal primers," *Gene 19*: 259-268, 1982.

Wu et al. (eds.), *Methods in Gene Biotechnology*, Boca Raton: CRC Press, 1997, Chapter 10, "Analysis of Gene Expression at the RNA Level," pp. 225-239.

Wu et al. (eds.), *Methods in Gene Biotechnology*, Boca Raton: CRC Press, 1997, Chapter 2, "Rapid Isolation of Specific cDNA's or Genes by PCR," pp. 15-28.

Young et al., *Genetic Engineering of Microorganisms for Chemicals*, Hollaender et al. (eds.), Plenum Press, New York and London, 1982, "The Alcohol Dehydrogenase Gens of the Yeast, *Saccharomyces Cerevisiae*: Isolation, Structure, and Regulation," pp. 335-361.

Ada, *Fundamental Immunology*, William E. Paul, M.D. (ed.), 2nd Edition, Raven Press, New York, 1989, pp. 1010-1011.

Baird et al., "Epitopes Of Group A Streptococcal M Protein Shared With Antigens Of Articular Cartilage And Synovim," *The Journal Of Immunology 146*(9):3132-3137, 1991.

Beachey and Ofek, "Epithelial Cell Binding Of Group A Streptococci By Lipoteichoic Acid On Fimbriae Denuded Of M Protein," *The Journal Of Experimental Medicine 143*:759-771, 1976.

Beachey and Seyer, *Seminars in Infectious Disease*. vol. IV Bacterial Vaccines, Thieme-Stratton Inc., New York, New York, 1982, Chapter Fifty-Seven, "Primary Structure And Immuno-Chemistry Of Group A Streptococcal M Proteins," pp. 401-410.

Beachey and Stollerman, "Mediation of Cytotoxic Effects of Streptococcal M Protein by Nontype-Specific Antibody in Human Sera," *The Journal of Clinical Investigation 52*:2563-2570, 1973.

Beachey and Stollerman, "Toxic Effects Of Streptococcal M Protein On Platelets And Polymorphonuclear Leukocytes In Human Blood," *The Journal Of Experimental Medicine 134*:351-365, 1971.

Beachey et al., "Immunogenicity In Animals And Man Of A Structurally Defined Polypeptide Of Streptococcal M Protein," *Transactions Of The Association Of American Physicians*, vol. XCII:pp. 346-354, 1979.

Beachey et al., "Opsonic Antibodies Evoked By Hybrid Peptide Copies Of Types 5 and 24 Streptococcal M Proteins Synthesized In Tandem," *J. Exp. Med. 163*: 1451-1458, 1986.

Beachey et al., "Peptic Digestion of Streptococcal M Protein. II. Extraction of M Antigen from Group A Streptococcal With Pepsin," *Infection And Immunity 9*(5):891-896, 1974.

Beachey et al., "Repeating covalent structure of streptococcal M protein," *Proc. Natl. Acad. Sci. USA 75*(7):3163-3167, 1978.

Beachey et al., "Separation Of The Type Specific M Protein From Toxic Cross Reactive Antigens Of Group A Streptococci," *Transactions Of The Association Of American Physicians*. Ninetieth Session vol. XC: pp. 390-400, 1977.

Beall, B. et al., "Sequencing *emm*-Specific PCR Products for Routine and Accurate Typing of Group A Streptococci," *Journal of Clinical Microbiology 34*(4): 953-958, Apr. 1996.

Blenden et al., "Growth of *Listeria monocytogenes* in a Corn Silage Extract Medium," *American Journal Of Veterinary Research 29*(11):2237-2242, 1968.

Bricas et al., "Structure Et Synthese De La Subunite Peptide De La Paroi De Trois Bacteries Gram-Postif," *Peptides. Proceedings of the Eight European Peptide Symposium* Sep. 1966, Noordwijk, Neth., North-Holland Publishing Company: Amsterdam, Neth. And Interscience Publishers Division, John Wiley and Sons, Inc., New York, 1967, 286-292 (+ Biological Abstracts 50(4):Abstract No. 20361, 1936).

Chou and Fasman, "Prediction of Protein Conformation," *Biochemistry 13*(2):222-245, 1974.

Cunningham et al., "Human And Murine Antibodies Cross-Reactive With Streptococcal M Protein And Myosin Recognize The Sequence Gln-Lys-Ser-Lys-Gln In M Protein," *The Journal Of Immunology 143*(8):2677-2683, 1989.

Dale, "Group A Streptococcal Vaccines," *New Vaccines And New Vaccine Technology 13*(1):227-243, 1999.

Dale, "Group A Streptococcal Vaccines," *Pediatric Annals 27*:301-308, 1998.

Dale and Chiang, "Intranasal immunization with recombinant group A streptococcal M protein fragment fused to the B subunit of

*Escherichia coli* labile toxin protects mice against systemic challenge infections," *The Journal of Infectious Disease 171*(4): 1038-1041; Apr. 1995.

Dale et al., "Blastogenic Responses Of Human Lymphocytes To Structurally Defined Polypeptide Fragments Of Streptococcal M Protein," *The Journal Of Immunology 126*(4):1499-1505, 1981.

Dale et al., "Hyaluronate Capsule and Surface M Protein in Resistance to Opsonization of Group A Streptococci," *Infection And Immunity 64*(5):1495-1501, 1996.

Dixit et al., "Covalent Structure of Collagen: Amino Acid Sequence of α1-CB6A of Chick Skin Collagen," *Biochemistry 14*(9):1933-1938, 1975.

Edman and Begg, "A Protein Sequentor," *European J. Biochem. 1*: 80-91, 1967.

Fischetti, V.A. et al., "Protection Against Streptococcal Pharyngeal Colonization with a Vaccinia: M Protein Recombinant," *Science 244*: 1487-1490, Jun. 23, 1989.

Freimer and McCarty, "Rheumatic Fever," *Scientific American 213*(6):67-74, 1965.

Gibbons et al., "Studies of Individual Amino Acid Residues of the Decapeptide Tyrocidine A by Proton Double-Resonance Difference Spectroscopy in the Correlation Mode," *Biochemistry 14*(2):420-437, 1975.

Goldberg et al., "Serological Demonstration of H-Y (Male) Antigen on Mouse Sperm," *Nature 232*:478-480, 1971.

Hollingshead et al., "Complete Nucleotide Sequence of Type 6 M Protein of the Group A *Streptococcus*," *The Journal Of Biological Chemistry 261*(4):1677-1686, 1986.

Hopp and Woods, "Prediction of protein antigenic determinants from amino acid sequences," *Proc. Natl. Acad. Sci. USA 78*(6):3824-3828, 1981.

Hruby, D.E. et al., "Assembly and analysis of a function vaccinia virus 'amplicon' containing the C-repeat region from the M protein of *Streptococcus pyogenes*," *Proc. Natl. Acad. Sci. USA 88*: 3190-3194, Apr. 1991.

Jones et al., "Differential Effects Of Antibodies To Lyt-2 And L3 T4 On Cytolysis By Clones, Ia-Restricted T Cells Expressing Both Proteins," *The Journal Of Immunology 139*(2):380-384, 1987.

Kang, "Studies on the Location of Intermolecular Cross-Links in Collagen. Isolation of a CNBr Peptide Containing δ-Hydroxylysinonorleucine," *Biochemistry 11*(10):1828-1835, 1972.

Kang and Gross, "Amino Acid Sequence of Cyanogen Bromide Peptides from the Amino-Terminal Region of Chick Skin Collagen," *Biochemistry 9*(4):796-804, 1970.

Kaplan et al., "Group A Streptococcal Serotypes Isolated from Patients and Sibling Contacts During the Resurgence of Rheumatic Fever in the United States in the Mid-1980s," *The Journal Of Infectious Diseases 159*(1):101-103, 1989.

Koch et al., "Purification And Structural Analysis Of Streptolysin S (SLS)," *Federation Proceedings 42*(7): p. 1810, Abstract No. 309, 1983.

Kraus et al., "Identification Of An Epitope Of Type 1 Streptococcal M Protein That Is Shared With A 43-kDa Protein Of Human Myocardium And Renal Glomeruli," *The Journal Of Immunology 145*(12):4089-4093, 1990.

Krauss et al., "Sequence And Type-Specific Immunogenicity Of The Amino-Terminal Region Of Type 1 Streptococcal M Protein," *The Journal Of Immunology 139*(9):3084-3090, 1987.

Lancefield, "Persistence Of Type-Specific Antibodies In Man Following Infection With Group A Streptococci," *J. Exp. Med. 110*:271-292, 1959.

Laver et al., "Antigenic drift in type A influenza virus: Peptide mapping and antigenic analysis of A/PR/8/34 (HON1) variants selected with monoclonal antibodies," *Proc. Natl. Acad. Sci. USA 76*(3):1425-1429, 1979.

Lockey, "Urticaria of Unknown Origin," *Hospital Practice*: pp. 49-57, 1979.

Manjula and Fischetti, "Tropomyosin-Like Seven Residue Periodicity In Three Immunologically Distinct Streptococcal M Proteins And Its Implications For The Antiphagocytic Property Of The Molecule," *J. Exp. Med. 151*:695-708, 1980.

Marston and Hartley, "Solubilization of Protein Aggregates," *Methods in Enzymology 182*: 264-276, 1990.

Miller et al., "Conservation of Protective and Nonprotective Eptiopes in M Proteins of Group A Streptococci," *Infection And Immunity 56*(8):2198-2204, 1988.

Mori, K. et al., "Persistent Elevation of Immunoglobulin G Titer against the C Region of Recombinant Group A streptococcal M Protein in Patients with Rheumatic Fever," *Pediatric Research 39*(2): 336-342, 1996.

Phillips, Jr. et al., "Streptococcal M protein: α-Helical coiled-coil structure and arrangement on the cell surface," *Proc. Natl. Acad. Sci. USA 78*(8):4689-4693, 1981.

Rijn et al., "Group A Streptococcal Antigens Cross-Reactive With Mycocardium," *The Journal of Experimental Medicine 146*:579-599, 1977.

Robbins et al., "*Streptococcus pyogenes* Type 12 M Protein Gene Regulation by Upstream Sequences," *Journal Of Bacteriology 169*(12):5633-5640, 1987.

Seyer and Kang, "Covalent Structure of Collagen: Amino Acid Sequence of Cyanogen Bromide Peptides from the Amino-Terminal Segment of Type III Collagen of Human Liver," *Biochemistry 16*(6):1158-1164, 1977.

Seyer et al., "Primary Structural Similarities Between Types 5 And 24 M Proteins Of *Streptococcus pyogenes*," *Biochemical And Biophysical Research Communications 92*(2):546-553, 1980.

Smithies et al., "Quantitative Procedures for Use with the Edman-Begg Sequenator. Partial Sequences of Two Unusual Immunoglobulin Light Chains, Rzf and Sac," *Biochemistry 10*(26):4912-4921, 1971.

Vashishtha et al., "Reactivity of Antisera to Peptides Corresponding to the C-repeat Region of Streptococcal M Protein with Mammalian Coiled-Coil Proteins," *Abstracts Of The 91st General Meeting of the Society for Microbiology 1991*:p. 129, Abstract No. E-66, 1991.

Vashishtha and Fischetti, "Surface-Exposed Conserved Region of the Streptococcal M Protein Antibodies Cross-Reactive with Denatured Forms of Myosin," *The Journal of Immunology 150*(10): 4693-4701, May 15, 1993.

Weigent et al., "Induction of Human Gamma Interferon by Structurally Defined Polypeptide Fragments of Group A Streptococcal M Protein," *Infection And Immunity 43*(1):122-126, 1984.

Wistedt et al., "Identification of a plasminogen-binding motif in PAM, a bacterial surface protein," *Molecular Microbiology 18*(3): 569-578, 1995.

Wittner and Fox, "Homologues and Heterologous Protection of Mice with Group A Streptococcal M Protein Vaccines," *Infection and Immunity 15*(1): 104-108, Jan. 1977.

Hu, Mary C. et al., "Immunogenicity of a 26-Valent Group A Streptococcal Vaccine," *Infection and Immunity*, 70(4), 2171-2177, Apr. 2002.

\* cited by examiner

Hexavalent A.3

```
        M24--->
               9          18         27         36         45         54
5'  ATG GTC GCG ACT CGC TCT CAG ACA GAT ACT CTG GAA AAA GTA CAA GAA CGT GCT
    --- --- --- --- --- --- --- --- --- --- --- --- --- --- --- --- --- ---
    Met Val Ala Thr Arg Ser Gln Thr Asp Thr Leu Glu Lys Val Gln Glu Arg Ala 63         72         81         90         99        108
    GAC AAG TTT GAG ATA GAA AAC AAT ACG TTA AAA CTT AAG AAT AGT GAC TTA AGT
    --- --- --- --- --- --- --- --- --- --- --- --- --- --- --- --- --- ---
    Asp Lys Phe Glu Ile Glu Asn Asn Thr Leu Lys Leu Lys Asn Ser Asp Leu Ser 117        126        135        144        153        162
    TTT AAT AAT AAA GCG TTA AAA GAT CAT AAT GAT GAG TTA ACT GAA GAG TTG AGT
    --- --- --- --- --- --- --- --- --- --- --- --- --- --- --- --- --- ---
    Phe Asn Asn Lys Ala Leu Lys Asp His Asn Asp Glu Leu Thr Glu Glu Leu Ser

PmlI       M5--->
                   171        180        189        198        207        216
    AAT GCT AAA GAG AAA CTA CGT CAC GTG GCC GTG ACT CGC GGT ACA ATA AAT GAC
    --- --- --- --- --- --- --- --- --- --- --- --- --- --- --- --- --- ---
    Asn Ala Lys Glu Lys Leu Arg His Val Ala Val Thr Arg Gly Thr Ile Asn Asp 225        234        243        252        261        270
    CCG CAA AGA GCA AAA GAA GCT CTT GAC AAG TAT GAG CTA GAA AAC CAT GAC TTA
    --- --- --- --- --- --- --- --- --- --- --- --- --- --- --- --- --- ---
    Pro Gln Arg Ala Lys Glu Ala Leu Asp Lys Tyr Glu Leu Glu Asn His Asp Leu

BamHI    M6--->
                   279        288        297        306        315        324
    AAA ACT AAG GGA TCC CGT GTG TTT CCT CGC GGG ACG GTA GAA AAC CCG GAC AAA
    --- --- --- --- --- --- --- --- --- --- --- --- --- --- --- --- --- ---
    Lys Thr Lys Gly Ser Arg Val Phe Pro Arg Gly Thr Val Glu Asn Pro Asp Lys 333        342        351        360        369        378
    GCA CGA GAA CTT CTT AAC AAG TAT GAC GTA GAG AAC TCT ATG TTA CAA GCT AAT
    --- --- --- --- --- --- --- --- --- --- --- --- --- --- --- --- --- ---
    Ala Arg Glu Leu Leu Asn Lys Tyr Asp Val Glu Asn Ser Met Leu Gln Ala Asn
```

FIG. 2A

```
                    NcoI    M19--->
         387         396         405         414         423         432
AAT GAC AAG TTA CCA TGG CGT GTG CGT TAT ACT CGC CAT ACG CCA GAA GAT AAG
--- --- --- --- --- --- --- --- --- --- --- --- --- --- --- --- --- ---
Asn Asp Lys Leu Pro Trp Arg Val Arg Tyr Thr Arg His Thr Pro Glu Asp Lys 441         450         459         468         477         486
CTA AAA AAA ATT ATT GAC GAT CTT GAC GCA AAA GAA CAT GAA TTA CAA CAA CAG
--- --- --- --- --- --- --- --- --- --- --- --- --- --- --- --- --- ---
Leu Lys Lys Ile Ile Asp Asp Leu Asp Ala Lys Glu His Glu Leu Gln Gln Gln

PstI    M29--->
         495         504         513         522         531         540
AAT GAG AAG TTA TCT CTG CAG AAA GTG TAT ATT ACT CGT GGT ATG ACA AAA GAG
--- --- --- --- --- --- --- --- --- --- --- --- --- --- --- --- --- ---
Asn Glu Lys Leu Ser Leu Gln Lys Val Tyr Ile Thr Arg Gly Met Thr Lys Glu 549         558         567         576         585         594
GAC GTA GAA AAA ATT GCT AAC AAC CTT GAC ATA GAA AAC CAT GGG TTA AAA CAA
--- --- --- --- --- --- --- --- --- --- --- --- --- --- --- --- --- ---
Asp Val Glu Lys Ile Ala Asn Asn Leu Asp Ile Glu Asn His Gly Leu Lys Gln

KpnI
         603         612         621         630         639         648
CAG AAT GAA CAG TTA TCT ACT GAT AAA CAA GGT CTT GAA GAA CAG AAT GGT ACC
--- --- --- --- --- --- --- --- --- --- --- --- --- --- --- --- --- ---
Gln Asn Glu Gln Leu Ser Thr Asp Lys Gln Gly Leu Glu Glu Gln Asn Gly Thr

M14--->
         657         666         675         684         693         702
GAT CGC GTT AGT CGT TCT ATG TCA CGC GAT GAT CTA TTA AAC AGG GCT CAG GAT
--- --- --- --- --- --- --- --- --- --- --- --- --- --- --- --- --- ---
Asp Arg Val Ser Arg Ser Met Ser Arg Asp Asp Leu Leu Asn Arg Ala Gln Asp 711         720         729         738         747         756
CTT GAA GCA AAA AAC CAC GGG TTA GAA CAC CAG AAT ACT AAG TTA TCT ACT GAA
--- --- --- --- --- --- --- --- --- --- --- --- --- --- --- --- --- ---
Leu Glu Ala Lys Asn His Gly Leu Glu His Gln Asn Thr Lys Leu Ser Thr Glu
```

*FIG. 2B*

```
                                                              ClaI      M24--->
           765         774         783         792         801         810
      AAT AAA ACG CTT CAA GAA CAA GCA GAA GCA CGC CAG AAA GAA ATC GAT GTC GCG
      --- --- --- --- --- --- --- --- --- --- --- --- --- --- --- --- --- ---
      Asn Lys Thr Leu Gln Glu Gln Ala Glu Ala Arg Gln Lys Glu Ile Asp Val Ala 819         828         837         846         855         864
      ACT CGC TCT CAG ACA GAT ACT CTG GAA AAA GTA CAA GAA CGT GCT GAC AAG TTT
      --- --- --- --- --- --- --- --- --- --- --- --- --- --- --- --- --- ---
      Thr Arg Ser Gln Thr Asp Thr Leu Glu Lys Val Gln Glu Arg Ala Asp Lys Phe 873         882         891         900         909         918
      GAG ATA GAA AAC AAT ACG TTA AAA CTT AAG AAT AGT GAC TTA AGT TTT AAT AAT
      --- --- --- --- --- --- --- --- --- --- --- --- --- --- --- --- --- ---
      Glu Ile Glu Asn Asn Thr Leu Lys Leu Lys Asn Ser Asp Leu Ser Phe Asn Asn 927         936         945         954         963         972
      AAA GCG TTA AAA GAT CAT AAT GAT GAG TTA ACT GAA GAG TTG AGT AAT GCT AAA
      --- --- --- --- --- --- --- --- --- --- --- --- --- --- --- --- --- ---
      Lys Ala Leu Lys Asp His Asn Asp Glu Leu Thr Glu Glu Leu Ser Asn Ala Lys 981         990         999
      GAG AAA CTA CGT CAC CAC CAC CAC CAC CAC TGA 3'
      --- --- --- --- --- --- --- --- --- --- ---
      Glu Lys Leu Arg His His His His His His stop
```

*FIG. 2C*

Septavalent B.3a

```
         M1.0--->
             9          18         27         36         45         54
5' ATG AAC GGT GAT GGT AAT CCT AGG GAA GTT ATA GAA GAT CTT GCA GCA AAC AAT
   --- --- --- --- --- --- --- --- --- --- --- --- --- --- --- --- --- ---
   Met Asn Gly Asp Gly Asn Pro Arg Glu Val Ile Glu Asp Leu Ala Ala Asn Asn 63         72         81         90         99        108
   CCC GCA ATA CAA AAT ATA CGT TTA CGT CAC GAA AAC AAG GAC TTA AAA GCG AGA
   --- --- --- --- --- --- --- --- --- --- --- --- --- --- --- --- --- ---
   Pro Ala Ile Gln Asn Ile Arg Leu Arg His Glu Asn Lys Asp Leu Lys Ala Arg (XhoI-SalI)M12--->
            117        126        135        144        153        162
   TTA GAG AAT GCA ATG GAA GTT GCA GGA AGA GAT TTT AAG AGA GCT CTC GAC GAT
   --- --- --- --- --- --- --- --- --- --- --- --- --- --- --- --- --- ---
   Leu Glu Asn Ala Met Glu Val Ala Gly Arg Asp Phe Lys Arg Ala Leu Asp Asp 171        180        189        198        207        216
   CAT AGT GAT TTA GTC GCA GAA AAA CAA CGT TTA GAA GAT TTA GGA CAA AAA TTT
   --- --- --- --- --- --- --- --- --- --- --- --- --- --- --- --- --- ---
   His Ser Asp Leu Val Ala Glu Lys Gln Arg Leu Glu Asp Leu Gly Gln Lys Phe 225        234        243        252        261        270
   GAA AGA CTG AAA CAG CGT TCA GAA CTC TAC CTT CAG CAA TAC TAT GAT AAT AAA
   --- --- --- --- --- --- --- --- --- --- --- --- --- --- --- --- --- ---
   Glu Arg Leu Lys Gln Arg Ser Glu Leu Tyr Leu Gln Gln Tyr Tyr Asp Asn Lys

BamHI   Spa--->
            279        288        297        306        315        324
   TCA AAT GGA TAT AAA GGT GAC TGG TAT GTA CAA CAG TTA GGA TCC GAT TCA GTA
   --- --- --- --- --- --- --- --- --- --- --- --- --- --- --- --- --- ---
   Ser Asn Gly Tyr Lys Gly Asp Trp Tyr Val Gln Gln Leu Gly Ser Asp Ser Val 333        342        351        360        369        378
   AGT GGA TTA GAG GTG GCA GAC CCC TCT GAT AGT AAG AAA CTT ATT GAA TTA GGT
   --- --- --- --- --- --- --- --- --- --- --- --- --- --- --- --- --- ---
   Ser Gly Leu Glu Val Ala Asp Pro Ser Asp Ser Lys Lys Leu Ile Glu Leu Gly
```

FIG. 3A

```
          387           396           405           414           423           432
TTG GCT AAA TAC CTT AAT GAT AAA TTA CCC TTT AAA ACT AAA GAA GAT TCA GAG
--- --- --- --- --- --- --- --- --- --- --- --- --- --- --- --- --- ---
Leu Ala Lys Tyr Leu Asn Asp Lys Leu Pro Phe Lys Thr Lys Glu Asp Ser Glu

PstI    M28--->
          441           450           459           468           477           486
ATT TTA TCA GAG TTA CGT GAT GTA TTA AAA AAT CTG CAG GAG TCT CCA AAA AGT
--- --- --- --- --- --- --- --- --- --- --- --- --- --- --- --- --- ---
Ile Leu Ser Glu Leu Arg Asp Val Leu Lys Asn Leu Gln Glu Ser Pro Lys Ser 495           504           513           522           531           540
ACT GAG ACT TCT GCT AAT GGA GCT GAT AAA TTA GCT GAT GCA TAC AAC ACA TTG
--- --- --- --- --- --- --- --- --- --- --- --- --- --- --- --- --- ---
Thr Glu Thr Ser Ala Asn Gly Ala Asp Lys Leu Ala Asp Ala Tyr Asn Thr Leu 549           558           567           576           585           594
CTT ACT GAA CAT GAG AAA CTC AGA GAT GAG TAT TAT ACA TTA ATT GAT GCT AAA
--- --- --- --- --- --- --- --- --- --- --- --- --- --- --- --- --- ---
Leu Thr Glu His Glu Lys Leu Arg Asp Glu Tyr Tyr Thr Leu Ile Asp Ala Lys

KpnI    M3--->
          603           612           621           630           639           648
GAA GAA GAA CCT CGC TAT AAA GCA TTG GGT ACC TTG TTA GAT CAG GTT ACA CAA
--- --- --- --- --- --- --- --- --- --- --- --- --- --- --- --- --- ---
Glu Glu Glu Pro Arg Tyr Lys Ala Leu Gly Thr Leu Leu Asp Gln Val Thr Gln 657           666           675           684           693           702
TTA TAT ACT AAA CAT AAT AGT AAT TAC CAA CAA TAT AAT GCA CAA GCT GGC AGA
--- --- --- --- --- --- --- --- --- --- --- --- --- --- --- --- --- ---
Leu Tyr Thr Lys His Asn Ser Asn Tyr Gln Gln Tyr Asn Ala Gln Ala Gly Arg 711           720           729           738           747           756
CTT GAC CTG AGA CAA AAG GCT GAA TAT CTA AAA GGC CTT AAT GAT TGG GCT GAG
--- --- --- --- --- --- --- --- --- --- --- --- --- --- --- --- --- ---
Leu Asp Leu Arg Gln Lys Ala Glu Tyr Leu Lys Gly Leu Asn Asp Trp Ala Glu

KpnI    M1.2--->
          765           774           783           792           801           810
CGC CTG TTA CAA GAG TTA AAT GGT ACC AAC AAT GAT GGT CGT TCT CGT GAC GTT
--- --- --- --- --- --- --- --- --- --- --- --- --- --- --- --- --- ---
Arg Leu Leu Gln Glu Leu Asn Gly Thr Asn Asn Asp Gly Arg Ser Arg Asp Val
```

*FIG. 3B*

```
        819         828         837         846         855         864
ACG GAA GAG ATT GCA GCA AAC AAT ACC ACA GTA CAA AAT ATA CGT TTA CGT AAC
--- --- --- --- --- --- --- --- --- --- --- --- --- --- --- --- --- ---
Thr Glu Glu Ile Ala Ala Asn Asn Thr Thr Val Gln Asn Ile Arg Leu Arg Asn 873         882         891         900         909         918
GAA AAC AAG AAC TTA AAA GCG AAA AAC GAG GAC TTA GAA GCG AGA TTA GAG AAT
--- --- --- --- --- --- --- --- --- --- --- --- --- --- --- --- --- ---
Glu Asn Lys Asn Leu Lys Ala Lys Asn Glu Asp Leu Glu Ala Arg Leu Glu Asn

EcoRI    M18--->
        927         936         945         954         963         972
GCA ATG AAT GTT GCA GGA CGC GAT TTT AAG CGT GCT GAA TTC GCA CCT CTT ACT
--- --- --- --- --- --- --- --- --- --- --- --- --- --- --- --- --- ---
Ala Met Asn Val Ala Gly Arg Asp Phe Lys Arg Ala Glu Phe Ala Pro Leu Thr 981         990         999        1008        1017        1026
CGT GCT ACA GCA GAC AAT AAA GAC GAA TTA ATA AAA AGA GCT AAC GGT TAT GAG
--- --- --- --- --- --- --- --- --- --- --- --- --- --- --- --- --- ---
Arg Ala Thr Ala Asp Asn Lys Asp Glu Leu Ile Lys Arg Ala Asn Gly Tyr Glu 1035        1044        1053        1062        1071        1080
ATA CAG AAC CAT CAG TTA ACA GTT GAG AAT AAA AAA TTA AAA ACT GAT AAG GAA
--- --- --- --- --- --- --- --- --- --- --- --- --- --- --- --- --- ---
Ile Gln Asn His Gln Leu Thr Val Glu Asn Lys Lys Leu Lys Thr Asp Lys Glu

PmlI     M1.0--->
       1089        1098        1107        1116        1125        1134
CAG TTA ACA AAA GAG AAT GAT GAT TTA AAA CAC GTG AAC GGT GAT GGT AAT CCT
--- --- --- --- --- --- --- --- --- --- --- --- --- --- --- --- --- ---
Gln Leu Thr Lys Glu Asn Asp Asp Leu Lys His Val Asn Gly Asp Gly Asn Pro 1143        1152        1161        1170        1179        1188
CGT GAA GTT ATA GAA GAT CTT GCA GCA AAC AAT CCC GCA ATA CAA AAT ATA CGT
--- --- --- --- --- --- --- --- --- --- --- --- --- --- --- --- --- ---
Arg Glu Val Ile Glu Asp Leu Ala Ala Asn Asn Pro Ala Ile Gln Asn Ile Arg 1197        1206        1215        1224        1233        1242
TTA CGT CAC GAA AAC AAG GAC TTA AAA GCG AGA TTA GAG AAT GCA ATG GAA GTT
--- --- --- --- --- --- --- --- --- --- --- --- --- --- --- --- --- ---
Leu Arg His Glu Asn Lys Asp Leu Lys Ala Arg Leu Glu Asn Ala Met Glu Val
```

*FIG. 3C*

```
      1251         1260        1269         1278        1287
GCA GGA CGT GAT TTT AAG CGT GCT CAC CAC CAC CAC CAC CAC TAA 3'
--- --- --- --- --- --- --- --- --- --- --- --- --- --- ---
Ala Gly Arg Asp Phe Lys Arg Ala His His His His His His stop
```

*FIG. 3D*

Septavalent C.2

```
     M2--->
              9              18              27              36              45              54
5'  ATG AGT AAG AAC CCT GTC CCT GTC AAA AAA GAA GCA AAA TTA AGT GAA GCA GAA
    --- --- --- --- --- --- --- --- --- --- --- --- --- --- --- --- --- ---
    Met Ser Lys Asn Pro Val Pro Val Lys Lys Glu Ala Lys Leu Ser Glu Ala Glu 63              72              81              90              99             108
    TTA CAT GAC AAA ATT AAA AAC CTT GAA GAG GAA AAA GCA GAA TTA TTC GAG AAA
    --- --- --- --- --- --- --- --- --- --- --- --- --- --- --- --- --- ---
    Leu His Asp Lys Ile Lys Asn Leu Glu Glu Glu Lys Ala Glu Leu Phe Glu Lys (XhoI-SalI)M43--->
            117             126             135             144             153             162
    CTC GAC GAA GAA CAC CCT GAC GTT GTC GCT GCT AGA GAA AGC GTA CTA AAT AAT
    --- --- --- --- --- --- --- --- --- --- --- --- --- --- --- --- --- ---
    Leu Asp Glu Glu His Pro Asp Val Val Ala Ala Arg Glu Ser Val Leu Asn Asn 171             180             189             198             207             216
    GTC CGT GTA CCG GGT ACA CTT TGG CTA CGT CAA AAA GAA GAA AAT GAC AAA CTT
    --- --- --- --- --- --- --- --- --- --- --- --- --- --- --- --- --- ---
    Val Arg Val Pro Gly Thr Leu Trp Leu Arg Gln Lys Glu Glu Asn Asp Lys Leu

NheI
            225             234             243             252             261             270
    AAA TTG GAA AAG AAA GGG CTT GAG ACT GAG TTA CAG GAA AAG GAA CAA GCT AGC
    --- --- --- --- --- --- --- --- --- --- --- --- --- --- --- --- --- ---
    Lys Leu Glu Lys Lys Gly Leu Glu Thr Glu Leu Gln Glu Lys Glu Gln Ala Ser

M94--->
            279             288             297             306             315             324
    GAA GAA GCA TCA AAT AAT GGG CAA CTC ACA TTA CAG CAT AAA AAT AAT GCA TTG
    --- --- --- --- --- --- --- --- --- --- --- --- --- --- --- --- --- ---
    Glu Glu Ala Ser Asn Asn Gly Gln Leu Thr Leu Gln His Lys Asn Asn Ala Leu 333             342             351             360             369             378
    ACT AGT GAG AAT GAG TCT CTT CGT CGT GAA AAA GAT CGT TAT TTG TAT GAA AAA
    --- --- --- --- --- --- --- --- --- --- --- --- --- --- --- --- --- ---
    Thr Ser Glu Asn Glu Ser Leu Arg Arg Glu Lys Asp Arg Tyr Leu Tyr Glu Lys
```

FIG. 4A

```
              BamHI    M22--->
      387         396         405         414         423         432
GAA GAA TTA GAA GGA TCC GAG TCA TCA AAT AAT GCG GAG TCA TCA AAC ATT TCT
--- --- --- --- --- --- --- --- --- --- --- --- --- --- --- --- --- ---
Glu Glu Leu Glu Gly Ser Glu Ser Ser Asn Asn Ala Glu Ser Ser Asn Ile Ser 441         450         459         468         477         486
CAA GAA AGC AAA CTA ATA AAT ACA TTG ACT GAT GAA AAT GAG AAA CTC AGA GAA
--- --- --- --- --- --- --- --- --- --- --- --- --- --- --- --- --- ---
Gln Glu Ser Lys Leu Ile Asn Thr Leu Thr Asp Glu Asn Glu Lys Leu Arg Glu 495         504         513         522         531         540
GAG CTC CAA CAG TAT TAT GCA TTA AGT GAT GCT AAA GAA GAA GAA CCT CGT TAT
--- --- --- --- --- --- --- --- --- --- --- --- --- --- --- --- --- ---
Glu Leu Gln Gln Tyr Tyr Ala Leu Ser Asp Ala Lys Glu Glu Glu Pro Arg Tyr

PstI    M11--->
      549         558         567         576         585         594
AAA GCA CTG CAG ACT GAA GTT AAG GCT GCG GGG CAA AGC GCT CCT AAA GGT ACA
--- --- --- --- --- --- --- --- --- --- --- --- --- --- --- --- --- ---
Lys Ala Leu Gln Thr Glu Val Lys Ala Ala Gly Gln Ser Ala Pro Lys Gly Thr 603         612         621         630         639         648
AAC GTG AGC GCA GAC CTA TAT AAT TCG CTA TGG GAT GAA AAT AAA ACT CTT AGA
--- --- --- --- --- --- --- --- --- --- --- --- --- --- --- --- --- ---
Asn Val Ser Ala Asp Leu Tyr Asn Ser Leu Trp Asp Glu Asn Lys Thr Leu Arg 657         666         675         684         693         702
GAA AAA CAA GAA GAG TAT ATA ACA AAA ATT CAA AAT GAA GAG ACA AAA AAT AAA
--- --- --- --- --- --- --- --- --- --- --- --- --- --- --- --- --- ---
Glu Lys Gln Glu Glu Tyr Ile Thr Lys Ile Gln Asn Glu Glu Thr Lys Asn Lys

KpnI     M59--->
      711         720         729         738         747         756
GGT ACC GAA CAA GCA AAA AAT AAT AAT GGG GAA CTC ACA TTA CAG CAA AAA TAC
--- --- --- --- --- --- --- --- --- --- --- --- --- --- --- --- --- ---
Gly Thr Glu Gln Ala Lys Asn Asn Asn Gly Glu Leu Thr Leu Gln Gln Lys Tyr 765         774         783         792         801         810
GAT GCA TTG ACT AAT GAG AAT AAG TCT CTT CGT CGT GAG CGT GAT AAC TAT TTA
--- --- --- --- --- --- --- --- --- --- --- --- --- --- --- --- --- ---
Asp Ala Leu Thr Asn Glu Asn Lys Ser Leu Arg Arg Glu Arg Asp Asn Tyr Leu
```

*FIG. 4B*

```
                    NcoI       M33--->
        819         828        837        846        855        864
AAT TAT TTA TAT GAA AAA CCA TGG GAA GAG CAT GAA AAA GTA ACA CAA GCC AGA
--- --- --- --- --- --- --- --- --- --- --- --- --- --- --- --- --- ---
Asn Tyr Leu Tyr Glu Lys Pro Trp Glu Glu His Glu Lys Val Thr Gln Ala Arg 873         882        891        900        909        918
GAA GCG GTT ATC AGA GAG ATG CAA CAG AGG GGG ACA AAT TTT GGA CCT CTG TTA
--- --- --- --- --- --- --- --- --- --- --- --- --- --- --- --- --- ---
Glu Ala Val Ile Arg Glu Met Gln Gln Arg Gly Thr Asn Phe Gly Pro Leu Leu

PmlI
        927         936        945        954        963        972
GCA AGT ACA ATG CGA GAT AAT CAC AAT TTA AAA GAA ACG CTT GAC AAA ACT CAC
--- --- --- --- --- --- --- --- --- --- --- --- --- --- --- --- --- ---
Ala Ser Thr Met Arg Asp Asn His Asn Leu Lys Glu Thr Leu Asp Lys Thr His

M2--->
        981         990        999        1008       1017       1026
GTG AGT AAG AAC CCT GTC CCT GTC AAA AAA GAA GCA AAA TTA AGT GAA GCA GAA
--- --- --- --- --- --- --- --- --- --- --- --- --- --- --- --- --- ---
Val Ser Lys Asn Pro Val Pro Val Lys Lys Glu Ala Lys Leu Ser Glu Ala Glu 1035        1044       1053       1062       1071       1080
TTA CAT GAC AAA ATT AAA AAC CTT GAA GAG GAA AAA GCA GAA TTA TTC GAG AAA
--- --- --- --- --- --- --- --- --- --- --- --- --- --- --- --- --- ---
Leu His Asp Lys Ile Lys Asn Leu Glu Glu Glu Lys Ala Glu Leu Phe Glu Lys 1089        1098       1107
CTC GAG CAC CAC CAC CAC CAC CAC TGA 3'
--- --- --- --- --- --- --- --- ---
Leu Glu His His His His His His stop
```

*FIG. 4C*

Septavalent D.3

```
        M89--->
            9           18          27          36          45          54
5' ATG AGT GAC AAT ATT AAT CGT TCT GTC TCT GTC AAA GAT AAT GAA AAA GAA TTA
   --- --- --- --- --- --- --- --- --- --- --- --- --- --- --- --- --- ---
   Met Ser Asp Asn Ile Asn Arg Ser Val Ser Val Lys Asp Asn Glu Lys Glu Leu 63          72          81          90          99         108
   CAT AAC AAA ATT GCA GAC CTT GAA GAG GAA AGG GGT GAA CAT CTA GAC AAA ATA
   --- --- --- --- --- --- --- --- --- --- --- --- --- --- --- --- --- ---
   His Asn Lys Ile Ala Asp Leu Glu Glu Glu Arg Gly Glu His Leu Asp Lys Ile

BamHI   M101--->
          117         126         135         144         153         162
   GAT GAA CTA AAA GAA GAA CTA AAA GCA AAG GAA AAA AGT TCA GGA TCC GCT GAT
   --- --- --- --- --- --- --- --- --- --- --- --- --- --- --- --- --- ---
   Asp Glu Leu Lys Glu Glu Leu Lys Ala Lys Glu Lys Ser Ser Gly Ser Ala Asp 171         180         189         198         207         216
   CAC CCT AGC TAT ACC GCT GCT AAA GAT GAA GTA CTA AGT AAG TTC TCT GTA CCG
   --- --- --- --- --- --- --- --- --- --- --- --- --- --- --- --- --- ---
   His Pro Ser Tyr Thr Ala Ala Lys Asp Glu Val Leu Ser Lys Phe Ser Val Pro 225         234         243         252         261         270
   GGT CAT GTT TGG GCA CAT GAA AGA GAA AAA AAT GAC AAA CTT AGC TCG GAA AAT
   --- --- --- --- --- --- --- --- --- --- --- --- --- --- --- --- --- ---
   Gly His Val Trp Ala His Glu Arg Glu Lys Asn Asp Lys Leu Ser Ser Glu Asn

NheI    M77--->
          279         288         297         306         315         324
   GAA GGG CTT AAG GCT GGT TTA CAG GAA AAG GAA CAA GCT AGC GAA GGG GTT TCT
   --- --- --- --- --- --- --- --- --- --- --- --- --- --- --- --- --- ---
   Glu Gly Leu Lys Ala Gly Leu Gln Glu Lys Glu Gln Ala Ser Glu Gly Val Ser 333         342         351         360         369         378
   GTA GGT TCA GAT GCA TCA CTA CAT AAC CGC ATT ACA GAC CTT GAA GAG GAA AGA
   --- --- --- --- --- --- --- --- --- --- --- --- --- --- --- --- --- ---
   Val Gly Ser Asp Ala Ser Leu His Asn Arg Ile Thr Asp Leu Glu Glu Glu Arg
```

FIG. 5A

```
              387         396         405         414         423         432
         GAA AAA TTA TTA AAT AAA TTA GAT AAA GTT GAA GAA GAG CAT AAA AAA GAT CAT
         --- --- --- --- --- --- --- --- --- --- --- --- --- --- --- --- --- ---
         Glu Lys Leu Leu Asn Lys Leu Asp Lys Val Glu Glu Glu His Lys Lys Asp His

KpnI        M114--->
              441         450         459         468         477         486
         GAA CAA GGT ACC AAC AGT AAG AAC CCT GCC CCT GCC CCT GCC TCT GCT GTC CCT
         --- --- --- --- --- --- --- --- --- --- --- --- --- --- --- --- --- ---
         Glu Gln Gly Thr Asn Ser Lys Asn Pro Ala Pro Ala Pro Ala Ser Ala Val Pro 495         504         513         522         531         540
         GTC AAA AAA GAA GCA ACA AAA TTA AGT GAA GCA GAA TTA TAT AAC AAA ATT CAA
         --- --- --- --- --- --- --- --- --- --- --- --- --- --- --- --- --- ---
         Val Lys Lys Glu Ala Thr Lys Leu Ser Glu Ala Glu Leu Tyr Asn Lys Ile Gln

BamHI       M75--->
              549         558         567         576         585         594
         GAA CTT GAA GAG GGA AAA GCA GAA TTA TTC GGA TCC GAA GAA GAA CGT ACT TTT
         --- --- --- --- --- --- --- --- --- --- --- --- --- --- --- --- --- ---
         Glu Leu Glu Glu Gly Lys Ala Glu Leu Phe Gly Ser Glu Glu Glu Arg Thr Phe 603         612         621         630         639         648
         ACT GAG TTA CCA TAT GAA GCA CGA TAC AAA GCA TGG AAA AGT GAA AAT GAT GAG
         --- --- --- --- --- --- --- --- --- --- --- --- --- --- --- --- --- ---
         Thr Glu Leu Pro Tyr Glu Ala Arg Tyr Lys Ala Trp Lys Ser Glu Asn Asp Glu 657         666         675         684         693         702
         CTT CGG GAA AAT TAT CGT CGT ACC TTA GAT AAG TTT AAT ACT GAG CAA GGT AAG
         --- --- --- --- --- --- --- --- --- --- --- --- --- --- --- --- --- ---
         Leu Arg Glu Asn Tyr Arg Arg Thr Leu Asp Lys Phe Asn Thr Glu Gln Gly Lys

HindIII    M76--->
              711         720         729         738         747         756
         ACT ACG CGC TTA GAA GAA CAA AAT AAG CTT GCG GAC GCG AAC TCG AAA AGC GTT
         --- --- --- --- --- --- --- --- --- --- --- --- --- --- --- --- --- ---
         Thr Thr Arg Leu Glu Glu Gln Asn Lys Leu Ala Asp Ala Asn Ser Lys Ser Val 765         774         783         792         801         810
         TCT AAT AGT AAC GTG AGC ATA AAT CTA TAT AAT GAG CTA CAG GCT GAA CAT GAT
         --- --- --- --- --- --- --- --- --- --- --- --- --- --- --- --- --- ---
         Ser Asn Ser Asn Val Ser Ile Asn Leu Tyr Asn Glu Leu Gln Ala Glu His Asp
```

*FIG. 5B*

```
      819         828         837         846         855         864
AAG CTA CAG ACT AAA CAT GAG GAG CTA TTG GCT GAA CAT GAT GCT CTT AAA GAA
--- --- --- --- --- --- --- --- --- --- --- --- --- --- --- --- --- ---
Lys Leu Gln Thr Lys His Glu Glu Leu Leu Ala Glu His Asp Ala Leu Lys Glu

EcoRI    M92--->
      873         882         891         900         909         918
AAA CAA GAT AAA AAT CAA GAA TTC GAT GAC CGG AGC GTT TCT ACT AAT AGT GGT
--- --- --- --- --- --- --- --- --- --- --- --- --- --- --- --- --- ---
Lys Gln Asp Lys Asn Gln Glu Phe Asp Asp Arg Ser Val Ser Thr Asn Ser Gly 927         936         945         954         963         972
AGC GTG AGC ACA CCA TAT AAT AAC CTA TTG AAT GAA TAT GAT GAC CTA TTG GCT
--- --- --- --- --- --- --- --- --- --- --- --- --- --- --- --- --- ---
Ser Val Ser Thr Pro Tyr Asn Asn Leu Leu Asn Glu Tyr Asp Asp Leu Leu Ala 981         990         999        1008        1017        1026
AAA CAT GGT GAG CTA TTG AGT GAA TAT GAT GCT CTT AAA GAA AAA CAA GAT AAA
--- --- --- --- --- --- --- --- --- --- --- --- --- --- --- --- --- ---
Lys His Gly Glu Leu Leu Ser Glu Tyr Asp Ala Leu Lys Glu Lys Gln Asp Lys

NheI     M89--->
     1035        1044        1053        1062        1071        1080
AAT CAA GAA GCT AGC AGT GAC AAT ATT AAT CGT TCT GTC TCT GTC AAA GAT AAT
--- --- --- --- --- --- --- --- --- --- --- --- --- --- --- --- --- ---
Asn Gln Glu Ala Ser Ser Asp Asn Ile Asn Arg Ser Val Ser Val Lys Asp Asn 1089        1098        1107        1116        1125        1134
GAA AAA GAA TTA CAT AAC AAA ATT GCA GAC CTT GAA GAG GAA AGG GGT GAA CAT
--- --- --- --- --- --- --- --- --- --- --- --- --- --- --- --- --- ---
Glu Lys Glu Leu His Asn Lys Ile Ala Asp Leu Glu Glu Glu Arg Gly Glu His 1143        1152        1161        1170        1179        1188
CTA GAC AAA ATA GAT GAA CTA AAA GAA GAA CTA AAA GCA AAG GAA AAA AGT TCA
--- --- --- --- --- --- --- --- --- --- --- --- --- --- --- --- --- ---
Leu Asp Lys Ile Asp Glu Leu Lys Glu Glu Leu Lys Ala Lys Glu Lys Ser Ser 1197        1206
CAC CAC CAC CAC CAC CAC TGA 3'
--- --- --- --- --- --- ---
His His His His His His stop
```

*FIG. 5C*

MULTIVALENT STREPTOCOCCAL VACCINE COMPOSITIONS AND METHODS FOR USE

CROSS-REFERENCE TO RELATED APPLICATION

This application claims the benefit of U.S. Provisional Patent Application No. 60/348,434 filed Oct. 26, 2001. This provisional application is incorporated herein by reference in its entirety.

STATEMENT OF GOVERNMENT INTEREST

This invention was made with government support under Grant No. AI-10085 awarded by the National Institutes of Health, and support from the Department of Veteran Affairs, Merit Review funds. The government may have certain rights in this invention.

BACKGROUND OF THE INVENTION

1. Field of the Invention

The present invention relates generally to the prevention of infectious disease, and more specifically, to compositions comprising multivalent hybrid polypeptides having immunogenic M protein and Spa peptides capable of eliciting protective immunity.

2. Description of the Related Art

Group A streptococcal pharyngitis is one of the most common bacterial infections in school-age children. In addition to streptococcal pharyngitis, there may be associated nonsuppurative sequela, such as acute rheumatic fever (ARF). Although the incidence of ARF has declined in developed countries, the disease remains rampant in developing countries (Community prevention and control of cardiovascular diseases. Report of a WHO expert committee. World Health Organization. 1986:732). Another form of streptococcal infection is invasive, which afflicts thousands of children and adults each year, often resulting in death or significant morbidity (Stevens, *J. Infect. Dis.* 2:S366, 1999). Efforts to develop a vaccine that would prevent group A streptococcal infections have been ongoing for over eight decades (Dochez et al., *J. Exp. Med.* 30:179, 1919; Lancefield, *J. Exp. Med.* 47:91, 1928).

Hence, a need exists for identifying and developing compositions therapeutically effective against streptococcal infections, particularly those compositions that can function as a vaccine and elicit protective immunity. Furthermore, there is a need for vaccine formulations that can be varied to protect against or treatment for infection by different streptococcal serotypes. The present invention meets such needs, and further provides other related advantages.

SUMMARY OF THE INVENTION

The present invention provides the discovery of therapeutic formulations of multivalent hybrid polypeptides, particularly a cocktail of hybrid polypeptides useful for eliciting a protective immune response having broadly protective opsonic antibodies in the absence of tissue cross-reactive antibodies. Hybrid polypeptides of the invention comprise at least six different linked immunogenic peptides, wherein each peptide comprises an amino-terminal portion of a streptococcal M protein of at least 30 amino acids, and wherein the polypeptide has an amino-terminal peptide that is reiterated as a carboxy-terminal peptide and the polypeptide is capable of eliciting an immune response against more than one serotype of group A streptococci.

In one aspect, the invention provides a hybrid polypeptide, comprising at least six different linked immunogenic peptides, wherein each peptide comprises an amino-terminal portion of a streptococcal M protein of at least 30 amino acids, and wherein the polypeptide has an amino-terminal peptide that is reiterated as a carboxy-terminal peptide and the polypeptide is capable of eliciting an immune response against more than one antigen of group A streptococci comprising at least M5, M6, M14, M19, M24, and M29. In other embodiments, the polypeptide elicits an immune response against more than one antigen of group A streptococci comprising at least M2, M11, M22, M33, M43, M59, and M94, or at least M75, M76, M77, M89, M92, M101, and M114, or at least Spa, M1.0, M1.2, M3, M12, M18, and M28, or against 27 or more antigens of group A streptococci. In more embodiments, the amino-terminal immunogenic peptide of the hybrid polypeptide is M24, M1, M2, or M89. In still other embodiments, the polypeptides are recombinant and the immunogenic peptides are linked in tandem, the polypeptides having a structure of M24-M5-M6-M19-M29-M14-M24, M2-M43-M94-M22-M11-M59-M33-M2, M89-M101-M77-M114-M75-M76-M92-M89, or M1.0-M12-Spa-M28-M3-M1.2-M18-M1.0. In yet other embodiments, the hybrid polypeptides comprise the amino acid sequence of SEQ ID NOS:2, 4, 6, or 8. In other embodiments, the immunogenic peptides are linked by at least two amino acids encoded by a nucleic acid sequence that is a restriction enzyme recognition site, wherein the recognition site includes at least one of BamHI, ClaI, EcoRI, HindIII, KpnI, NcoI, NheI, PmlI, PstI, SalI, and XhoI. In further embodiments, any of the aforementioned hybrid polypeptides capable of eliciting at least one opsonic antibody that is not a tissue cross-reactive antibody in a subject, wherein the subject is a human or an animal. In more embodiments, any of the aforementioned hybrid polypeptides further comprising a carboxy-terminal tag, wherein the carboxy-terminal tag is selected from the group consisting of alkaline phosphatase, β-galactosidase, hexahistidine, FLAG®, XPRESS®, and GST. In still more embodiments, any of the aforementioned hybrid polypeptides or fusion proteins further comprise at least one additional carboxy-terminal amino acid, wherein the additional carboxy-terminal amino acid is a D-amino acid or cysteine.

In another aspect, the invention provides any of the aforementioned hybrid polypeptides or fusion proteins wherein the polypeptides are synthetic. In certain embodiments, the synthetic hybrid polypeptides have one or more amino acids altered to a corresponding D-amino acid or are linked to an alkane such as acrylamide or an analog or derivative thereof. In a further embodiment, the synthetic hybrid polypeptides have immunogenic peptides linked to form a lysine core-branched peptide.

In still another aspect, the invention includes a nucleic acid molecule comprising a sequence encoding a hybrid polypeptide of SEQ ID NOS:2, 4, 6, or 8. In a related embodiment, there is provided a nucleic acid expression construct comprising an expression control sequence operably linked to a polynucleotide encoding a hybrid polypeptide of SEQ ID NOS:2, 4, 6, or 8. In other embodiments, the expression construct comprises a nucleic acid expression vector selected from the group comprising a plasmid, phagemid, shuttle vector, cosmid, or virus. In one embodiment, the vector is plasmid pT5 (SEQ ID NO:17). In still another embodiment, there is provided a host cell containing any of the aforementioned nucleic acid constructs. In yet other embodiments, the host cell is selected from a bacterium, a yeast cell, a nematode cell, an insect cell, or a mammalian cell. In one embodiment, the host cell is the bacterium *Escherichia coli*.

In a further aspect, the present invention provides a plurality of antibodies, comprising two or more different antibodies wherein each antibody is specific for a different immunogenic peptide of a hybrid polypeptide, the polypeptide comprises at least six different immunogenic peptides linked in tandem, each peptide comprises at least 30 amino acids and the amino-terminal peptide is reiterated as a carboxy-terminal peptide, wherein the polypeptide is capable of eliciting an immune response against more than one antigen of group A streptococci comprising at least M5, M6, M14, M19, M24, and M29. In other embodiments, the plurality of antibodies are specific for more than one antigen of group A streptococci comprising at least M2, M11, M22, M33, M43, M59, and M94, or at least M75, M76, M77, M89, M92, M101, and M114, or at least Spa, M1.0, M1.2, M3, M12, M18, and M28, or specific for 27 or more antigens of group A streptococci. In yet other embodiments, any of the aforementioned antibodies wherein the hybrid polypeptides comprise the amino acid sequence of SEQ ID NOS:2, 4, 6, or 8. In other embodiments, any of the aforementioned antibodies are opsonic and not tissue cross-reactive in a subject. In one embodiment, the antibodies are polyclonal.

In yet another aspect, there is provided a method of producing a hybrid polypeptide, comprising culturing a host cell containing any of the aforementioned nucleic acid expression vectors comprising at least one expression control sequence operably linked to a nucleic acid molecule encoding a hybrid polypeptide of SEQ ID NOS:2, 4, 6, or 8, under conditions and for a time sufficient for expression of the polypeptide. In a related aspect, the invention provides any of the aforementioned hybrid polypeptides produced by the aforementioned method.

In another aspect, there is provided a composition comprising a pharmaceutically acceptable carrier and any of the aforementioned hybrid polypeptides. In other aspects, the invention is a cocktail composition comprising a pharmaceutically acceptable carrier and a mixture of at least two or three of any of the aforementioned hybrid polypeptides. In one embodiment, the cocktail compositions include at least one of the hybrid polypeptides having a Spa immunogenic peptide. In other embodiments, provided are any of the aforementioned compositions wherein the hybrid polypeptides are mixed in equimolar amounts. In further embodiments, any of the aforementioned compositions further comprise an adjuvant such as alum or Freund's.

In still another aspect, the invention provides a method for preventing a microbial infection, comprising administering to a subject any of the aforementioned compositions at a dose sufficient to elicit antibodies specific for one or more hybrid polypeptide, wherein the antibodies are opsonic and are not tissue cross-reactive. In certain embodiments, the microbial infection being prevented is a streptococcal infection and in a related embodiment is a group A streptococcal infection. In some embodiments, any of the aforementioned compositions are administered to a subject by a route selected from enteral, parenteral, transdermal, transmucosal, or inhalation. In further embodiments, the compositions are administered to a human or animal subject and the compositions further comprise an adjuvant such as alum or Freund's. In another related aspect, there is provided isolated antibodies produced by the aforementioned methods for preventing a microbial infection. In certain embodiments, the antibodies produced by these methods will comprise at least one antibody specific for a M serotype not represented in a hybrid polypeptide, such as M4. In still another embodiment, there is provided a method for treating or preventing a microbial infection comprising administering to a subject a composition comprising a pharmaceutically acceptable carrier and any of the aforementioned plurality of antibodies. In one embodiment, the subject is an animal or human.

BRIEF DESCRIPTION OF THE DRAWINGS

FIGS. 2A to 2C show the nucleotide and amino acid sequence of hybrid polypeptide Hexavalent A.3 (SEQ ID NO: 1-2). The restriction enzyme sites and the beginning point of each M serotype immunogenic peptide are indicated. Eleven Arg codons were optimized for expression in *E. coli* by mutating AGG/AGA codons to CGT/CGC codons (mutated bases are underlined).

FIGS. 3A to 3D show the nucleotide and amino acid sequence of hybrid polypeptide Hexavalent B.3a (SEQ ID NOs: 7-8). The restriction enzyme sites and the beginning point of each M serotype immunogenic peptide are indicated. Nine Arg codons were optimized for expression in *E. coli* by mutating AGG/AGA codons to CGT/CGC codons (mutated bases are underlined).

FIGS. 4A to 4C show the nucleotide and amino acid sequence of hybrid polypeptide Hexavalent C.2 (SEQ ID NOs: 3-4). The restriction enzyme sites and the beginning point of each M serotype immunogenic peptide are indicated. Seven Arg codons were optimized for expression in *E. coli* by mutating AGG/AGA codons to CGT codons (mutated bases are underlined).

FIGS. 5A to 5C show the nucleotide and amino acid sequence of hybrid polypeptide Hexavalent D.3 (SEQ ID NOs: 5-6). The restriction enzyme sites and the beginning point of each M serotype immunogenic peptide are indicated. Five Arg codons were optimized for expression in *E. coli* by mutating AGG/AGA codons to CGT/CGC codons (mutated bases are underlined).

DETAILED DESCRIPTION OF THE INVENTION

Figure 1:
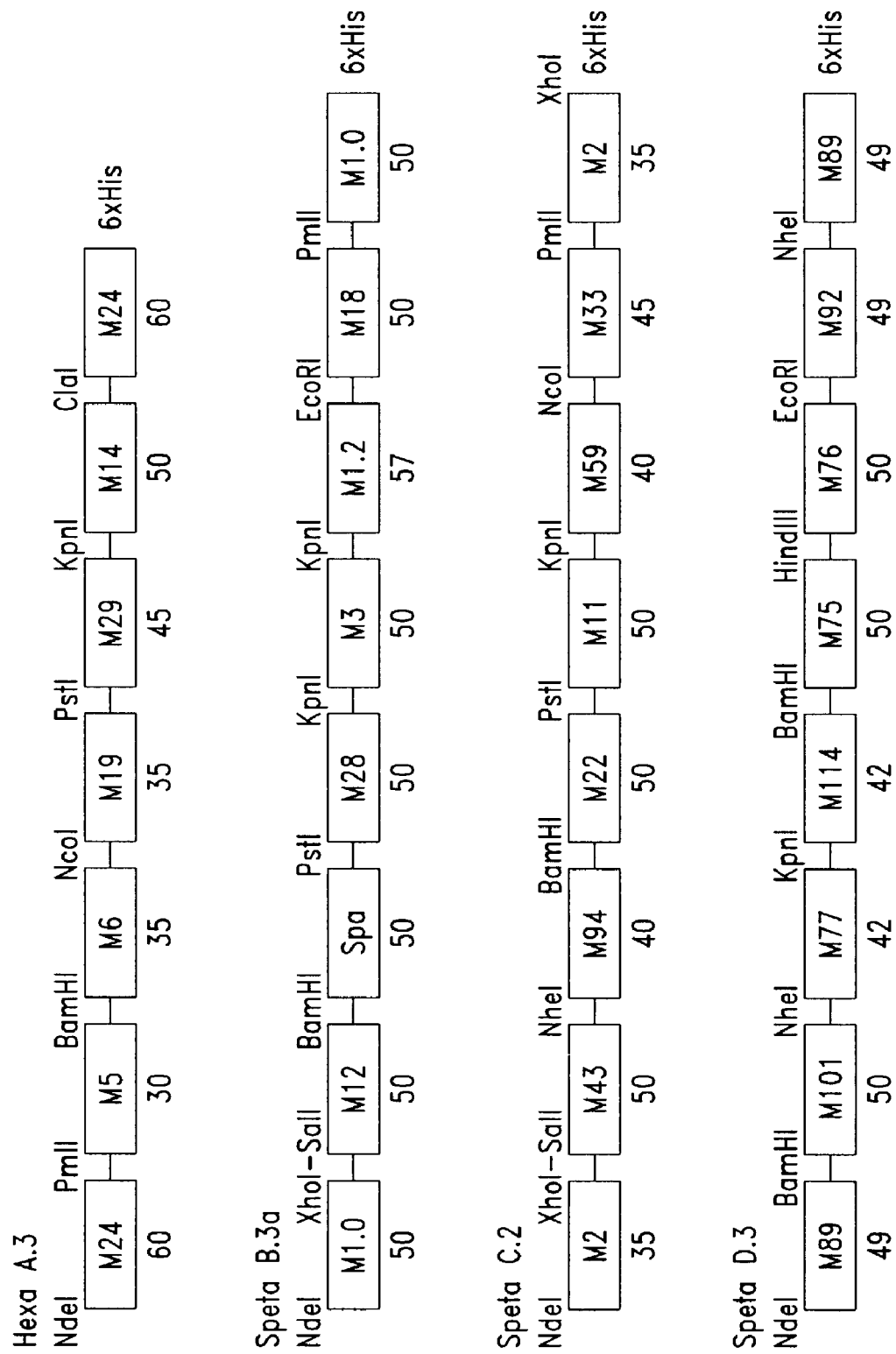
FIG. 1 shows a schematic diagram of the four hybrid polypeptides used as a vaccinating agent. The oligonucleotide primers used to amplify a 5' emm gene fragment (i.e., immunogenic peptide) by PCR for each serotype were synthesized to include the indicated unique restriction enzyme sites, which encode amino acids that link the immunogenic peptides in tandem (indicated by the lines between the boxes). Each box represents an amino-terminal M protein immunogenic peptide, wherein the number within each box designates the serotype and the number below each box indicates the number of amino acids comprising each immunogenic peptide. Serotype M101 was formerly designated stNS5, serotype M114 was formerly designated st2967, and serotype M94 was formerly designated M13W and M13. The "6xHis" refers to the presence of a hexahistidine, which is optional.
Figure 6:
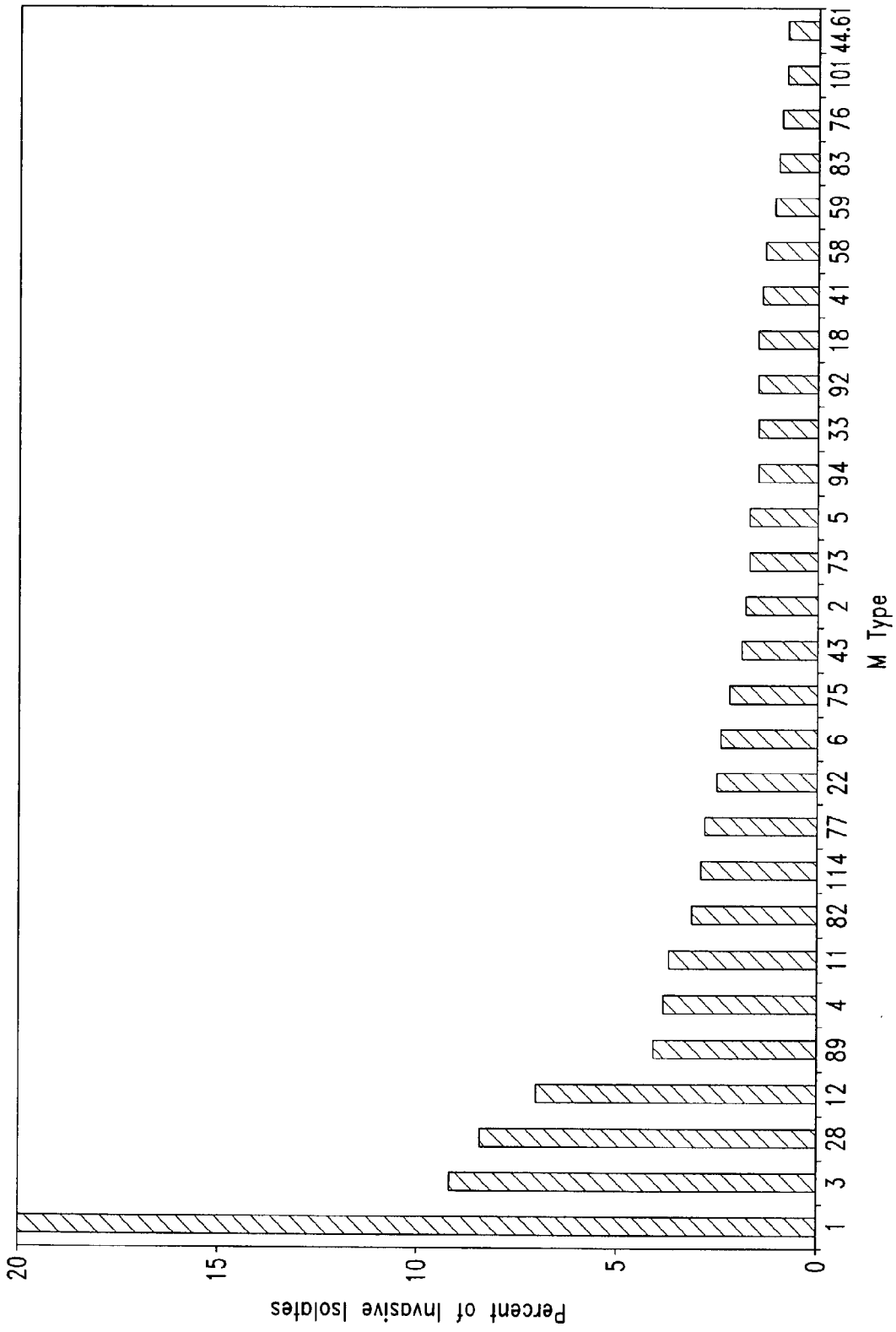
FIG. 6 shows a summary of the 28 most common invasive group A streptococci M serotypes isolated in the U.S. between Aug. 12, 2000 and Jul. 16, 2001. The data were part of ongoing studies conducted by the Active Bacterial Core Surveillance Program of the Centers for Disease Control and Prevention. These 28 serotypes accounted for 92.1% of the 3,424 invasive isolates submitted during this period.

As noted above, the present invention is generally directed to hybrid polypeptides of streptococcal antigens and compositions thereof, which are capable of eliciting protective antibodies against streptococci. Furthermore, the compositions may include a single hybrid polypeptide or a combination of several different hybrid polypeptides, which may be useful to elicit an immune response against group A streptococci. In one aspect, one or more hybrid polypeptide may be formulated as a composition for simultaneously treating or preventing an infection by several different group A streptococcal serotypes, as well as treating or preventing infection by serotypes not represented in the hybrid polypeptide(s). The present invention also provides isolated nucleic acids that encode such hybrid polypeptides, as well as methods of expressing and purifying such hybrid polypeptides. A hybrid polypeptide, as described herein, comprises several different linked immunogenic peptides wherein each peptide comprises, for example, an amino-terminal portion of a streptococcal M protein and can elicit opsonic antibodies specific for a particular group A streptococcal serotype without eliciting antibodies that are cross-reactive with host tissue.

The present invention also provides antibodies specific for each immunogenic peptide serotype included in a hybrid polypeptide or in a combination of hybrid polypeptides, as well as antibodies specific for serotypes not included in the hybrid polypeptide(s) (i.e., antibodies that confer cross-protection between serotypes). The invention, therefore, relates generally to the surprising discovery that highly complex, multivalent hybrid polypeptide-based vaccines are feasible to simultaneously elicit broadly protective antibodies against several different streptococcal serotypes. Moreover, a composition comprising a cocktail of more than one multivalent hybrid polypeptide used as a vaccine unexpectedly elicits a much more robust antibody response in humans than does a composition comprising a single multivalent hybrid polypeptide, wherein the increase in antibody response also results in an increase in antibody function (i.e., increased ability to opsonize and/or to kill microorganisms). As used herein, a "cocktail" of hybrid polypeptides refers to a composition comprising at least two different hybrid polypeptides of this invention. Hence, the invention also relates generally to the surprising discovery that a cocktail of multivalent hybrid polypeptides can function synergistically to elicit a greater antibody response that is a protective immune response. Accordingly, the compositions and methods of the present invention may be readily used to treat or prevent streptococcal infections. Discussed in more detail below are hybrid polypeptides and assorted compositions thereof (including admixtures or cocktails) suitable for use within the present invention, as well as exemplary methods of making such hybrid polypeptides and compositions, and therapeutic uses thereof.

Any numerical ranges recited herein are to be understood to include any integer within the range and, where applicable (e.g., concentrations), fractions thereof, such as one tenth and one hundredth of an integer (unless otherwise indicated).

Hybrid Polypeptides

The present invention is directed generally to multivalent immunogenic hybrid polypeptides of M proteins and M-like proteins, including fusions to other proteins. The immunogenic M and M-like peptides may comprise any portion of an M protein that is immunogenic, which may or may not confer serotype specificity. A plurality of different multivalent immunogenic hybrid polypeptides can be mixed or combined into a cocktail composition for use in eliciting a protective immune response. The present invention further provides methods for producing synthetic or recombinant multivalent immunogenic hybrid M polypeptides, including fusion proteins. For example, host cells containing hybrid polypeptide-encoding nucleic acid expression constructs may be cultured to produce recombinant hybrid polypeptides. Also contemplated are methods for treating or preventing a microbial infection or eliciting an immune response using a hybrid polypeptide or a combination of hybrid polypeptides (including fusion proteins).

By way of background and not wishing to be bound by theory, streptococcal species are Gram-positive bacteria that are grouped based on immunological differences in their cell wall polysaccharides and are designated, for example, group A, B, C, F, and G. Specifically, group A streptococci (GrAS) are clinically important microorganisms that colonize the throat and skin. GrAS are responsible for a variety of suppurative infections (e.g., strep throat, necrotizing fasciitis) and non-suppurative sequelae (e.g., acute rheumatic fever, reactive arthritis) (see generally Cunningham, *Clin. Microbiol. Rev.* 13:470, 2000). GrAS have two major, surface-exposed anti-phagocytic factors, capsule and M protein, which allow these organisms to colonize and survive in a host. The M protein, which is encoded by the emm gene, extends from the cell surface as an α-helical coiled-coil dimer that appears as a fibril on the surface of GrAS. The M proteins are a diverse group, which have been serologically separated into M protein serotypes.

Currently, more than 120 M protein serotypes have been identified, and within some serotypes there have been identified several subtypes. For example, without limitation, type 1 M protein has related subtypes 1.1-1.15, and type 12 has subtypes 12.1-12.9. In addition, as is known in the art, unclassified serotypes may have an initial designation (such as st2967) and ultimately receive a "final" classification (such as st2967 now being classified as M type 114), or previously classified serotypes may be reclassified with a different number (such as M13W is now reclassified as M94). In certain embodiments, amino-terminal portions of any one or more of known M protein from serotypes 1-120+, or from unknown serotypes, can be used to generate immunogenic peptides for inclusion in multivalent immunogenic hybrid polypeptides of the instant invention.

Furthermore, the M protein is part of a superfamily of proteins, which includes without limitation, immunoglobulin binding proteins (e.g., FrcA), M-like proteins (e.g., Mrp and Spa), and M proteins. Accordingly, as used herein, "M protein" refers to the superfamily of proteins, which includes any known or unknown M protein (with or without a designated serotype), as well as M-like proteins, such as Spa (see, e.g., Dale et al., *J. Clin. Invest.* 103:1261, 1999 and McLellan et al., *Infect. Immun.* 69:2943, 2001), Mrp (see, e.g., Boyle et al., *J. Infect. Dis.* 177:991, 1998), immunoglobulin binding proteins (see, e.g., Podbielski et al., *Mol. Microbiol.* 12:725, 1994; Whatmore and Kehoe, *Mol. Microbiol.* 11:363, 1994), and the like. As described herein and is understood in the art, the serotype of an M protein may be reclassified and result in a change to a different type, a new type, or even a subtype. Also, as used herein, "M protein serotype" or "M type" refers to all M proteins within that serotype, including all subtypes, related proteins, and the like. Furthermore, reference to a particular M type may be applied interchangeably as follows, by way of illustration and not limitation, serotype 1 M protein, type 1, M1, and the like, which as set forth above, includes all subtypes as well.

As described above, group A streptococci have developed a system for avoiding some of the antimicrobial defenses of a human host. Strains of streptococci that express capsule and M protein can evade phagocytosis by, for example, polymorphonuclear leukocytes or neutrophils and multiply in a host that has not been exposed to streptococci (i.e., have non-immune blood). Yet, a subject may develop resistance to a streptococcal infection if the host can produce protective antibodies directed against streptococci. Protection against GrAS generally correlates with the presence of opsonizing antibody against type-specific M protein (see, e.g., Lancefield, *J. Immunol.* 89:307, 1962), and the development of secretory or mucosal antibodies is suspected of playing an important role in preventing initial colonization by streptococci. However, the pathogenesis of some of the non-suppurative sequelae may be due to host tissue cross-reaction with streptococcal antibodies. As used herein, "tissue cross-reactivity" means a host antigen shares at least one epitope with a foreign antigen, such as a streptococcal antigen. For example, the different antigens may share an identical amino acid sequence, may be homologous but non-identical, or may be dissimilar molecules with a shared epitope (e.g., protein and carbohydrate or protein and nucleic acid molecule). Thus, an effective vaccine against streptococcal infections would preferably elicit an immune response that includes antibodies that are not tissue cross-reactive (i.e., do not cause autoimmune disease) and are protective (i.e., opsonic) against many of the clinically important serotypes.

The present invention pertains to hybrid polypeptides or variants thereof having a plurality of immunogenic peptides from M or M-like proteins, or nucleic acid molecules encoding such polypeptides or variants thereof. As used herein, "immunogenic peptide" refers to any streptococcal peptide or polypeptide having at least one epitope capable of eliciting an immune response, which are the component units of the hybrid polypeptides. Preferably, the epitope is within an amino-terminal portion of a streptococcal M protein or Spa protein and more preferably is an opsonic epitope that does not elicit tissue cross-reactive antibodies.

The present invention also provides a rational vaccine design approach for selection of the streptococcal M protein serotypes to be included in the multivalent hybrid polypeptide vaccine. Some criteria that may be used, without limitation, include identifying the M protein serotypes that are frequent causes of uncomplicated pharyngitis, identifying the serotypes that are commonly recovered from normally sterile sites (i.e., invasive strains) (e.g., useful data may obtained from the Active Bacterial Core Surveillance of the Emerging Infections Program Network, supported by the Centers for Disease Control and Prevention; see also Beall et al., *J. Clin. Microbiol.* 35:1231, 1997; Schuchat et al., *Emerg. Infect. Dis.* 7:92, 2001), and identifying serotypes that are considered currently or historically "rheumatogenic" (Bisno A L. The concept of rheumatogenic and non-rheumatogenic group A streptococci. In: Reed S E, and J. B. Zabriskie, ed. Streptococcal Diseases and the Immune Response. New York: Academic Press, 1980:789-803). Also useful is the amino-terminal peptide fragment of Spa, a new protective antigen that is expressed by several serotypes of group A streptococci (Dale et al., *J. Clin. Invest.* 103:1261, 1999), or any other streptococcal antigen capable of eliciting protective antibodies may be used.

As described herein and known in the art, M protein amino acid sequences selected for inclusion in a hybrid polypeptide are available at the CDC emm typing center website (see Internet at cdc.gov/ncidod/biotech/strep/emmtypes). In addition, to eliminate the possibility of eliciting tissue cross-reactive antibodies, the amino-terminal regions of a mature M protein and Spa may be compared to known human proteins to detect any homology (e.g., using BLASTP). Preferably, amino-terminal M protein portions having five or more contiguous amino acid matches with a human protein are excluded. In addition, the selected regions of the M peptides and Spa are preferably analyzed by the method of Hopp and Woods (*Mol. Immunol.* 20:483, 1983) to ensure the integrity of hydrophilic peaks. For example the Hopp and Woods method may be helpful in predicting that a particular immunogenic peptide from an M protein amino-terminal may best be fused with a certain subset of other immunogenic peptides and not with others.

In preferred embodiments, the hybrid polypeptides or variants, and combinations thereof, may be designed to be vaccines specific for streptococci associated with, for example, pharyngitis, scarlet fever, acute rheumatic fever, necrotizing faciitis, cellulitis, meningitis, pneumonia, toxic shock syndrome, bacteremia, septicemia, septic arthritis, pyoderma, skin infections, impetigo, erysipelas, soft-tissue infection, nephritis, pyrogenic reactions, and the like. Additionally, the vaccines may be designed to treat or prevent streptococcal infections in particular populations (e.g., immunocompromised patients, children, and elderly) particular geographic populations (e.g., Australian aborigines), and particular geographic locations (e.g., temperate regions or Scandinavian countries). Preferably, the amino-terminal portions of the different M proteins that comprise an immunogenic peptide can elicit opsonic antibodies that do not cross-react with host tissue.

In another preferred aspect, the M protein serotype is selected based on its prevalence on the most common streptococci known to currently be associated with a particular disease (e.g., serotypes associated with pharyngitis or skin infections) or sequelae. In a further preferred aspect, the instant invention may be used to design and generate a variety of different multivalent immunogenic hybrid polypeptides that may be directed to, or be admixed in particular groupings to address, shifts in prevalent streptococci. For example, as is known in the art, the most prevalent streptococci serotype associated with a disease today, such as ARF, may not be as prevalent or important 5, 10, or 15 years. In another example, a particular streptococcal serotype may be prevalent in Europe and suddenly become important in South America. Hence the immunogenic peptides that comprise a multivalent hybrid polypeptide may be changed, or different multivalent hybrid polypeptides may be mixed and matched to create a desired cocktail, designed for use in a particular population or location to attack the most clinically relevant streptococci as needed.

In certain preferred embodiments, an immunogenic peptide comprises an amino-terminal portion of a M protein or Spa protein having 10-70 amino acids, or any integer in that range; more preferably having 20-65 amino acids, or any integer in that range; and most preferably 30-60 amino acids, or any integer in that range. In particularly preferred embodiments, a hybrid polypeptide comprises at least six or seven different linked immunogenic peptides, wherein each peptide comprises an amino-terminal portion of a streptococcal M protein of at least 30 amino acids, and wherein the polypeptide has an amino-terminal peptide that is reiterated as a carboxy-terminal peptide and the polypeptide is capable of eliciting an immune response against more than one serotype of group A streptococci. Preferably, a hybrid polypeptide is capable of eliciting an immune response against at least serotypes 5, 6, 14, 19, 24, and 29; or at least against serotypes 2, 11, 22, 33, 43, 59, and 94; or at least against serotypes 75, 76, 77, 89, 92, 101, and 114; or at least against serotypes 1.0, 1.2, 3, 12, 18, and 28. In another preferred embodiment, a hybrid polypeptide is capable of eliciting an immune response against a M serotype not represented in the hybrid polypeptide, such as serotype 4.

In certain embodiments, the hybrid polypeptides have at least 50% to 100% amino acid identity, or any integer in that range, to the amino acid sequence as set forth in SEQ ID NOS:2, 4, 6, and 8; preferably 60%-99% identity or any integer in that range, more preferably 70%-97% identity or any integer in that range, and most preferably 80%-95% identity or any integer in that range. As used herein, "percent identity" or "% identity" is the percentage value returned by comparing the whole of the subject polypeptide, peptide, or variant thereof sequence to a test sequence using a computer implemented algorithm, typically with default parameters. Sequence comparisons can be performed using any standard software program, such as BLAST, tBLAST, pBLAST, or MegAlign. Still others include those provided in the Lasergene bioinformatics computing suite, which is produced by DNASTAR® (Madison, Wis.). References for algorithms such as ALIGN or BLAST may be found in, for example, Altschul, *J. Mol. Biol.* 219:555-565, 1991; or Henikoff and Henikoff, Proc. Natl. Acad. Sci. USA 89:10915-10919, 1992. BLAST is available at the NCBI website (see Internet at ncbi.nlm.nih.gov/BLAST). Other methods for comparing multiple nucleotide or amino acid sequences by determining optimal alignment are well known to those of skill in the art (see, e.g., Peruski and Peruski, *The Internet and the New Biology: Tools for Genomic and Molecular Research* (ASM Press, Inc. 1997); Wu et al. (eds.), "Information Superhighway and Computer Databases of Nucleic Acids and Proteins," in Methods in Gene Biotechnology, pages 123-151 (CRC Press, Inc. 1997); and Bishop (ed.), Guide to Human Genome Computing, 2nd Edition, Academic Press, Inc., 1998). As used herein, "similarity" between two peptides or polypeptides is generally determined by comparing the amino acid sequence of one peptide or polypeptide to the amino acid sequence and conserved amino acid substitutes thereto of a second peptide or polypeptide. Fragments or portions of the hybrid polypeptides of the present invention may be employed for producing the corresponding full-length hybrid polypeptide by peptide synthesis; therefore, the fragments may be employed as intermediates for producing the full-length hybrid polypeptides. Similarly, fragments or portions of the nucleic acids of the present invention may be used to synthesize full-length nucleic acids of the present invention.

The hybrid polypeptides and corresponding nucleic acids of the present invention are preferably provided in an isolated form, and in certain preferred embodiments, are purified to homogeneity. As used herein, the term "isolated" means that the material is removed from its original or natural environment. For example, a naturally occurring nucleic acid molecule or polypeptide present in a living animal or cell is not isolated, but the same nucleic acid molecule or polypeptide is isolated when separated from some or all of the co-existing materials in the natural system. The nucleic acid molecules, for example, could be part of a vector and/or such nucleic acids or polypeptides could be part of a composition and still be isolated in that such vector or composition is not part of its natural environment.

The present invention also pertains to hybrid polypeptides and variants thereof produced synthetically or recombinantly, and preferably recombinantly. The immunogenic peptide components of the hybrid polypeptides may be synthesized by standard chemical methods, including synthesis by automated procedure. In general, immunogenic peptides are synthesized based on the standard solid-phase Fmoc protection strategy with HATU as the coupling agent. The immunogenic peptide is cleaved from the solid-phase resin with trifluoroacetic acid containing appropriate scavengers, which also deprotects side chain functional groups. Crude immunogenic peptide is further purified using preparative reversed-phase chromatography. Other purification methods, such as partition chromatography, gel filtration, gel electrophoresis, or ion-exchange chromatography may be used. Other synthesis techniques known in the art may be employed to produce similar immunogenic peptides, such as the tBoc protection strategy, use of different coupling reagents, and the like. In addition, any naturally occurring amino acid or derivative thereof may be used, including D- or L-amino acids and combinations thereof. In particularly preferred embodiments, a synthetic hybrid polypeptide of the invention will have a M2, M12, M24, or M89 immunogenic peptide at the amino-terminus.

As described herein, the hybrid polypeptides of the invention may be recombinant, wherein the hybrid polypeptide is expressed from a polynucleotide encoding a desired hybrid polypeptide that is operably linked to an expression control sequence (e.g., promoter) in a nucleic acid expression construct. In particularly preferred embodiments, a recombinant hybrid polypeptide of the invention will have a M2, M12, M24, or M89 immunogenic peptide at the amino-terminus. Some preferable recombinant hybrid polypeptides comprise immunogenic peptides linked in tandem having the structure of M24-M5-M6-M19-M29-M14-M24, M2-M43-M94-M22-M 11-M59-M33-M 2, M89-M101-M77-M114-M75-M76-M92-M89, or M1.0-M12-Spa-M28-M3-M1.2-M18-M1.0, and any combination thereof. Most preferably, a hybrid polypeptide comprises the amino acid sequence of SEQ ID NOS:2, 4, 6, or 8, and variants thereof. As set forth above and herein, any M serotype may be included in the present invention, preferably serotypes 1.0, 1.2, 2, 3, 5, 6, 11, 12, 14, 18, 19, 22, 24, 28, 29, 33, 43, 59, 75, 76, 77, 89, 92, 94, 101, and 114 are included in the hybrid polypeptides. In certain preferred embodiments as described herein, hybrid polypeptides of the subject invention capable of eliciting at least one opsonic antibody that is not a tissue cross-reactive antibody in a subject, wherein the subject is an animal or a human.

In another preferred embodiment, the hybrid polypeptides are linked by at least two amino acids encoded by a nucleic acid sequence that is a restriction enzyme recognition site, wherein the restriction sites may be any one or more of BamHI, ClaI, EcoRI, HindIII, KpnI, NcoI, NheI, PmlI, PstI, SalI, XhoI, and the like. Additional amino acid linkers may also be added synthetically as described herein. Preferably, the additional amino acids do not create any identity in sequence within a five amino acid stretch of a human protein. In addition, the hybrid polypeptides of the subject invention may further comprise at least one additional carboxy-terminal amino acid, wherein the additional amino acid is a D- or an L-amino acid. Any of the twenty naturally occurring amino acids or derivatives thereof may be added, such as cysteine, histidine, leucine, and glutamic acid. For example, the addition of cysteine may be useful to attach other constituents, such as a lipid, a carrier protein, and the like.

As described herein, the invention also provides hybrid polypeptide fusion proteins comprising hybrid polypeptides fused to an additional functional or non-functional polypeptide sequence that permits, for example by way of illustration and not limitation, detection, isolation and/or purification of the hybrid polypeptide fusion proteins. For instance, an additional functional polypeptide sequence may be a tag sequence, which includes fusion proteins that may in certain embodiments be detected, isolated and/or purified by protein-protein affinity (e.g., receptor-ligand), metal affinity or charge affinity methods. In certain other embodiments the hybrid polypeptide fusion proteins may be detected by specific protease cleavage of a fusion protein having a sequence that comprises a protease recognition sequence, such that the hybrid polypeptides may be separable from the additional polypeptide sequence. In addition, the hybrid polypeptides may be made synthetically including additional amino acids, a carrier protein, or a tag sequence, which may be located at either the amino- or carboxy-terminal end. In particularly preferred embodiments, for example, recombinant hybrid polypeptides are fused in-frame to a carboxy-terminal tag, which tag may be any one of alkaline phosphatase, β-galactosidase, hexahistidine (6×His), FLAG® epitope tag (DYKDDDDK, SEQ ID NO:18), or GST, and the like. Most preferred are hybrid polypeptide fusion proteins that facilitate affinity detection and isolation of the hybrid polypeptides and may include, for example, poly-His or the defined antigenic peptide epitopes described in U.S. Pat. No. 5,011,912 and in Hopp et al., (1988 *Bio/Technology* 6:1204), or the XPRESS™ epitope tag (DLYDDDDK, SEQ ID NO:19; Invitrogen, Carlsbad, Calif.). The affinity sequence may be a hexa-histidine tag as supplied by a vector. For example, a pBAD/His (Invitrogen) or a pQE-30 (Qiagen, Valencia, Calif.) vector can provide a polyhistidine tag for purification of the mature protein fusion from a particular host, such as a bacterium. Alternatively, the affinity sequence may be added either synthetically or engineered into the primers used to recombinantly generate the nucleic acid sequence (e.g., using the polymerase chain reaction) encoding an immunogenic peptide of the multivalent hybrid polypeptide. Preferably, a multivalent hybrid polypeptide is fused to a polyhistidine and is encoded by a recombinant nucleic acid sequence encoding such a fusion protein.

The immunogenic peptides may also be chemically linked to form the desired hybrid polypeptides, including additional amino acid sequences, by a variety of methods, as provided herein and known in the art (see, generally, Jackson et al., *Vaccine* 18:355, 2000). Recombinant or synthetic peptides may be linked to form linear (see, e.g., Leclerc, et al., *Eur. J. Immunol.* 17:26, 1987 and Francis, et al., *Nature* 330:168, 1987) or branched (see, e.g., Fitzmaurice, et al., *Vaccine* 14:553, 1996) constructs, or may be linked using chemical ligation of epitopes (see, e.g., Tam and Spetzler, *Biomed. Pept. Proteins Nucleic Acids* 1:123, 1995; Rose, *J. Am. Chem. Soc.* 116:30, 1994; and Dawson, et al., *Science* 266:776, 1994). Peptides may also be linked via the multiple antigen peptide system to form branched hybrid polypeptides (see, e.g., Tam, *Proc. Natl. Acad. Sci. USA* 85:5409, 1988; U.S. Pat. No. 5,229,490). The multiple antigen peptide system makes use of multifunctional core molecules where each functional group on the core molecule forms at least two branches, the principal units of which are also multifunctional. For example, lysine may be used as the core peptide because it has one carboxyl functional group and two (α and ε) amine functional groups. Each multifunctional unit in a branch provides a base for added growth, resulting in exponential growth of the dendritic polymer. Peptides may then be joined to the dendritic core using a linking molecule (e.g., glycine). The multiple antigen peptide system links a large number of synthetic peptides to the functional group of a dendritic core molecule providing a high concentration of synthetic peptides in a low molecular volume. Preferably, either two or three levels of geometrically branched lysines are used, wherein these lysine cores form a tetrameric and octameric core structure, respectively. The multiple antigen peptide system may also include a lipophilic anchoring moiety attached to the core molecule, thereby eliminating the need for an adjuvant formulated in a peptide vaccine otherwise requiring one for immunostimulation (see, e.g., U.S. Pat. No. 5,580,563). In one preferred embodiment, a hybrid polypeptide of the invention comprises immunogenic peptides linked to form a lysine core-branched polypeptide.

Additionally, similar or different synthetic peptides may be linked by controlled polymerization through derivatization of the amino-terminus of a peptide with the acryloyl ($CH_2{=}CH{-}$) group using acryloyl chloride (see, e.g., O'Brien-Simpson, et al., *J. Am. Chem. Soc.* 119:1183, 1997;

Jackson, et al., *Vaccine* 15:1697, 1997). The derivatized peptides are then polymerized singly, or in admixture with similarly derivatized peptides, by free radical initiation of chain elongation. As a result, peptides are assembled into polymers in which the peptide determinants form side chains pendant from an alkane backbone. The hybrid polypeptides and fusion proteins as described herein may be constructed as set forth above. In one preferred embodiment, a hybrid polypeptide of the invention comprises immunogenic peptides linked by an alkane backbone. In certain embodiments, the alkane backbone is acrylamide or an analog or derivative thereof.

Therapeutic Formulations and Methods of Use

The invention also relates to pharmaceutical compositions that contain one or more hybrid multivalent polypeptides, which may be used to elicit an immune response. The invention further relates to methods for treating and preventing microbial infections by administering to a subject a hybrid polypeptide or a mixture of hybrid polypeptides at a dose sufficient to elicit antibodies specific for one or more hybrid polypeptide, as described herein. A hybrid polypeptide or a cocktail of hybrid polypeptides is preferably part of a pharmaceutical composition when used in the methods of the present invention.

In certain aspects, the invention provides a composition comprising a pharmaceutically acceptable carrier, diluent, or excipient, and any of the multivalent hybrid polypeptides of the subject invention and any combination thereof. A preferred embodiment is a pharmaceutically acceptable carrier and a mixture of at least two or three hybrid polypeptides of the subject invention. In yet another preferred embodiment, a hybrid polypeptide that comprises at least seven different immunogenic peptides linked in tandem, wherein each peptide comprises an amino-terminal portion of a streptococcal M protein of at least 50 amino acids, and wherein the polypeptide has an amino-terminal peptide that is reiterated as a carboxy-terminal peptide and the polypeptide is capable of eliciting an immune response against more than one serotype of group A streptococci comprising at least serotypes 1.0, 1.2, 3, 12, 18, and 28, is combined with at least one other hybrid polypeptide of the subject invention and a pharmaceutically acceptable carrier. In a more preferred embodiment, a composition comprises a pharmaceutically acceptable carrier and a mixture of the hybrid polypeptides of SEQ ID NOS:2, 4, 6, and 8 or variants thereof, and in other embodiment these four polypeptides or variants thereof are mixed in equimolar amounts and at least one of the hybrid polypeptides has a Spa peptide. In other embodiments, SEQ ID NOS:2, 4, 6, and 8 or variants thereof are provided with a polyhistidine tag or further comprise at least one additional amino acid, such as cysteine. Each of these formulations may further comprise an adjuvant, such as alum or Freund's, and a diluent such as water or PBS. Further, therapeutic compositions of the present invention should preferably be stable for several months and capable of being produced and maintained under sterile conditions.

The pharmaceutical composition will include at least one of a pharmaceutically acceptable vehicle, carrier, diluent, or excipient, in addition to one or more hybrid multivalent polypeptide or fusion protein thereof and, optionally, other components. For example, pharmaceutically acceptable carriers suitable for use with a composition of a hybrid polypeptide or fusion protein thereof, or cocktail of two or more hybrid polypeptide or fusion protein thereof, may include, for example, a thickening agent, a buffering agent, a solvent, a humectant, a preservative, a chelating agent, an adjuvant, and the like, and combinations thereof. Exemplary adjuvants are alum (aluminum hydroxide, REHYDPAGEL®), aluminum phosphate, proteosome adjuvant (see, e.g., U.S. Pat. Nos. 5,726,292 and 5,985,284), virosomes, liposomes with and without lipid A, DETOX® (Ribi/Corixa), MF59, or other oil and water emulsions type adjuvants, such as nanoemulsions (see, e.g, U.S. Pat. No. 5,716,637) and submicron emulsions (see, e.g., U.S. Pat. No. 5,961,970), and Freund's complete and incomplete. Pharmaceutically acceptable carriers for therapeutic use are well known in the pharmaceutical art, and as described herein and, for example, in *Remington's Pharmaceutical Sciences*, Mack Publishing Co. (A. R. Gennaro, ed., 18$^{th}$ Edition, 1990) and in *CRC Handbook of Food, Drug, and Cosmetic Excipients*, CRC Press LLC (S. C. Smolinski, ed., 1992).

"Pharmaceutically acceptable salt" refers to salts of the compounds of the present invention derived from the combination of such compounds and an organic or inorganic acid (acid addition salts) or an organic or inorganic base (base addition salts). The compounds of the present invention may be used in either the free base or salt forms, with both forms being considered as being within the scope of the present invention.

In addition, the pharmaceutical composition may further include a diluent such as water or phosphate buffered saline (PBS). Preferably, diluent is PBS with a final phosphate concentration ranges from about 0.1 mM to about 1 M, more preferably from about 0.5 mM to about 500 mM, even more preferably from about 1 mM to about 50 mM, and most preferably from about 2.5 mM to about 10 mM; and the final salt concentration ranges from about 100 mM to about 200 mM and most preferably from about 125 mM to about 175 mM. Preferably, the final PBS concentration is about 5 mM phosphate and about 150 mM salt (such as NaCl). In certain embodiments, any of the aforementioned pharmaceutical compositions comprising a cocktail of multivalent hybrid polypeptides of the instant invention are preferably sterile.

The compositions can be sterile either by preparing them under an aseptic environment and/or they can be terminally sterilized using methods available in the art. Many pharmaceuticals are manufactured to be sterile and this criterion is defined by the USP XXII <1211>. Sterilization in this embodiment may be accomplished by a number of means accepted in the industry and listed in the USP XXII <1211>, including gas sterilization, ionizing radiation or filtration. Sterilization may be maintained by what is termed aseptic processing, defined also in USP XXII <1211>. Acceptable gases used for gas sterilization include ethylene oxide. Acceptable radiation types used for ionizing radiation methods include gamma, for instance from a cobalt 60 source and electron beam. A typical dose of gamma radiation is 2.5 MRad. When appropriate, filtration may be accomplished using a filter with suitable pore size, for example 0.22 µm and of a suitable material, for instance TEFLON®. The term "USP" refers to U.S. Pharmacopeia (see the USP website: usp.org; Rockville, Md.).

The present invention also pertains to methods for preventing a microbial infection, comprising administering to a subject a composition of the subject invention at a dose sufficient to elicit antibodies specific for one or more hybrid polypeptide, wherein the antibodies are preferably opsonic and are not tissue cross-reactive. In certain embodiments an infection is a streptococcal infection, such as a group A streptococcal infection. A subject suitable for treatment with a hybrid polypeptide formulation may be identified by well-established indicators of risk for developing a disease or well-established hallmarks of an existing disease. For example, indicators of an infection include fever, pus, microorganism positive cultures, inflammation, and the like. Infections that may be treated with a hybrid polypeptide of the subject invention include, without limitation, those caused by or due to microorganisms, whether the infection is primary, secondary, opportunistic, or the like. Examples of microorganisms include Gram-positive bacteria, such as streptococci.

The pharmaceutical compositions that contain one or more hybrid polypeptides may be in any form that allows for the composition to be administered to a subject, such as a human or animal. For example, multivalent hybrid polypeptide compositions of the present invention may be prepared and administered as a liquid solution or prepared as a solid form (e.g., lyophilized), which may be administered in solid form, or resuspended in a solution in conjunction with administration. The hybrid polypeptide composition is formulated so as to allow the active ingredients contained therein to be bioavailable upon administration of the composition to a subject or patient or bioavailable via slow release. Compositions that will be administered to a subject or patient take the form of one or more dosage units, where for example, a tablet may be a single dosage unit, and a container of one or more compounds of the invention in aerosol form may hold a plurality of dosage units. In certain preferred embodiments, any of the aforementioned pharmaceutical compositions comprising a hybrid polypeptide or cocktail of hybrid polypeptides of the invention are in a container, preferably in a sterile container.

In one embodiment, the therapeutic composition is administered orally, and a hybrid polypeptide or cocktail composition of the invention is taken up by cells, such as cells located in the lumen of the gut. Other typical routes of administration include, without limitation, enteral, parenteral, transdermal/transmucosal, and inhalation. The term enteral, as used herein, is a route of administration in which the agent is absorbed through the gastrointestinal tract or oral mucosa, including oral, rectal, and sublingual. The term parenteral, as used herein, describes administration routes that bypass the gastrointestinal tract, including intraarterial, intradermal, intramuscular, intranasal, intraocular, intraperitoneal, intravenous, subcutaneous, submucosal, and intravaginal injection or infusion techniques. The term transdermal/transmucosal, as used herein, is a route of administration in which the agent is administered through or by way of the skin, including topical. The term inhalation encompasses techniques of administration in which an agent is introduced into the pulmonary tree, including intrapulmonary or transpulmonary. Preferably, the compositions of the present invention are administered intramuscularly.

Depending upon the application, the dose of hybrid polypeptide in the compositions will vary, generally, from about 10 µg to about 10 mg, preferably from about 100 µg to 1 mg, more preferably from about 150 µg to 500 µg, and most preferably from about 200 µg to about 400 µg, in combination with the biologically acceptable excipient, adjuvant, binder, and/or diluent, including any integer with the dosing range. As used herein, the term "about" or "consists essentially of" refers to ±10% of any indicated structure, value, or range. Booster immunizations may be given at multiple times, at desired intervals ranging from about 2 weeks to about 24 weeks, preferably 2, 4 and 8 week intervals, and more preferably 2, 4, and 16 week intervals, and even more preferably 0, 4, and 24 week intervals to maximize the immune response.

The invention further provides a plurality of antibodies produced by the method for preventing a microbial infection that comprises administering to a subject a composition of the subject invention at a dose sufficient to elicit antibodies specific for one or more hybrid polypeptide, wherein the antibodies are opsonic and are not tissue cross-reactive. In one embodiment, the antibodies comprise at least one antibody specific for a M serotype not represented in a hybrid polypeptide, such as type 4 M protein. In another embodiment, a method for treating or preventing a microbial infection comprises administering to a subject a composition comprising a pharmaceutically acceptable carrier and a plurality of antibodies of the subject invention.

Antibodies and Assays

In another aspect, the hybrid polypeptides and variants thereof of the present invention are utilized to elicit antibodies specific for at least one epitope present on the hybrid polypeptides provided herein. Accordingly, the present invention also provides such antibodies. In preferred embodiments the antibodies bind to specific protective epitopes present on a M protein. Within the context of the present invention, the term "antibodies" includes polyclonal antibodies, monospecific antibodies, monoclonal antibodies, anti-idiotypic antibodies, fragments thereof such as $F(ab')_2$ and Fab fragments, and recombinantly or synthetically produced antibodies. Such antibodies incorporate the variable regions that permit a monoclonal antibody to specifically bind, which means an antibody is able to selectively bind to a peptide produced from an emm or spa sequence of this invention. "Specific for" refers to the ability of a protein (e.g., an antibody) to selectively bind a polypeptide or peptide encoded by an emm or spa nucleic acid molecule or a synthesized hybrid polypeptide of this invention. Association or "binding" of an antibody to a specific antigen generally involve electrostatic interactions, hydrogen bonding, Van der Waals interactions, and hydrophobic interactions. Any one of these or any combination thereof can play a role in the binding between an antibody and its antigen. Such an antibody generally associates with an antigen, such as M protein, with an affinity constant ($K_a$) of at least $10^4$, preferably at least $10^5$, more preferably at least $10^6$, still more preferably at least $10^7$ and most preferably at least $10^8$. Affinity constants may be determined by one of ordinary skill in the art using well-known techniques (see Scatchard, *Ann. N.Y. Acad. Sci.* 51:660-672, 1949). The affinity of a monoclonal antibody or antibody can be readily determined by one of ordinary skill in the art (see Scatchard, *Ann. N.Y. Acad. Sci.* 51:660-672, 1949).

In addition, the term "antibody," as used herein, includes naturally occurring antibodies as well as non-naturally occurring antibodies, including, for example, single chain antibodies, chimeric, bifunctional and humanized antibodies, as well as antigen-binding fragments thereof. Such non-naturally occurring antibodies may be constructed using solid phase peptide synthesis, may be produced recombinantly, or may be obtained, for example, by screening combinatorial libraries consisting of variable heavy chains and variable light chains (Huse et al., *Science* 246:1275-1281 (1989)). These and other methods of making, for example, chimeric, humanized, CDR-grafted, single chain, and bifunctional antibodies are well known in the art (Winter and Harris, *Immunol. Today* 14:243, 1993; Ward et al., *Nature* 341:544, 1989; Harlow and Lane, *Antibodies: A Laboratory Manual*, Cold Spring Harbor Laboratory, New York, 1992; Borrabeck, *Antibody Engineering*, 2d ed., Oxford Univ. Press, 1995; Hilyard et al., *Protein Engineering: A practical approach,* IRL Press, 1992).

In a preferred embodiment, a plurality of antibodies comprises two or more different antibodies wherein each antibody is specific for a different immunogenic peptide of a hybrid polypeptide, the polypeptide comprises at least six different immunogenic peptides linked in tandem, each peptide comprises at least 30 amino acids and the amino-terminal peptide is reiterated as a carboxy-terminal peptide, wherein the polypeptide is capable of eliciting an immune response against more than one serotype of group A streptococci. Preferably, a hybrid polypeptide is capable of eliciting an immune response against at least serotypes 5, 6, 14, 19, 24, and 29; or at least against serotypes 2, 11, 22, 33, 43, 59, and 94; or at least against serotypes 75, 76, 77, 89, 92, 101, and 114; or at least against serotypes 1.0, 1.2, 3, 12, 18, and 28. In another preferred embodiment, a hybrid polypeptide is capable of eliciting an immune response against a M serotype not represented in the hybrid polypeptide, such as serotype 4. More preferably the antibodies are elicited by the hybrid polypeptides of SEQ ID NOS:2, 4, 6, and 8, individually or in combination, and most preferably at least one antibody is opsonic and not tissue cross-reactive in a subject. As used herein, "opsonic" means any epitope that enhances phagocytosis of a cell or particle having the epitope. As commonly understood by those having ordinary skill in the art, "opsonic antibodies" are antibodies that facilitate phagocytic activity of a particle having the antigen, such as a bacterial cell. In yet another preferred embodiment, the antibodies elicited by the hybrid polypeptides of the invention are polyclonal.

Polyclonal antibodies can be readily generated by one of ordinary skill in the art from a variety of warm-blooded animals such as horses, cows, goats, sheep, dogs, chickens, turkeys, rabbits, mice, or rats. Briefly, the desired hybrid polypeptide or mixtures of hybrid polypeptides, or variants thereof are administered to immunize an animal through parenteral, intraperitoneal, intramuscular, intraocular, or subcutaneous injections. The immunogenicity of the hybrid polypeptide of interest may be increased through the use of an adjuvant, such as alum and Freund's complete or incomplete adjuvant. Following several booster immunizations over a period of weeks, small samples of serum are collected and tested for reactivity to the desired M peptide or Spa peptide. Particularly preferred polyclonal immune sera give a signal that is at least three times greater than background. Once the titer of the animal has reached a plateau in terms of its reactivity to the hybrid polypeptide, larger quantities of polyclonal immune sera may be readily obtained either by weekly bleedings or by exsanguinating the animal.

For example, the hybrid polypeptides of SEQ ID NOS:2, 4, 6, and 8 (see FIG. 1) were purified, mixed in equimolar concentrations, and formulated with alum to contain 400 µg total protein and 750 µg alum in each 0.5 ml dose. Three rabbits each received three intramuscular injections of the hybrid polypeptide cocktail at either 0, 4, and 8 weeks or 0, 4, and 16 weeks, and immune serum was recovered at 18 weeks. The harvested sera were analyzed by ELISA, as described herein, using the purified recombinant dimeric peptide components of each of the larger vaccine polypeptides. Using ELISA (with purified recombinant dimeric immunogenic peptides of the hybrid molecule), the immune sera from rabbits immunized at 0, 4, and 16 weeks were found to contain high titers of antibodies against the vast majority of the M peptides and the Spa peptide contained in the hybrid polypeptides of the cocktail (FIG. 3). In certain preferred embodiments, the polyclonal antibodies include those that are specific for group A streptococci of serotypes 5, 6, 14, 19, 24, and 29, or of serotypes 2, 11, 22, 33, 43, 59, and 94, or of serotypes 75, 76, 77, 89, 92, 101, and 114, or of serotypes 1.0, 1.2, 3, 12, 18, and 28.

Monoclonal antibodies may also be readily generated using well-known techniques (see U.S. Pat. Nos. RE 32,011, 4,902,614, 4,543,439, and 4,411,993; see also *Monoclonal Antibodies, Hybridomas: A New Dimension in Biological Analyses,* Plenum Press, Kennett, McKearn, and Bechtol (eds.), 1980, and *Antibodies: A Laboratory Manual,* Harlow and Lane (eds.), Cold Spring Harbor Laboratory Press, 1988). Briefly, in one embodiment, a subject animal such as a rat or mouse is injected with a desired protein or peptide. If desired, various techniques may be utilized in order to increase the resultant immune response generated by the protein, in order to develop greater antibody reactivity. For example, the desired protein or peptide may be coupled to another carrier protein (such as ovalbumin, keyhole limpet hemocyanin (KLH), or *E. coli* labile toxin B subunit) or through the use of adjuvants (such as alum or Freund's complete and incomplete adjuvant) and the like.

Once suitable antibodies have been obtained, they may be isolated or purified by many techniques well known to those of ordinary skill in the art (see *Antibodies: A Laboratory Manual,* Harlow and Lane, supra). Suitable techniques include peptide or protein affinity columns, HPLC or RP-HPLC, purification on protein A or protein G columns, or any combination of these techniques. Within the context of the present invention, the term "isolated" as used to define antibodies or antibodies means "substantially free of other blood components."

Several assays are available as described herein to examine the activity of the antibodies elicited by the hybrid polypeptides of the subject invention. An exemplary assay is an opsonophagocytosis assay, which detects phagocytosis facilitated by the presence of opsonic antibodies present in test antisera. Briefly, the assay measures the amount of phagocytosis of selected bacterial cells by neutrophils after preincubating the cells in the presence or absence of antisera raised against, for example, hybrid polypeptide immunogens. Preincubation with the immune sera coats the cells with M protein reactive antibodies, some of which will be opsonic antibodies elicited from opsonic epitopes present on the M protein antigens. Preincubated, coated cells are then mixed with whole blood from an animal, typically a mammal for which opsonic protection is to be sought (e.g., a human) to determine the percentage of neutrophils that associate with the bacterial cells, which is a measure of phagocytic activity facilitated by opsonic antibodies. Immune sera containing opsonic antibodies induce a higher percentage of neutrophils associated with the selected bacteria than does immune sera lacking opsonic antibodies. In a variation of this test, the bactericidal activity of immune sera may be tested by incubating the immune sera with fewer bacterial cells, incubating in blood for a longer period of time, and then plating the mixture on a culture medium to score for viable bacteria. The presence of opsonic antibodies in the immune sera increase the number of bacteria destroyed by phagocytosis and, therefore, lowers the number of colony forming units (CFUs) detected on the plate culture. Another exemplary assay analyzes bactericidal activity of the test antibodies (see Example 5).

Nucleic Acid Molecules and Host Cells

The invention also encompasses isolated nucleic acid molecules comprising a sequence encoding a hybrid polypeptide wherein each peptide comprises an amino-terminal portion of a streptococcal M protein (e.g., SEQ ID NOS:2, 4, 6, 8, 10, 12, 14, or 16). Also provided by the present invention are nucleic acid expression constructs, and host cells containing such nucleic acids, which encode hybrid polypeptide and variants thereof, which hybrid polypeptides are capable of eliciting an immune response against more than one serotype of group A streptococci. This aspect of the invention pertains to isolated nucleic acid sequences encoding a hybrid polypeptide sequence as described herein, as well as those sequences readily derived from isolated nucleic acid molecules such as, for example, complementary sequences, reverse sequences and complements of reverse sequences.

"Nucleic acid" or "nucleic acid molecule" refers to any of deoxyribonucleic acid (DNA), ribonucleic acid (RNA), oligonucleotides, fragments generated by the polymerase chain reaction (PCR), and fragments generated by any of ligation, scission, endonuclease action, and exonuclease action. Nucleic acids may be composed of monomers that are naturally occurring nucleotides (such as deoxyribonucleotides and ribonucleotides), analogs of naturally occurring nucleotides (e.g., α-enantiomeric forms of naturally-occurring nucleotides), or a combination of both. Modified nucleotides can have modifications in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety may be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. The term "nucleic acid" also includes so-called "peptide nucleic acids," which comprise naturally occurring or modified nucleic acid bases attached to a polyamide backbone. Nucleic acids can be either single stranded or double stranded.

Further, an "isolated nucleic acid molecule" refers to a polynucleotide molecule in the form of a separate fragment or as a component of a larger nucleic acid construct, which has been separated from its source cell (including the chromosome it normally resides in) at least once in a substantially pure form. For example, a DNA molecule that encodes a Spa polypeptide, peptide, or variant thereof, which has been separated from a Streptococcus cell or from the genomic DNA of a Streptococcus cell, is an isolated DNA molecule. Another example of an isolated nucleic acid molecule is a chemically synthesized nucleic acid molecule. Nucleic acid molecules may be comprised of a wide variety of nucleotides, including DNA, cDNA, RNA, nucleotide analogues, or some combination thereof. In one preferred embodiment, an isolated nucleic acid molecule comprises a sequence encoding a hybrid polypeptide of SEQ ID NOS:2, 4, 6, 8, 10, 12, 14, or 16.

In certain aspects, the invention relates to nucleic acid vectors and constructs that include nucleic acid sequences of the present invention, and in particular to "nucleic acid expression constructs" that include any polynucleotide encoding a hybrid polypeptide as provided above; to host cells that are genetically engineered with vectors and/or constructs of the invention and to the production and use in methods for treating or preventing a microbial infection or eliciting an immune response. The hybrid polypeptides may be expressed in mammalian cells, yeast, bacteria or other cells under the control of appropriate expression control sequences. Cell-free translation systems may also be employed to produce such proteins using RNAs derived from the nucleic acid expression constructs of the present invention. Appropriate cloning and expression vectors for use with prokaryotic and eukaryotic hosts are described, for example, by Sambrook et al., *Molecular Cloning: A Laboratory Manual*, Second Edition, Cold Spring Harbor, N.Y., (1989), and may include plasmids, cosmids, shuttle vectors, viral vectors and vectors comprising a chromosomal origin of replication as disclosed therein. In one preferred embodiment, a nucleic acid expression construct comprises an expression control sequence operably linked to a polynucleotide encoding a hybrid polypeptide of SEQ ID NO:2, 4, 6, 8, 10, 12, 14, or 16. In another preferred embodiment, the nucleic acid expression construct has an inducible promoter, which may be lac, tac, trc, ara, trp, λ phage, T7 phage, and T5 phage promoter, and more preferably is a T5 phage promoter/lac operator expression control sequence as set forth in SEQ ID NO:17. The "expression control sequence" refers to any sequences sufficient to allow expression of a protein of interest in a host cell, including one or more promoter sequences, enhancer sequences, operator sequences (e.g., lacO), and the like. In certain embodiments, the hybrid polypeptide-encoding nucleic acid is in a plasmid, more preferably in plasmid pT5 (SEQ ID NO:17) and the host cell is a bacterium, most preferably *Escherichia coli*.

It should be understood that hybrid polypeptide-encoding nucleic acid may be a variant of the natural sequence due to, for example, the degeneracy of the genetic code (including alleles). Briefly, such "variants" may result from natural polymorphisms or may be synthesized by recombinant methodology (e.g., to obtain codon optimization for expression in a particular host) or chemical synthesis, and may differ from wild-type polypeptides by one or more amino acid substitutions, insertions, deletions, or the like. Variants encompassing conservative amino acid substitutions include, for example, substitutions of one aliphatic amino acid for another, such as Ile, Val, Leu, or Ala or substitutions of one polar residue for another, such as between Lys and Arg, Glu and Asp, or Gln and Asn. Such substitutions are well known in the art to provide variants having similar physical properties and functional activities, such as for example, the ability to elicit and cross-react with similar antibodies. Other variants include nucleic acids sequences that encode a hybrid polypeptide having at least 50%, 60%, 70%, 80%, 90% or 95% amino acid identity to SEQ ID NOS:2, 4, 6, 8, 10, 12, 14, or 16. Preferred embodiments are those having greater than 90% or 95% identity with the amino acid sequence of SEQ ID NOS:2, 4, 6, 8, 10, 12, 14, or 16. As will be appreciated by those of ordinary skill in the art, a nucleotide sequence encoding an hybrid polypeptide or variant thereof may differ from the native sequences presented herein due to codon degeneracy, nucleotide polymorphism, or nucleotide substitution, deletion or insertion. Thus, in certain aspects the present invention includes all degenerate nucleic acid molecules that encode polypeptides and peptides comprising the amino acid sequence of SEQ ID NOS:2, 4, 6, 8, 10, 12, 14, or 16. In another aspect, included are nucleic acid molecules that encode hybrid polypeptide variants having conservative amino acid substitutions or deletions or substitutions such that the hybrid polypeptide variant retains at least one epitope capable of eliciting antibodies specific for one or more streptococcal serotypes.

In certain aspects, a nucleic acid sequence may be modified to encode a hybrid polypeptide variant wherein specific codons of the nucleic acid sequence have been changed to codons that are favored by a particular host and can result in enhanced levels of expression (see, e.g., Haas et al., *Curr. Biol.* 6:315, 1996; Yang et al., *Nucleic Acids Res.* 24:4592, 1996). For example, certain codons of the immunogenic peptides obtained from streptococcal M proteins were optimized, without changing the primary sequence of the peptides, for improved expression in *Escherichia coli*. By way of illustration and not limitation, eleven of the thirteen arginine (Arg) codons of AGG/AGA in the hexavalent hybrid polypeptide as set forth in SEQ ID NO:9 were changed to the Arg codons of CGT/CGC as set forth in SEQ ID NO:1. Similarly, twelve of twenty AGG/AGA Arg codons of SEQ ID NO:15 were optimized to CGT/CGC codons as set forth in SEQ ID NO:8; seven of thirteen AGG/AGA Arg codons of SEQ ID NO:11 were optimized to CGT/CGC codons as set forth in SEQ ID NO:3; and five of nine AGG/AGA Arg codons of SEQ ID NO:13 were optimized to CGT/CGC codons as set forth in SEQ ID NO:5. As is known in the art, codons may be optimized for whichever host the hybrid polypeptide is to be expressed in, including without limitation bacteria, fungi, insect cells, plant cells, and mammalian cells. Additionally, codons encoding different amino acids may be changed as well, wherein one or more codons encoding different amino acids may be altered simultaneously as would best suit a particular host (e.g., codons for arginine, glycine, leucine, and serine may all be optimized or any combination thereof). Alternatively, codon optimization may result in one or more changes in the primary amino acid sequence, such as a conservative amino acid substitution, addition, deletion, or combination thereof.

While particular embodiments of isolated nucleic acids encoding hybrid polypeptides are depicted in SEQ ID NOS: 1, 3, 5, 7, 9, 11, 13, and 15, within the context of the present invention, reference to one or more isolated nucleic acids includes variants of these sequences that are substantially similar in that they encode native or non-native hybrid polypeptides with similar structure and ability to elicit serospecific antibodies to at least one immunogenic peptide subunit contained in the hybrid polypeptides of SEQ ID NOS:2, 4, 6, 8, 10, 12, 14, or 16. As used herein, the nucleotide sequence is deemed to be "substantially similar" if: (a) the nucleotide sequence is derived from the coding region of a emm gene isolated from a streptococcus (including, for example, portions of the sequence or allelic variations of the sequences discussed above) and contains a M protein epitope with substantially the same ability to elicit opsonic antibodies protective against streptococci that are not tissue cross-reactive; (b) the nucleotide sequence is capable of hybridization to the nucleotide sequences of the present invention under moderate or high stringency; (c) the nucleotide sequences are degenerate (i.e., sequences which code for the same amino acids using a different codon sequences) as a result of the genetic code to the nucleotide sequences defined in (a) or (b); or (d) is a complement of any of the sequences described in (a), (b) or (c).

As used herein, two nucleotide sequences are said to "hybridize" under conditions of a specified stringency when stable hybrids are formed between substantially complementary nucleic acid sequences. Stringency of hybridization refers to a description of the environment under which hybrids are annealed and washed, which typically includes ionic strength and temperature. Other factors that might affect hybridization include the probe size and the length of time the hybrids are allowed to form. For example, "high," "medium" and "low" stringency encompass the following conditions or equivalent conditions thereto: high stringency is 0.1×SSPE or SSC, 0.1% SDS, 65° C.; medium stringency is 0.2×SSPE or SSC, 0.1% SDS, 50° C.; and low stringency is 1.0×SSPE or SSC, 0.1% SDS, 50° C. As used herein, the term "high stringency conditions" means that one or more sequences will remain hybridized only if there is at least 95%, and preferably at least 97%, identity between the sequences. In preferred embodiments, the nucleic acid sequences that remain hybridized to a hybrid polypeptide-encoding nucleic acid molecule encode polypeptides that retain at least one epitope of a hybrid polypeptide encoded by a nucleic acid of any one of SEQ ID NOS:1, 3, 5, 7, 9, 11, 13, and 15.

Methods for producing the hybrid polypeptides of the subject invention are provided as well wherein any of the nucleic acid molecules and host cells described herein may be used. In a preferred embodiment, a method of producing a hybrid polypeptide comprises culturing a host cell containing a nucleic acid expression vector comprising at least one expression control sequence operably linked to a nucleic acid molecule encoding a hybrid polypeptide, such as a hybrid polypeptide as set forth in any one of SEQ ID NOS:2, 4, 6, 8, 10, 12, 14, or 16, under conditions and for a time sufficient for expression of the polypeptide. In one particularly preferred embodiment, a hybrid polypeptide is produced by this method, and more preferably the hybrid polypeptides produced are of SEQ ID NOS:10, 12, 14, or 16, and more preferably the hybrid polypeptides produced are of SEQ ID NOS:2, 4, 6, or 8.

The following examples are offered by way of illustration and not by way of limitation.

EXAMPLES

Example 1

Generation of Recombinant Multivalent and Individual Streptococcal Proteins Once the specific 5' sequences of each emm and spa gene had been selected for inclusion in the vaccine, they were used to design four hybrid nucleic acid molecules, each containing 6-7 emm and/or spa coding sequences linked in tandem by unique restriction enzyme recognition sites (FIGS. 1-5). The four hybrid nucleic acid molecules were constructed using PCR-generated emm or spa nucleic acid molecules that were amplified from streptococcal genomic DNA of the corresponding serotype using oligonucleotide forward and reverse primers containing restriction enzyme sites at the 5' end. The PCR-generated fragments were purified, digested with the appropriate restriction enzymes, ligated using methods previously described (Dale et al., *J. Immunol.* 151:2188, 1993; Dale, *Vaccine* 17:193, 1999), and then sequentially cloned into the expression vector pT5. Plasmid pT5 (SEQ ID NO:17) comprises a bacteriophage T5 promoter operably to lac operators, which means expression from the T5 promoter can be induced with isopropyl-beta-D-thiogalactopyranoside (IPTG).

The 5' emm fragment was reiterated at the 3' end of each hybrid nucleic acid molecule based on observations that an amino-terminal M protein peptide reiterated on the carboxy-terminus of a hybrid polypeptide appears to enhance or protect the immunogenicity of the adjacent M protein peptides (see Dale, *Vaccine* 17:193, 1999; WO 99/13084). In addition, the emm nucleic acid molecule cloned at the 3'-end of the hybrid molecule was engineered to include at the 5' end the following: (a) at least six histidine codons, (b) a XhoI restriction enzyme site, (c) optionally one or more amino acid codons (e.g., cysteine), and (d) at least one stop codon (TAA or TAG). Several of the Arg codons from each of the hexavalent and septavalent polypeptides were optimized (see FIGS. 2-5), without changing the primary amino acid sequence, for expression in E. coli, which yielded from about a 2-fold to about a 10-fold increase in polypeptide production. The nucleic acid and amino acid sequences of the hybrid polypeptides used to make admixtures for immunizing rabbits and/or humans are set forth in SEQ ID NOS:1-16. Each expression plasmid construct of pT5 was used to transform E. coli strain JM105 (genotype F' traD36 lacI$^q$Δ(lacZ)M15proA$^+$B$^+$/thi rpsL (str$^r$) endA sbcB15 sbcC? hsdR4($r_k^-m_k^-$) Δ(lac-proAB). The sequence identity of each hybrid DNA molecule transformed into JM105 E. coli was verified by sequencing both strands. Expression of each component fusion protein was detected by SDS-PAGE analysis using whole cell lysates before and after 1 mM IPTG induction.

In addition to the hybrid multivalent polypeptides generated to immunize a particular subject, recombinant homodimeric peptides comprising a single serotype immunogenic peptide were expressed and purified to test immune sera elicited by the hybrid streptococcal polypeptides. Each emm or spa gene fragment, included in the hybrid nucleic acid molecules described above, was independently amplified by PCR, purified, and cloned sequentially into the expression vector pT5 as an in-frame dimer with a restriction enzyme site between each coding sequence. Each PCR-generated sequence was verified by sequencing both strands of the dimer-encoding nucleic acid molecule. Expression of each peptide in transformed JM105 E. coli was detected by SDS-PAGE analysis, as described above.

Each hybrid polypeptide encoded by the hybrid nucleic acid molecules was further analyzed by BLASTP (matrix BLOSUM62) to assure that there were no significant homologies with human proteins in the GenBank database. The linking restriction enzyme sites between the emm and/or spa encoding nucleic acid molecules were selected to avoid creating a sequence encoding potential human tissue cross-reactive epitopes. Specifically, the two amino acid residues encoded by each restriction enzyme site along with the six flanking M protein or Spa residues on each side of the sites (14 residues in total) were searched using BLASTP (matrix PAM30) to detect potential homologies with human proteins in the GenBank database. Any restriction enzyme site matching more than four contiguous amino acids of a human protein sequences was not used.

Example 2

Purification of Multivalent and Individual Streptococcal Proteins

Each hybrid polypeptide and individual dimeric peptide was purified separately. Cell paste of E. coli JM105 expressing His-tagged hybrid polypeptide was lysed in phosphate buffered saline (PBS) by microfluidation (Microfluidics, Inc., Newton, Mass.). After centrifugation, the clarified lysate was batch adsorbed to nickel-loaded affinity chelate resin (Tosoh Biosep, Montgomeryville, Pa.), washed and eluted with a step gradient of imidazole in PBS. Fractions containing the eluted hybrid polypeptide were pooled, pumped through a 5 ml HITRAP® Q anion exchange cartridge (Amersham Pharmacia Biotech, Piscataway, N.J.) and concentrated in a stir cell (Millipore, Bedford, Mass.). The concentrated hybrid polypeptide was further purified by size exclusion chromatography using a SUPERDEX® 200 column (600 cm length, Amersham Pharmacia Biotech) equilibrated with PBS. Fraction purity was monitored using SDS-PAGE and fractions containing pure hybrid polypeptide were pooled and stored at −20° C. until use. Purity, identity and concentration of the hybrid polypeptide were further assessed by reverse-phase HPLC, amino acid analysis, and electrospray mass spectrometry.

Individual dimeric peptides were similarly purified, but with notable differences. E. coli JM105 expressing 6×His-tagged dimeric peptide were lysed in PBS containing 8M urea for 3 hours with stirring. After centrifugation, the clarified lysate was batch adsorbed to nickel-loaded affinity chelate resin (Tosoh Biosep) and washed and eluted with a step gradient of imidazole in PBS. The eluted dimeric peptide was then loaded onto a preparative reverse-phase C4 column (Vydac, Hesperia, Calif.), washed, and eluted with increasing concentrations of acetonitrile in water containing 0.1% trifluoroacetic acid. Fractions of eluted dimeric peptide were monitored using SDS-PAGE. Fractions containing purified dimeric peptide were pooled and dialyzed against PBS before storage at −20° C.

Example 3

Formulation of Hybrid Polypeptide Cocktail and Immunization of Rabbits

The four multivalent polypeptides (Hexa A.1 [SEQ ID NO:10], Septa B.2 [SEQ ID NO:16], Septa C.2 [SEQ ID NO:4], and Septa D.1 [SEQ ID NO:14]) were mixed in equimolar amounts and adsorbed to alum (REHYDRA-GEL®, low viscosity, Reheis, Inc., Berkeley Heights, N.J.) to achieve a final protein concentration of 800 μg/ml and a final alum concentration of 1.5 μg/ml. This cocktail of immunogenic polypeptides represent at least 27 antigens.

New Zealand white rabbits were each immunized with 400 μg (i.e., about 100 μg of each multivalent polypeptide) of the vaccine via the intramuscular route at either 0, 4, and 8 weeks or 0, 4, and 16 weeks (see Dale, Vaccine 17:193, 1999). Serum was obtained prior to the first injection and two weeks after the final injection.

Example 4

Elisa Using Serum From Immunized Rabbits

Type-specific antibodies were detected by enzyme-linked immunosorbent assays (ELISAs) essentially by methods previously described (McLellan et al., Infect. Immun. 69:2943, 2001). Briefly, microtiter wells were coated with purified recombinant dimeric M peptides (i.e., copying the vaccine subunits and used as solid-phase antigens). Wells without peptide but containing all other reagents served as negative controls. The ELISAs were performed using pre-immune and immune rabbit sera. The sera were serially diluted in PBS (pH 7.4) with 0.05% TWEEN® 20, added to the wells, and incubated at 37° C. for 2 hours. The wells were washed with 0.15% saline-TWEEN® 20. A horse radish peroxidase-conjugated goat immunoglobulin G (IgG) to rabbit immunoglobulins (IgG, IgA, and IgM) (ICN Biomedicals, Aurora, Ohio) diluted 1:2,000 was added and incubated at 37° C. for 2 hours. The wells were then washed, 5-aminosalicylic acid was added, and the $A_{450}$ was recorded after 15 minutes in an MR 600 microplate reader (Dynatech Laboratories, Inc., Chantilly, Va.).

Figure 7:
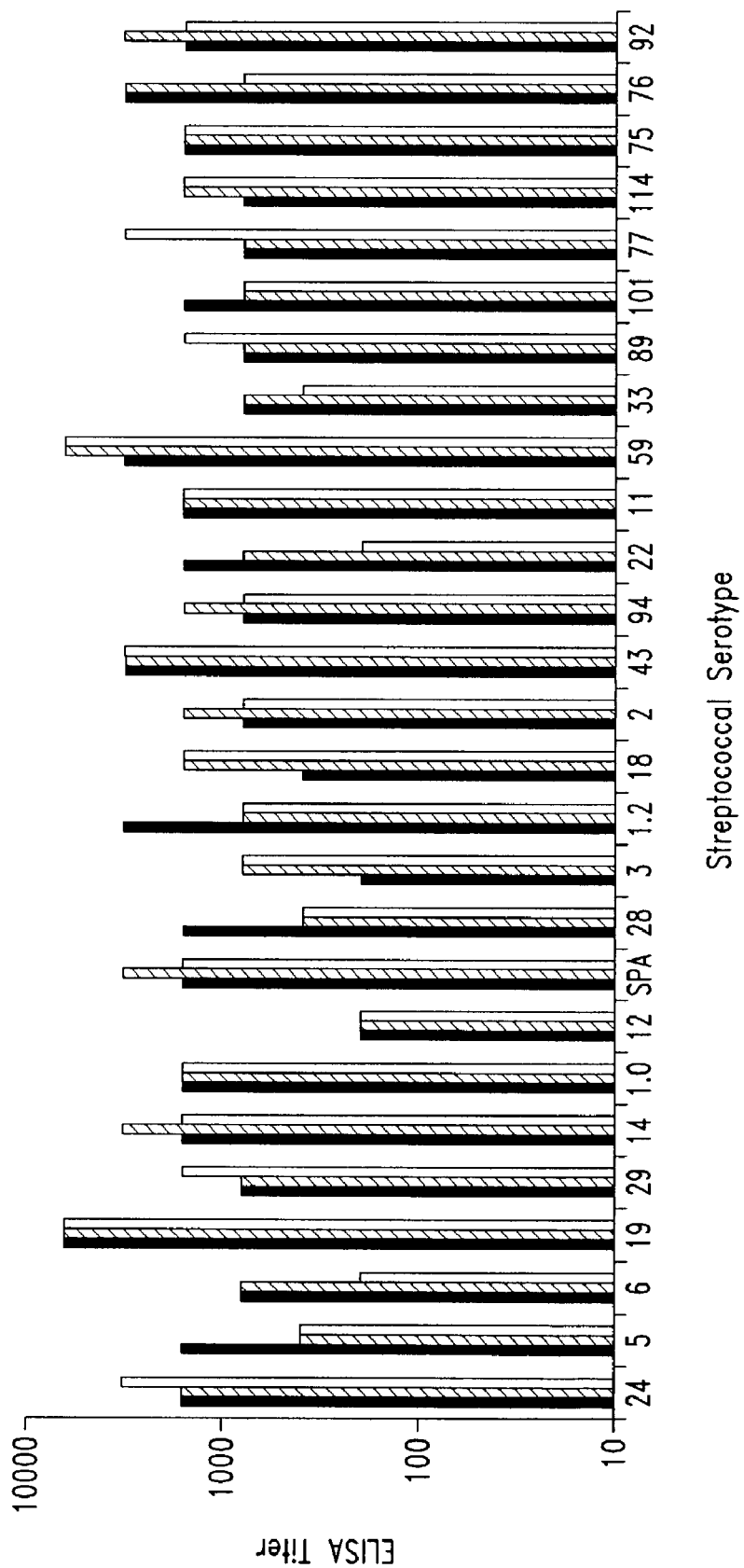
FIG. 7 shows that type-specific M protein and Spa antibodies were elicited by a vaccinating agent comprising a cocktail of four different hybrid polypeptides (i.e., a 27-valent vaccine) when examined by ELISA. Each bar represents serum from one rabbit.

The immune sera from rabbits (obtained 2 weeks after the final immunization) contained high titers of antibodies to the majority of the M peptides contained in the vaccine (FIG. 7). Antibody titers were determined for each of the 26 M peptides and Spa, a new protective antigen of group A streptococci (Dale et al., *J. Clin. Invest.* 130:1261, 1999). All pre-immune titers were less than 200. Out of the 81 immune serum titers determined (27 antigens×3 rabbits), 69 titers (85%) increased by four-fold or greater over the pre-immune levels (FIG. 7).

Example 5

Opsonization Assays Using Serum From Immunized Rabbits

Opsonic antibodies were detected by in vitro opsonization assays, essentially as previously described (Beachey et al., *J. Exp. Med.* 145:1469, 1977). The test mixture consisted of 0.05 ml of a standard suspension of streptococci grown to mid-log phase, 0.05 ml test serum, and 0.2 ml whole, heparinized (10 U/ml) nonimmune human blood. For these assays, the number of streptococcal CFU per leukocyte was approximately 10. The tubes were rotated end-over-end for 45 minutes at 37° C. Smears were then made on glass slides and stained with Wright's stain (Sigma Diagnostics, St. Louis, Mo.). Opsonization was quantitated by counting 50 consecutive neutrophils and calculating the percentage with associated streptococci (percent opsonization).

Figure 8:
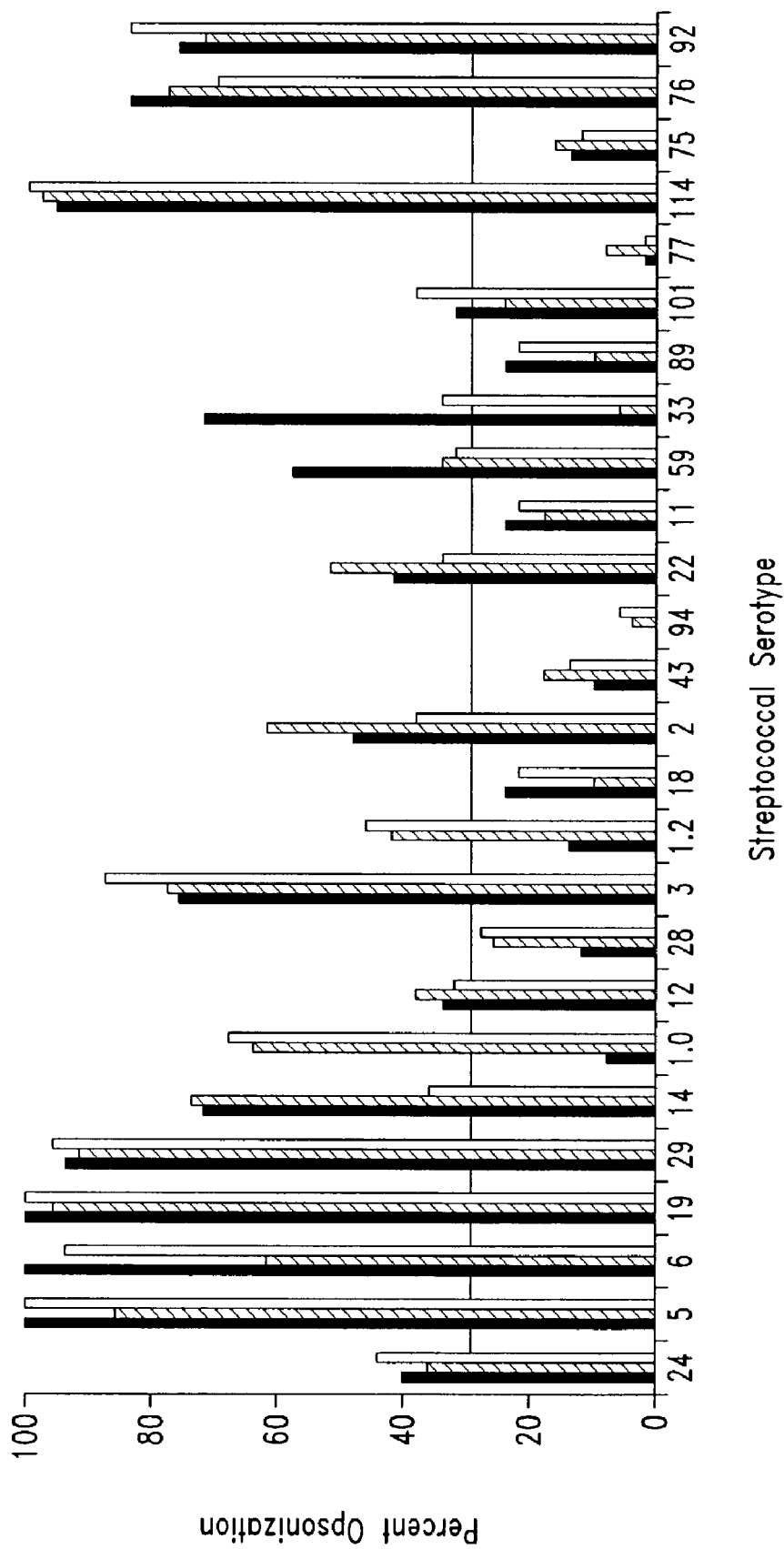
FIG. 8 shows the results of in vitro opsonization assays using immune sera, which were elicited in rabbits with a composition comprising a cocktail of four different hybrid polypeptides (i.e., a 27-valent vaccine). A positive response was considered at least a 3-fold increase over opsonization with pre-immune (i.e., 30% or greater opsonization). The pre-immune sera resulted in less than 10% opsonization of each streptococcal serotype. Each bar represents serum from one rabbit.

The pre-immune sera from all three rabbits resulted in ≦10% opsonization of each of the 26 serotypes tested (data not shown), indicating that the donor blood used for these assays did not contain antibodies against the test organism and that each organism was fully resistant to opsonization in nonimmune blood. Using 30% opsonization in the presence of immune serum as a positive threshold result (i.e., three or more times the pre-immune level), 18 of the 26 serotypes (69%) were opsonized by at least one of three immune rabbit sera (FIG. 8).

Example 6

Bactericidal Assays Using Serum from Immunized Rabbits

Bactericidal assays were performed similar to Example 5 (Lancefield, *J. Exp. Med.* 106:525, 1957) except that 0.05 ml of Todd-Hewitt broth containing fewer bacteria was added to 0.1 ml of test serum and 0.35 ml of blood and the mixture was rotated for three hours at 37° C. Then 0.1 ml aliquots of this mixture were added to melted sheep's blood agar, pour plates were prepared, and viable organisms (CFU) were counted after overnight incubation at 37° C. For each serotype tested, three different inocula were used to assure that the growth in blood containing pre-immune serum was optimal and was quantifiable. The results are expressed as percent killing, which was calculated using the following formula: [(CFU after three hours growth with pre-immune serum)−(CFU after three hours growth with immune serum)]÷[CFU after three hours growth with pre-immune serum]×100. Only those assays that resulted in growth of the test strain to at least eight generations in the presence of pre-immune serum were used to express percent killing in the presence of immune serum.

Figure 9:
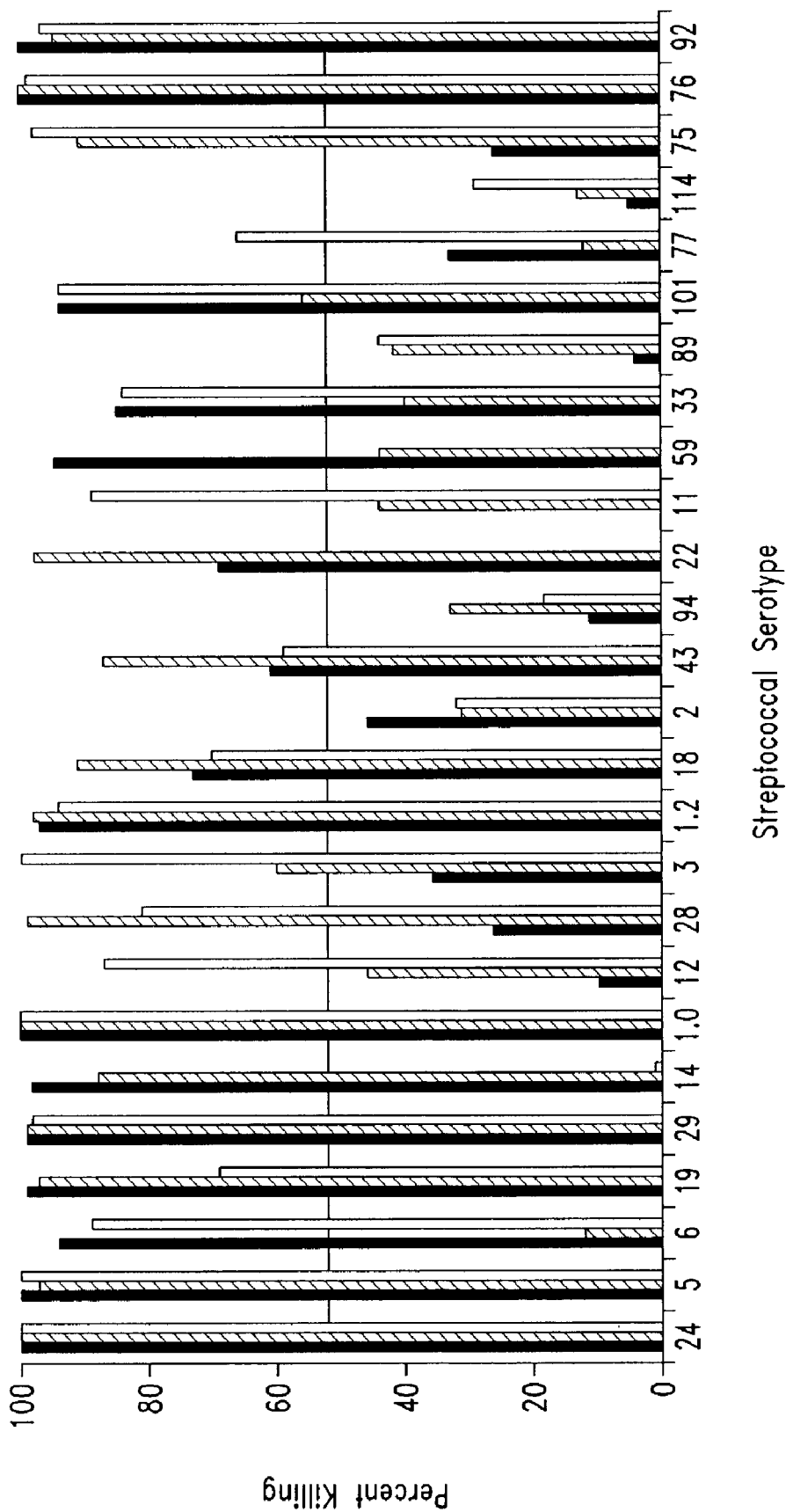
FIG. 9 shows the results of bactericidal activity assays using immune sera, which were elicited in rabbits with a vaccinating agent comprising a cocktail of four different hybrid polypeptides (i.e., a 27-valent vaccine). A positive response was considered at least a 50% percent killing. Each bar represents serum from one rabbit.

In all experiments, the test mixture containing pre-immune serum resulted in growth of the organisms to eight generations or more (data not shown), again indicating that the human blood did not contain opsonic antibodies against the test strains and that each organism was fully resistant to bactericidal killing in nonimmune blood. Using 50% reduction in growth after the three-hour rotation in immune serum compared to the pre-immune serum (percent killing), bactericidal activity was observed against 22 of the 26 serotypes tested (FIG. 9). When the results of the opsonization and bactericidal assays were combined, 24 of the 26 serotypes (92%) tested were opsonized by the immune sera in one or both assays.

Example 7

Assays to Detect Tissue Cross-Reactive Antibodies in Immunized Rabbits

Rabbit immune sera raised against a composition comprising a cocktail of four different hybrid polypeptides (i.e., a 27-valent vaccine) were tested for the presence of tissue cross-reactive antibodies by indirect immunofluorescence assays (Dale and Beachey, *J. Exp. Med.* 161:113, 1985) using frozen sections (4 μm) of human myocardium, kidney, basal ganglia, cerebral cortex, and cartilage. The sections were placed on gelatin-coated slides and fixed with 1% paraformaldehyde for 10 min. The slides were washed with PBS, incubated with the immune sera diluted 1:5 in PBS for 30 minutes at room temperature, and washed thoroughly in PBS. The sections were then incubated with fluorescein-conjugated goat anti-rabbit IgG (Cappel, West Chester, Pa.) at a dilution of 1:40 in PBS for 30 minutes at room temperature. After washing, the slides were mounted in Gelvatol and examined in a fluorescent microscope. Rabbit anti-sera known to cross-react with human myocardium, kidney, and brain were used as positive controls and rabbit pre-immune sera as negative controls.

While the hybrid polypeptides elicited opsonic antibodies to most GrAS serotypes tested, none of the hybrid polypeptides elicited human cross-reactive antibodies. This indicates that the hybrid polypeptides, alone or in combination, do not contain potentially harmful autoimmune epitopes.

Example 8

Bactericidal Activity of Serum from Immunized Rabbits Against Other Serotypes

Figure 10:
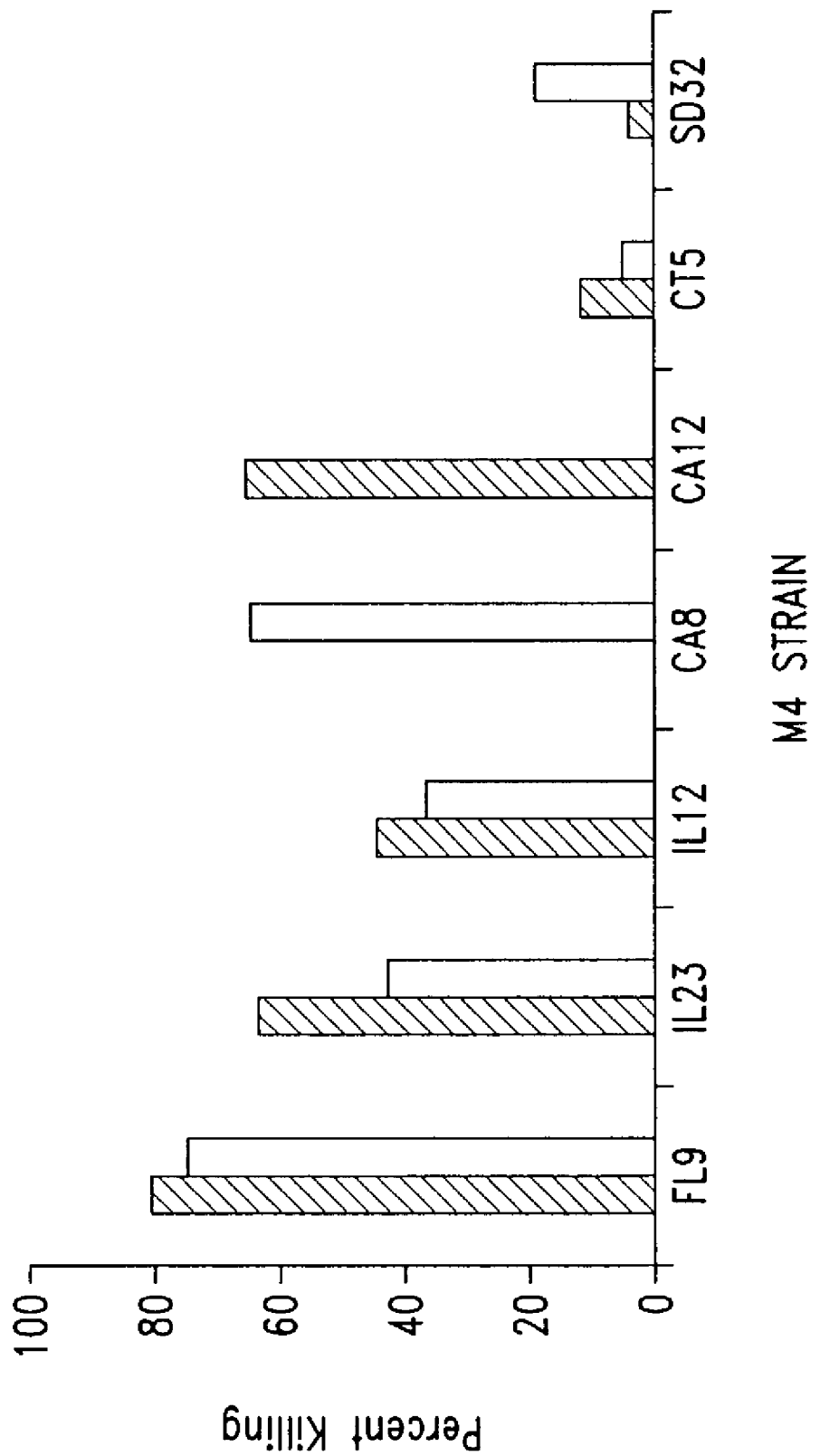
FIG. 10 shows that an immune response with bactericidal activity is elicited against group A streptococcal serotype 4, which is a serotype not represented in the 27-valent vaccinating agent. Each bar represents serum from one rabbit. Immune sera were from a rabbit immunized at 0, 4, and 8 weeks (stripped bar) and from a rabbit immunized at 0, 4, and 16 weeks (open bar). The serotype 4 streptococcal isolates were from five different geographic locations, including Florida (FL); Illinois (IL); California (CA); Connecticut (CT); and South Dakota (SD).

Type 4 streptococci are relatively common causes of uncomplicated pharyngitis and invasive infections. Type 4 organisms currently account for 3.8% of all invasive infections and 8.6% of all pharyngitis isolates in the ongoing U.S. surveillance program (personal communication, S. T. Shulman). Not wishing to be bound by theory, it appears that purified recombinant type 4 M protein either does not evoke opsonic antibodies or the type 4 streptococcal strains are resistant to opsonization. For this reason, the emm4 gene fragment was not included in the composition comprising the four hybrid polypeptides of Hexa A.1 [SEQ ID NO:10], Septa B.2 [SEQ ID NO:16], Septa C.2 [SEQ ID NO:4], and Septa D.1 [SEQ ID NO:14] (i.e., the 27-valent vaccine). To determine whether any of the antibodies elicited by the 27-valent vaccine might be directed against cross-reactive opsonic epitopes on the surface of type 4 streptococci, bactericidal assays were performed using seven clinical isolates obtained from the U.S. Streptococcal Pharyngitis Surveillance Program (FIG. 10).

Interestingly, bactericidal activity was detected against five of the seven strains of type 4 streptococci. The strains isolated from patients in Florida (FL9) and Illinois (IL23 and IL12) were opsonized by both of the 27-valent antisera tested. One of the two antisera opsonized both isolates from California (CA8 and CA12), while the strains from Connecticut (CT5) and South Dakota (SD32) were not opsonized by either antiserum (FIG. 10). The results suggest that the 27-valent cocktail vaccine can evoke antibodies that cross-react with protective epitopes on the surface of some strains of type 4 streptococci. In addition, the data indicate that type 4 streptococci may be a heterogeneous group of organisms that express different protective epitopes even though they all express the type-specific M4 protein.

Example 9

Formulation of Hybrid Polypeptide Cocktail and Immunization of Humans

The formulated bulk vaccine consists of the four recombinant proteins (Hexa A.3 [SEQ ID NO:2], Septa B.3a [SEQ ID NO:8], Septa C.2 [SEQ ID NO:4], and Septa D.3 [SEQ ID NO:6]) adsorbed onto aluminum hydroxide (final alum concentration of about 1.5 µg/ml) and diluted to a target concentration of about 400 µg/ml or about 800 µg/ml (100 µg/ml or 200 µg/ml, respectively, of each hybrid polypeptide) with phosphate buffered saline. This cocktail of immunogenic polypeptides represents at least 27 antigens.

Briefly, the calculated volumes of the purified hybrid polypeptides in PBS are measured out and added to a sterile polystyrene media bottle. The mixture is stirred until homogenous, and then diluted with an equal volume of sterile water for injection. This dilution step reduces the concentration of $Na_2HPO_4$ and NaCl in the mixture to the desired final concentration (5 mM phosphate, 150 mM NaCl, pH 7.5). The pooled HYBRID polypeptides are then passed through a sterilizing filter unit (MILLIPAK® 20, Millipore, Bedford, Mass.) using a peristaltic pump. If some peptides require some special conditions to homogenize or dilute, then the solutions are made separately and subsequently mixed with an adjustment to pH, as needed.

The required volume of recombinant hybrid polypeptides is measured out, and added to a formulation bottle. REHYDRAGEL® (low viscosity, Reheis, Inc., Berkeley Heights, N.J.) is received as a sterile suspension of aluminum hydroxide in water for injection and is used without further preparation. The required volume of REHYDRAGEL® is measured out and added to the formulation bottle while stirring. The pH of the mixture is measured and adjusted to pH 7.5-7.7 using 1 M NaOH. Finally, formulation buffer is added to achieve the correct final volume and the mixture stirred for an additional 16-20 hours at room temperature. The bulk vaccine is divided into containers (sterile), samples are taken for testing, and the formulated vaccine is stored at 2-8° C.

Human volunteers were screened and 30 healthy subjects aged 18-50 years were enrolled. Each subject was immunized with 400 µg of the cocktail vaccine composition via the intramuscular route at 0, 30, and 120 days. Serum was obtained prior to the first injection and at days 14, 30, 44, 60, 120, 134 and 150.

Example 10

Elisa Using Serum From Immunized Human Subjects

Type-specific antibodies were detected by ELISA, similar to the methods described in Example 4 (see also McLellan et al., *Infect. Immun.* 69:2943, 2001). Briefly, microtiter wells were coated with purified recombinant dimeric M peptides (i.e., copying the vaccine subunits and used as solid-phase antigens). Wells without human sera but containing all other reagents served as negative controls. The ELISAs were performed using the collected human sera. The sera were serially diluted in PBS (pH 7.4) with 0.1% BSA and 0.05% TWEEN® 20, added to the wells, and incubated at 37° C. for 2 hours. The wells were washed with PBS-0.05% TWEEN® 20. A horseradish peroxidase-conjugated goat immunoglobulin G (IgG) to human immunoglobulins (IgG, IgA, and IgM) (Jackson ImmunoResearch Laboratories, West Grove, Pa.) diluted 1:2,000 was added and incubated at 37° C. for 1 hour. The wells were then washed, 1-Step™ Turbo TMB-ELISA substrate (Pierce, Rockford, Ill.) was added, 1 N sulfuric acid was added after 30 minutes. The $A_{450/595}$ was recorded in a $V_{MAX}$® microplate reader (Molecular Devices, Sunnyvale, Calif.).

Figure 11:
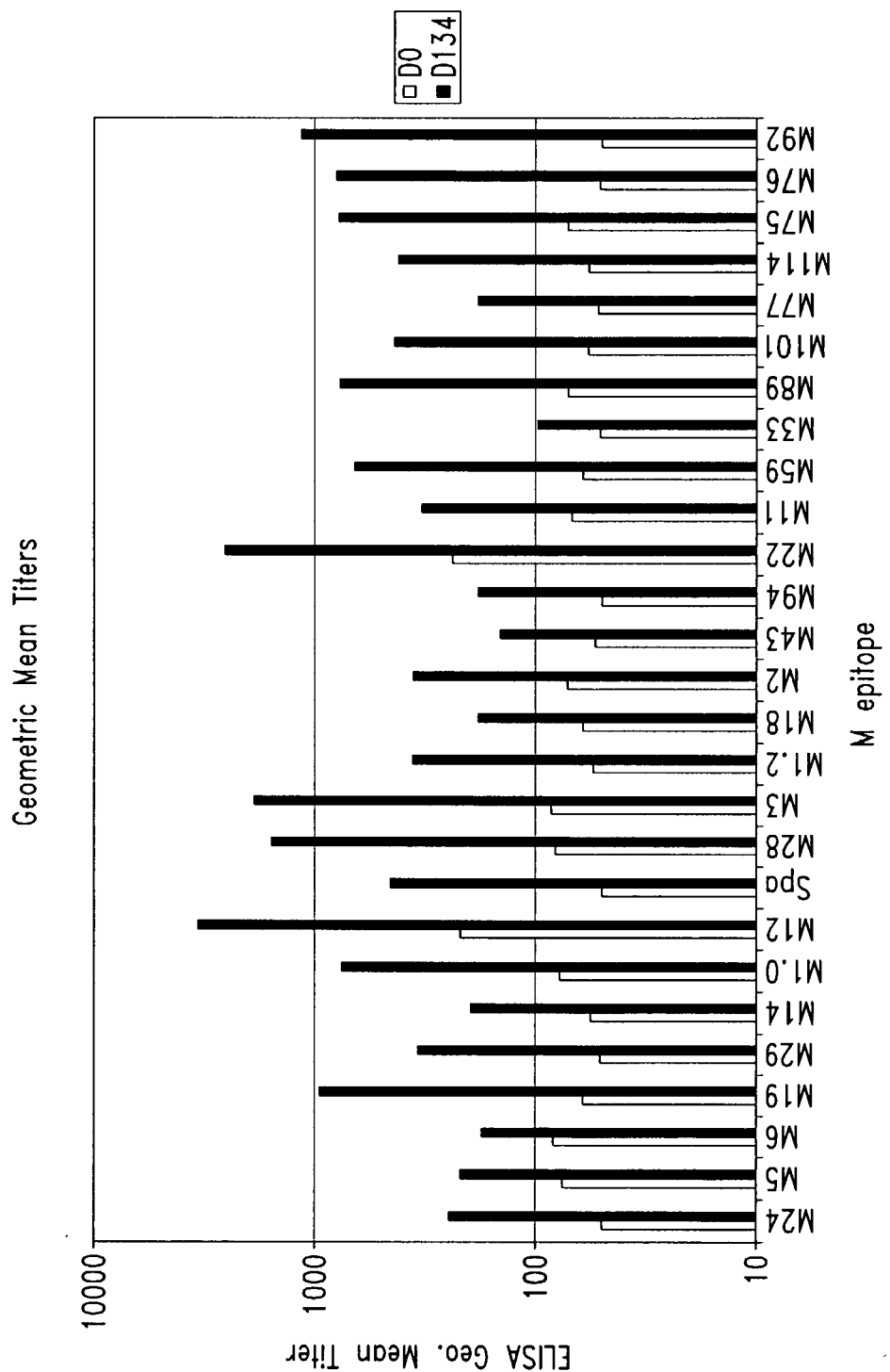
FIG. 11 shows the geometric mean antibody titers before (Day 0) and after (Day 134) immunization of human subjects, as determined by ELISA. The graph is in a $\log_{10}$ scale. Serotype M101 was formerly designated stNS5, serotype st2967 is now designated M114, and serotype M13 is now designated M94.

All of the immune sera from the human subjects (obtained at Day 134, which was two weeks after the third injection on Day 120) showed a statistically significant rise in antibody titer for all M antigens and the Spa antigen, with a p value <0.001 (FIG. 11). All subjects had a baseline level pre-immune titer for some antigens (Day 0) as seen in FIG. 11 (Day 0, open bars). The geometric mean fold increase in serum antibody to all of the antigens in the 27-valent cocktail was 12.6-fold, with a minimum increase of three-fold and a maximum increase of over 68-fold. Overall, 26 out of the 27 antigens represented in the vaccine evoked at least a four-fold mean increase in antibody titer.

Example 11

Bactericidal Assays Using Serum from Immunized Human Subjects

Bactericidal assays were performed essentially as described in Example 6 (see also Lancefield, *J. Exp. Med.* 106:525, 1957). Only those assays that resulted in growth of the test strain in the presence of Day 0 serum were used to express percent killing in the presence of Day 134 serum.

Figure 12:
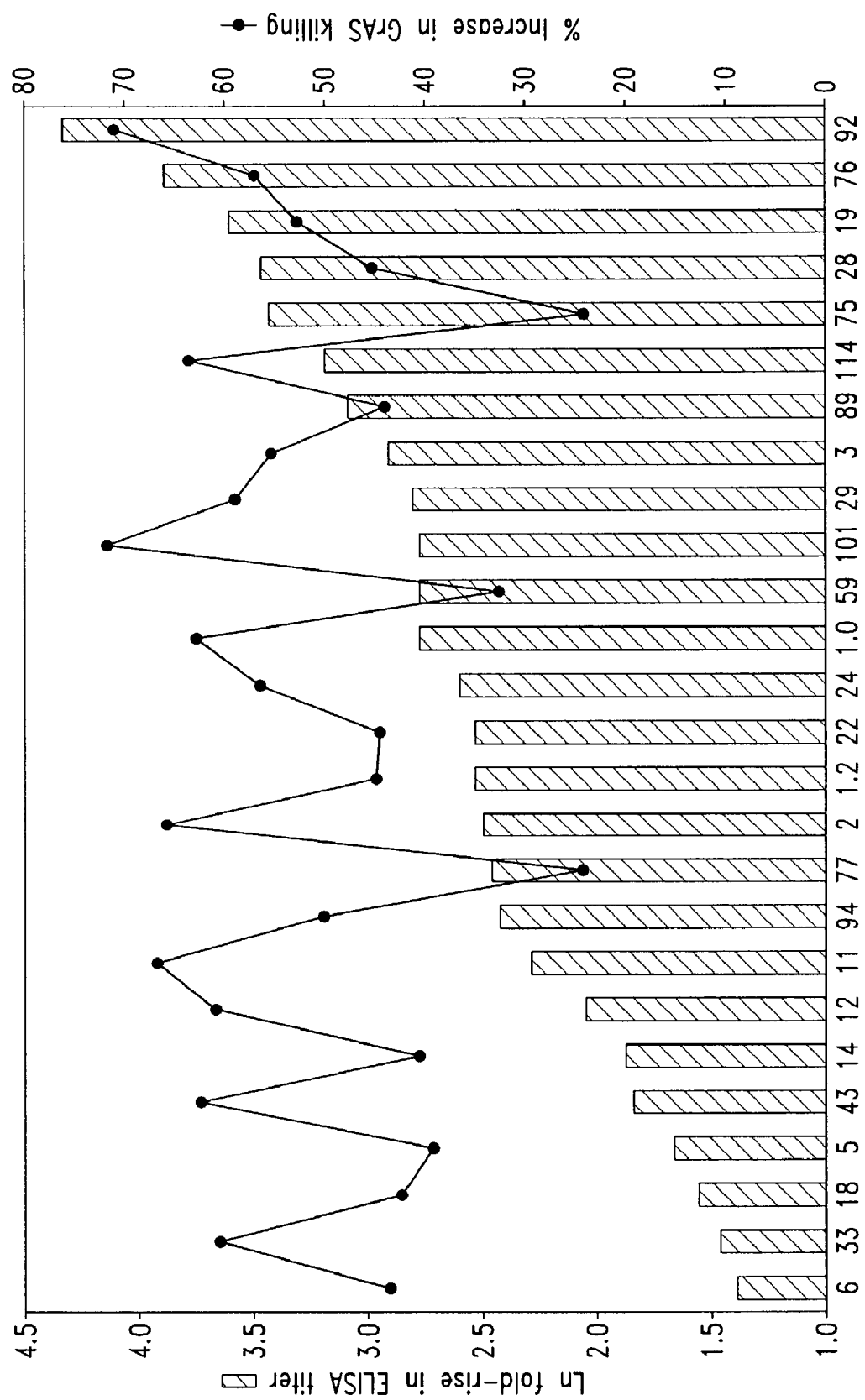
FIG. 12 shows the natural log fold-increase in ELISA-determined antibody titer (bars) as compared to percent increase in Group A streptococcal killing by polymorphonuclear cells in 26 serotypes. Serotype M101 was formerly designated stNS5, serotype M114 was formerly designated st2967, and serotype M13 is now designated M94.

All subjects that showed a rise in antibody titers over baseline level pre-immune titers also showed an increase over baseline levels bactericidal activity (FIG. 12). The geometric mean antibody titer increase was determined as in Example 10 and converted to log normal (Ln) for comparison to functional activity (bactericidal killing) of the same immune sera. Thus, there is a quantitative correlation between increased antibody titers and the ability of antibodies to induce bacterial killing.

Example 12

Assays to Detect Tissue Cross-Reactive Antibodies in Serum from Immunized Human Subjects Sera collected from human subjects, who were immunized with a 27-valent vaccine composition comprising a cocktail of four different hybrid polypeptides (Hexa A.3 [SEQ ID NO:2], Septa B.3a [SEQ ID NO:8], Septa C.2

[SEQ ID NO:4], and Septa D.3 [SEQ ID NO:6]), were tested for the presence of tissue cross-reactive antibodies as essentially described in Example 7.

Similar to the results observed in rabbits, none of the hybrid polypeptides elicited human cross-reactive antibodies. This indicates that the hybrid polypeptides, alone or in combination, do not contain potentially harmful human autoimmune epitopes.

Example 13

Figure 13:
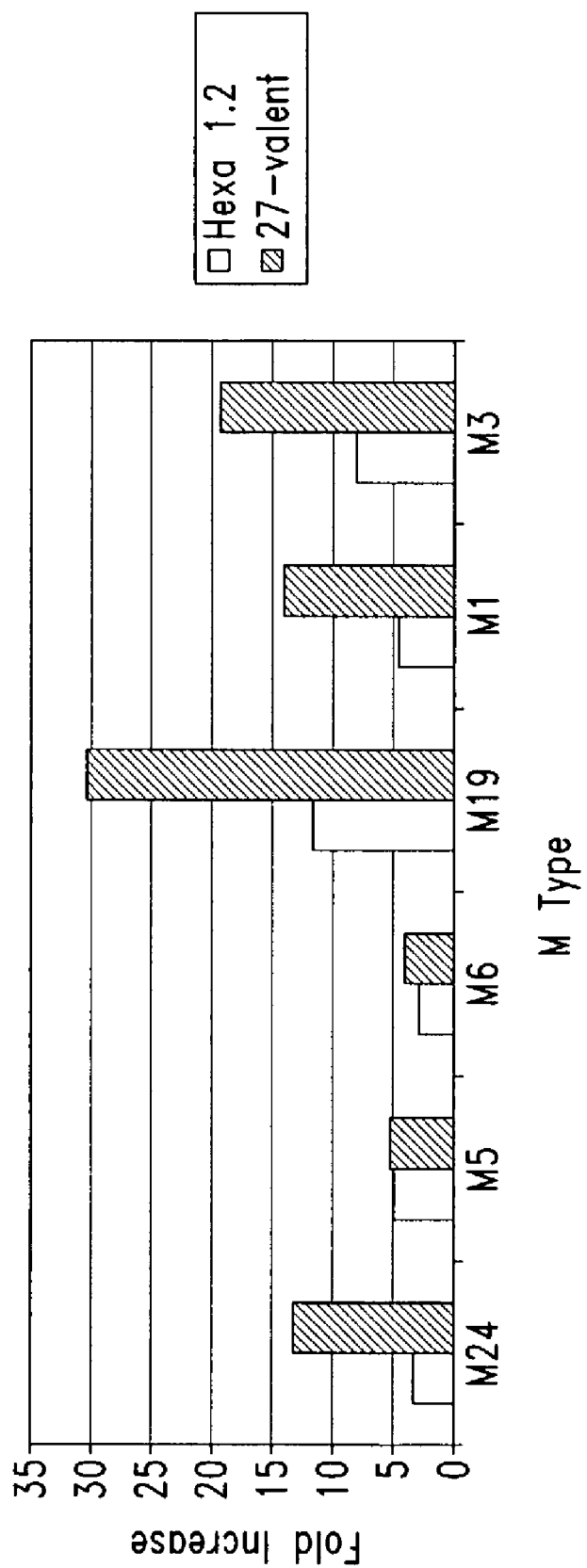
FIG. 13 shows the fold-increase in geometric mean antibody titers in human subjects immunized with a hexavalent polypeptide (Hexa 1.2) as compared to the geometric mean antibody titers in human subjects immunized with a 27-valent cocktail of four hybrid multivalent polypeptides (Hexa A.3, Septa B.3a, Septa C.2, and Septa D.3; see FIG. 1). Geometric mean antibody titers were calculated based on ELISAs against the six serotypes present in both vaccines.

Comparison of Hexavalent Vaccine Versus 27-Valent Cocktail Vaccine Used to Immunized Human Subjects A similar human trial was performed using single hexavalent polypeptide Hexa 1.2, which has a structure of M24-M5-M6-M19-M1-M3-M24 (see Dale, Vaccine 17:193, 1999; WO 99/13084). Human volunteers were screened and 11 healthy subjects were each immunized three times with 100 μg of Hexa 1.2 in the same formulation buffer as used for the 27-valent vaccine composition comprising a cocktail of four different hybrid polypeptides (Hexa A.3 [SEQ ID NO:2], Septa B.3a [SEQ ID NO:8], Septa C.2 [SEQ ID NO:4], and Septa D.3 [SEQ ID NO:6]). All six of the group A streptococcal antigens of Hexa 1.2 (M24, M5, M6, M19, M1, and M3) are represented in two of the four multivalent polypeptides that comprise the 27-valent vaccine. ELISAs were then performed on sera from immunized subjects to identify type-specific antibodies for each of the Hexa 1.2 antigens, essentially as described in Example 10. The geometric mean titers were calculated using antibody titers from the 11 subjects that received the Hexa 1.2 multivalent polypeptide and using antibody titers from the 30 subjects in the 27-valent cocktail of four different multivalent polypeptides clinical trial, respectively (FIG. 13). The fold-increase in antibody titers represents the fold rise in geometric mean titers after immunization as compared to the geometric mean titers before immunization.

Surprisingly, the subjects immunized with the 27-valent composition showed a much greater fold-increase in antibody titers overall than did the subjects who received the hexavalent composition (FIG. 13). The 27-valent showed a greater fold-increase for all M antigens, ranging from about 1.1- to about a 4-fold increase. As noted above, the increase in antibody titer also correlates with an increase in bactericidal activity. Hence, the four multivalent peptides together unexpectedly showed a synergistic effect in evoking an immune response as compared to a single hexavalent peptide.

From the foregoing it will be appreciated that, although specific embodiments of the invention have been described herein for purposes of illustration, various modifications may be made without deviating from the spirit and scope of the invention. Accordingly, the invention is not limited except as by the appended claims.

The invention claimed is:

1. A composition comprising a pharmaceutically acceptable carrier and a mixture of at least two hybrid polypeptides selected from
   (a) a hybrid polypeptide consisting of six different immunogenic amino terminal peptides from six different group A streptococcal M proteins M24, M5, M6, M19, M29 and M14, wherein the six different immunogenic amino terminal peptides are linked in tandem by at least two amino acids, wherein each of the immunogenic amino terminal peptides comprises at least 30 contiguous amino acids of each of said group A streptococcal M proteins, wherein the immunogenic amino terminal peptide at the amino terminus of the hybrid polypeptide is reiterated at the carboxy terminus of the hybrid polypeptide and wherein the hybrid polypeptide is capable of eliciting an immune response against more than one of said group A streptococcal M proteins M5, M6, M14, M19, M24 and M29;
   (b) a hybrid polypeptide consisting of seven different immunogenic amino terminal peptides from seven different group A streptococcal M proteins M2, M43, M94, M22, M11, M59 and M33, wherein the seven different immunogenic amino terminal peptides are linked in tandem by at least two amino acids, wherein each of the immunogenic amino terminal peptides comprises at least 35 contiguous amino acids of each of said group A streptococcal M proteins, wherein the immunogenic amino terminal peptide at the amino terminus of the hybrid polypeptide is reiterated at the carboxy terminus of the hybrid polypeptide and wherein the hybrid polypeptide is capable of eliciting an immune response against more than one of said group A streptococcal M proteins M2, M11, M22, M33, M43, M59 and M94;
   (c) a hybrid polypeptide consisting of seven different immunogenic amino terminal peptides from seven different group A streptococcal M proteins M89, M101, M77, M114, M75, M76 and M92, wherein the seven different immunogenic amino terminal peptides are linked in tandem by at least two amino acids, wherein each of the immunogenic amino terminal peptides comprises at least 40 contiguous amino acids of each of said group A streptococcal M proteins, wherein the immunogenic amino terminal peptide at the amino terminus of the hybrid polypeptide is reiterated at the carboxy terminus of the hybrid polypeptide and wherein the hybrid polypeptide is capable of eliciting an immune response against more than one of said group A streptococcal M proteins M75, M76, M77, M89, M92, M101 and M114; and
   (d) a hybrid polypeptide consisting of seven different immunogenic amino terminal peptides from seven different group A streptococcal proteins M1.0, M12, Spa, M28, M3, M1.2, M18 and M1.0, wherein the seven different immunogenic amino terminal peptides are linked in tandem by at least two amino acids, wherein each of the immunogenic amino terminal peptides comprises at least 50 contiguous amino acids of each of said group A streptococcal proteins, wherein the immunogenic amino terminal peptide at the amino terminus of the hybrid polypeptide is reiterated at the carboxy terminus of the hybrid polypeptide and wherein the hybrid polypeptide is capable of eliciting an immune response against more than one of said group A streptococcal proteins Spa, M1.0, M1.2, M3, M12, M18 and M28.

2. The composition according to claim 1 wherein the at least two hybrid polypeptides are selected from M24-M5-M6-M19-M29-M14-M24, M2-M43-M94-M22-M11-M59-M33-M2, M89-M101 -M77-M114-M75-M76-M92-M89, and M1.0-M12Spa-MM28-M3-M1.2-M18-M1.0.

3. The composition according to claim 1 wherein the mixture comprises the hybrid polypeptide of item (d) and at least one of the hybrid polypeptides of item (a), item (b) and item (c).

4. The composition according to claim 3 wherein the hybrid polypeptide of item (d) is M1.0-M12-Spa-M28-M3-M1.2-M18-M1.0 and wherein the hybrid polypeptide of item (a) is M24-M5-M6-M19-M29-M14-M24, the hybrid polypeptide of item (b) is M2-M43-M94-M22-M11-M59-M33-M2 and the hybrid polypeptide of item (c) is M89-M101-M77-M114-M75-M76-M92-M89.

5. The composition according to claim 1 wherein the mixture comprises at least three hybrid polypeptides according to item (a), item (b), item (c) and item (d).

6. The composition according to claim 5 wherein the mixture comprises at least three hybrid polypeptides selected from M24-M5-M6-M19-M29-M14-M24, M2-M43-M94-M22-M 11-M59-M33-M2, M89-M101-M77-M 114-M75-M76-M92-M89, and M1.0-M12-Spa-M28-M3-M1.2-M18-M1.0.

7. A composition comprising a pharmaceutically acceptable carrier and a mixture of (a) a recombinant hybrid polypeptide comprising the amino acid sequence set forth in SEQ ID NO: 2; (b) a recombinant hybrid polypeptide comprising the amino acid sequence set forth in SEQ ID NO: 4; (c) a recombinant hybrid polypeptide comprising the amino acid sequence set forth in SEQ ID NO: 6; and (d) a recombinant hybrid polypeptide comprising the amino acid sequence set forth in SEQ ID NO: 8.

8. The composition according to claim 7 further comprising an adjuvant.

9. The composition according to claim 8 wherein the adjuvant is selected from the group consisting of aluminum hydroxide (alum), aluminum phosphate, proteosome adjuvant, virosome, liposome, Freund's complete adjuvant, Freund's incomplete adjuvant, and an oil and water emulsion.

10. The composition according to claim 1 wherein the hybrid polypeptide of item (a) is recombinant M24-M5-M6-M19-M29-M14-M24.

11. The composition according to claim 1 wherein the hybrid polypeptide of item (b) is recombinant M2-M43-M94-M22-M11-M59-M33-M2.

12. The composition according to claim 1 wherein the hybrid polypeptide of item (c) is recombinant M89-M101-M77-M114-M75-M76-M92-M89.

13. The composition according to claim 1 wherein the hybrid polypeptide of item (d) is recombinant M1.0-M12-Spa-M28-M3-M1.2-M18-M1.0.

14. The composition according to claim 1 further comprising an adjuvant.

15. The composition according to claim 14 wherein the adjuvant is selected from the group consisting of aluminum hydroxide (alum), aluminum phosphate, proteosome adjuvant, virosome, liposome, Freund's complete adjuvant, Freund's incomplete adjuvant, and an oil and water emulsion.

* * * * *

UNITED STATES PATENT AND TRADEMARK OFFICE
CERTIFICATE OF CORRECTION

PATENT NO. : 7,270,827 B2  Page 1 of 1
APPLICATION NO. : 10/284400
DATED : September 18, 2007
INVENTOR(S) : Reddish et al.

It is certified that error appears in the above-identified patent and that said Letters Patent is hereby corrected as shown below:

Column 76
Claim 2, line 5, lines 37-38, "and M1.0-M12Spa-MM28-M3-M1.2-M18-M1.0" should read as -- and M1.0-M12-Spa-M28-M3-M1.2-M18-M1.0. --

Column 76
Claim 6, line 4 and 5, "M2-M43-M94-M22-M 11-M59-M33-M2, M89-M-101-M77-M 114-M75-M76-M92-M89" should read as -- M2-M43-M94-M22-M11-M59-M33-M2, M89-M101-M77-M114-M75-M76-M92-M89 --

Signed and Sealed this

Nineteenth Day of August, 2008

JON W. DUDAS
*Director of the United States Patent and Trademark Office*

SEQUENCE LISTING

```
<160> NUMBER OF SEQ ID NOS: 19

<210> SEQ ID NO 1
<211> LENGTH: 1005
<212> TYPE: DNA
<213> ORGANISM: Artificial Sequence
<220> FEATURE:
<221> NAME/KEY: CDS
<222> LOCATION: (1)..(1002)
<220> FEATURE:
<223> OTHER INFORMATION: Description of Artificial Sequence: Nucleic
      acid encoding Hybrid of Group A Streptococci M protein
      and M-like protein

<400> SEQUENCE: 1 atg gtc gcg act cgc tct cag aca gat act ctg gaa aaa gta caa gaa       48
Met Val Ala Thr Arg Ser Gln Thr Asp Thr Leu Glu Lys Val Gln Glu
  1               5                  10                  15 cgt gct gac aag ttt gag ata gaa aac aat acg tta aaa ctt aag aat       96
Arg Ala Asp Lys Phe Glu Ile Glu Asn Asn Thr Leu Lys Leu Lys Asn
             20                  25                  30 agt gac tta agt ttt aat aat aaa gcg tta aaa gat cat aat gat gag      144
Ser Asp Leu Ser Phe Asn Asn Lys Ala Leu Lys Asp His Asn Asp Glu
         35                  40                  45 tta act gaa gag ttg agt aat gct aaa gag aaa cta cgt cac gtg gcc      192
Leu Thr Glu Glu Leu Ser Asn Ala Lys Glu Lys Leu Arg His Val Ala
     50                  55                  60 gtg act cgc ggt aca ata aat gac ccg caa aga gca aaa gaa gct ctt      240
Val Thr Arg Gly Thr Ile Asn Asp Pro Gln Arg Ala Lys Glu Ala Leu
 65                  70                  75                  80 gac aag tat gag cta gaa aac cat gac tta aaa act aag gga tcc cgt      288
Asp Lys Tyr Glu Leu Glu Asn His Asp Leu Lys Thr Lys Gly Ser Arg
                 85                  90                  95
```

-continued

```
gtg ttt cct cgc ggg acg gta gaa aac ccg gac aaa gca cga gaa ctt        336
Val Phe Pro Arg Gly Thr Val Glu Asn Pro Asp Lys Ala Arg Glu Leu
        100                 105                 110 ctt aac aag tat gac gta gag aac tct atg tta caa gct aat aat gac        384
Leu Asn Lys Tyr Asp Val Glu Asn Ser Met Leu Gln Ala Asn Asn Asp
    115                 120                 125 aag tta cca tgg cgt gtg cgt tat act cgc cat acg cca gaa gat aag        432
Lys Leu Pro Trp Arg Val Arg Tyr Thr Arg His Thr Pro Glu Asp Lys
130                 135                 140 cta aaa aaa att att gac gat ctt gac gca aaa gaa cat gaa tta caa        480
Leu Lys Lys Ile Ile Asp Asp Leu Asp Ala Lys Glu His Glu Leu Gln
145                 150                 155                 160 caa cag aat gag aag tta tct ctg cag aaa gtg tat att act cgt ggt        528
Gln Gln Asn Glu Lys Leu Ser Leu Gln Lys Val Tyr Ile Thr Arg Gly
                165                 170                 175 atg aca aaa gag gac gta gaa aaa att gct aac aac ctt gac ata gaa        576
Met Thr Lys Glu Asp Val Glu Lys Ile Ala Asn Asn Leu Asp Ile Glu
        180                 185                 190 aac cat ggg tta aaa caa cag aat gaa cag tta tct act gat aaa caa        624
Asn His Gly Leu Lys Gln Gln Asn Glu Gln Leu Ser Thr Asp Lys Gln
    195                 200                 205 ggt ctt gaa gaa cag aat ggt acc gat cgc gtt agt cgt tct atg tca        672
Gly Leu Glu Glu Gln Asn Gly Thr Asp Arg Val Ser Arg Ser Met Ser
210                 215                 220 cgc gat gat cta tta aac agg gct cag gat ctt gaa gca aaa aac cac        720
Arg Asp Asp Leu Leu Asn Arg Ala Gln Asp Leu Glu Ala Lys Asn His
225                 230                 235                 240 ggg tta gaa cac cag aat act aag tta tct act gaa aat aaa acg ctt        768
Gly Leu Glu His Gln Asn Thr Lys Leu Ser Thr Glu Asn Lys Thr Leu
                245                 250                 255 caa gaa caa gca gaa gca cgc cag aaa gaa atc gat gtc gcg act cgc        816
Gln Glu Gln Ala Glu Ala Arg Gln Lys Glu Ile Asp Val Ala Thr Arg
        260                 265                 270 tct cag aca gat act ctg gaa aaa gta caa gaa cgt gct gac aag ttt        864
Ser Gln Thr Asp Thr Leu Glu Lys Val Gln Glu Arg Ala Asp Lys Phe
    275                 280                 285 gag ata gaa aac aat acg tta aaa ctt aag aat agt gac tta agt ttt        912
Glu Ile Glu Asn Asn Thr Leu Lys Leu Lys Asn Ser Asp Leu Ser Phe
290                 295                 300 aat aat aaa gcg tta aaa gat cat aat gat gag tta act gaa gag ttg        960
Asn Asn Lys Ala Leu Lys Asp His Asn Asp Glu Leu Thr Glu Glu Leu
305                 310                 315                 320 agt aat gct aaa gag aaa cta cgt cac cac cac cac cac cac tga         1005
Ser Asn Ala Lys Glu Lys Leu Arg His His His His His His
                325                 330
```

<210> SEQ ID NO 2
<211> LENGTH: 334
<212> TYPE: PRT
<213> ORGANISM: Artificial Sequence
<220> FEATURE:
<223> OTHER INFORMATION: Description of Artificial Sequence: Hybrid of
      Group A Streptococci M protein and M-like protein

<400>

-continued

```
        35                  40                  45

Leu Thr Glu Glu Leu Ser Asn Ala Lys Glu Lys Leu Arg His Val Ala
    50                  55                  60

Val Thr Arg Gly Thr Ile Asn Asp Pro Gln Arg Ala Lys Glu Ala Leu
65                  70                  75                  80

Asp Lys Tyr Glu Leu Glu Asn His Asp Leu Lys Thr Lys Gly Ser Arg
                85                  90                  95

Val Phe Pro Arg Gly Thr Val Glu Asn Pro Asp Lys Ala Arg Glu Leu
            100                 105                 110

Leu Asn Lys Tyr Asp Val Glu Asn Ser Met Leu Gln Ala Asn Asn Asp
        115                 120                 125

Lys Leu Pro Trp Arg Val Arg Tyr Thr Arg His Thr Pro Glu Asp Lys
    130                 135                 140

Leu Lys Lys Ile Ile Asp Asp Leu Asp Ala Lys Glu His Glu Leu Gln
145                 150                 155                 160

Gln Gln Asn Glu Lys Leu Ser Leu Gln Lys Val Tyr Ile Thr Arg Gly
                165                 170                 175

Met Thr Lys Glu Asp Val Glu Lys Ile Ala Asn Asn Leu Asp Ile Glu
            180                 185                 190

Asn His Gly Leu Lys Gln Gln Asn Glu Gln Leu Ser Thr Asp Lys Gln
        195                 200                 205

Gly Leu Glu Glu Gln Asn Gly Thr Asp Arg Val Ser Arg Ser Met Ser
    210                 215                 220

Arg Asp Asp Leu Leu Asn Arg Ala Gln Asp Leu Glu Ala Lys Asn His
225                 230                 235                 240

Gly Leu Glu His Gln Asn Thr Lys Leu Ser Thr Glu Asn Lys Thr Leu
                245                 250                 255

Gln Glu Gln Ala Glu Ala Arg Gln Lys Glu Ile Asp Val Ala Thr Arg
            260                 265                 270

Ser Gln Thr Asp Thr Leu Glu Lys Val Gln Glu Arg Ala Asp Lys Phe
        275                 280                 285

Glu Ile Glu Asn Asn Thr Leu Lys Leu Lys Asn Ser Asp Leu Ser Phe
    290                 295                 300

Asn Asn Lys Ala Leu Lys Asp His Asn Asp Glu Leu Thr Glu Glu Leu
305                 310                 315                 320

Ser Asn Ala Lys Glu Lys Leu Arg His His His His His His
                325                 330

<210> SEQ ID NO 3
<211> LENGTH: 1107
<212> TYPE: DNA
<213> ORGANISM: Artificial Sequence
<220> FEATURE:
<221> NAME/KEY: CDS
<222> LOCATION: (1)..(1104)
<220> FEATURE:
<223> OTHER INFORMATION: Description of Artificial Sequence: Hybrid of
      Group A Streptococci M protein and M-like protein

<400> SEQUENCE: 3 atg agt aag aac cct gtc cct gtc aaa aaa gaa gca aaa tta agt gaa       48
Met Ser Lys Asn Pro Val Pro Val Lys Lys Glu Ala Lys Leu Ser Glu
  1               5                  10                  15 gca gaa tta cat gac aaa att aaa aac ctt gaa gag gaa aaa gca gaa       96
Ala Glu Leu His Asp Lys Ile Lys Asn Leu Glu Glu Glu Lys Ala Glu
            20                  25                  30 tta ttc gag aaa ctc gac gaa gaa cac cct gac gtt gtc gct gct aga      144
```

|     |     |     |     |     |     |     |     |     |     |     |     |     |     |     |     |
|---|---|---|---|---|---|---|---|---|---|---|---|---|---|---|---|
| Leu | Phe | Glu | Lys | Leu | Asp | Glu | Glu | His | Pro | Asp | Val | Val | Ala | Ala | Arg |
|     |     | 35  |     |     |     | 40  |     |     |     | 45  |     |     |     |     |     |

```
gaa agc gta cta aat aat gtc cgt gta ccg ggt aca ctt tgg cta cgt       192
Glu Ser Val Leu Asn Asn Val Arg Val Pro Gly Thr Leu Trp Leu Arg
     50              55                  60 caa aaa gaa gaa aat gac aaa ctt aaa ttg gaa aag aaa ggg ctt gag       240
Gln Lys Glu Glu Asn Asp Lys Leu Lys Leu Glu Lys Lys Gly Leu Glu
 65              70                  75                  80 act gag tta cag gaa aag gaa caa gct agc gaa gaa gca tca aat aat       288
Thr Glu Leu Gln Glu Lys Glu Gln Ala Ser Glu Glu Ala Ser Asn Asn
                 85                  90                  95 ggg caa ctc aca tta cag cat aaa aat aat gca ttg act agt gag aat       336
Gly Gln Leu Thr Leu Gln His Lys Asn Asn Ala Leu Thr Ser Glu Asn
             100                 105                 110 gag tct ctt cgt cgt gaa aaa gat cgt tat ttg tat gaa aaa gaa gaa       384
Glu Ser Leu Arg Arg Glu Lys Asp Arg Tyr Leu Tyr Glu Lys Glu Glu
         115                 120                 125 tta gaa gga tcc gag tca tca aat aat gcg gag tca tca aac att tct       432
Leu Glu Gly Ser Glu Ser Ser Asn Asn Ala Glu Ser Ser Asn Ile Ser
     130                 135                 140 caa gaa agc aaa cta ata aat aca ttg act gat gaa aat gag aaa ctc       480
Gln Glu Ser Lys Leu Ile Asn Thr Leu Thr Asp Glu Asn Glu Lys Leu
145                 150                 155                 160 aga gaa gag ctc caa cag tat tat gca tta agt gat gct aaa gaa gaa       528
Arg Glu Glu Leu Gln Gln Tyr Tyr Ala Leu Ser Asp Ala Lys Glu Glu
                 165                 170                 175 gaa cct cgt tat aaa gca ctg cag act gaa gtt aag gct gcg ggg caa       576
Glu Pro Arg Tyr Lys Ala Leu Gln Thr Glu Val Lys Ala Ala Gly Gln
             180                 185                 190 agc gct cct aaa ggt aca aac gtg agc gca gac cta tat aat tcg cta       624
Ser Ala Pro Lys Gly Thr Asn Val Ser Ala Asp Leu Tyr Asn Ser Leu
         195                 200                 205 tgg gat gaa aat aaa act ctt aga gaa aaa caa gaa gag tat ata aca       672
Trp Asp Glu Asn Lys Thr Leu Arg Glu Lys Gln Glu Glu Tyr Ile Thr
     210                 215                 220 aaa att caa aat gaa gag aca aaa aat aaa ggt acc gaa caa gca aaa       720
Lys Ile Gln Asn Glu Glu Thr Lys Asn Lys Gly Thr Glu Gln Ala Lys
225                 230                 235                 240 aat aat aat ggg gaa ctc aca tta cag caa aaa tac gat gca ttg act       768
Asn Asn Asn Gly Glu Leu Thr Leu Gln Gln Lys Tyr Asp Ala Leu Thr
                 245                 250                 255 aat gag aat aag tct ctt cgt cgt gag cgt gat aac tat tta aat tat       816
Asn Glu Asn Lys Ser Leu Arg Arg Glu Arg Asp Asn Tyr Leu Asn Tyr
             260                 265                 270 tta tat gaa aaa cca tgg gaa gag cat gaa aaa gta aca caa gcc aga       864
Leu Tyr Glu Lys Pro Trp Glu Glu His Glu Lys Val Thr Gln Ala Arg
         275                 280                 285 gaa gcg gtt atc aga gag atg caa cag agg ggg aca aat ttt gga cct       912
Glu Ala Val Ile Arg Glu Met Gln Gln Arg Gly Thr Asn Phe Gly Pro
     290                 295                 300 ctg tta gca agt aca atg cga gat aat cac aat tta aaa gaa acg ctt       960
Leu Leu Ala Ser Thr Met Arg Asp Asn His Asn Leu Lys Glu Thr Leu
305                 310                 315                 320 gac aaa act cac gtg agt aag aac cct gtc cct gtc aaa aaa gaa gca      1008
Asp Lys Thr His Val Ser Lys Asn Pro Val Pro Val Lys Lys Glu Ala
                 325                 330                 335 aaa tta agt gaa gca gaa tta cat gac aaa att aaa aac ctt gaa gag      1056
Lys Leu Ser Glu Ala Glu Leu His Asp Lys Ile Lys Asn Leu Glu Glu
             340                 345                 350
```

```
gaa aaa gca gaa tta ttc gag aaa ctc gag cac cac cac cac cac cac     1104
Glu Lys Ala Glu Leu Phe Glu Lys Leu Glu His His His His His His
        355                 360                 365 tga                                                                  1107
```

<210> SEQ ID NO 4
<211> LENGTH: 368
<212> TYPE: PRT
<213> ORGANISM: Artificial Sequence
<220> FEATURE:
<223> OTHER INFORMATION: Description of Artificial Sequence: Hybrid of
      Group A Streptococci M protein and M-like protein

<400> SEQUENCE: 4

Met Ser Lys Asn Pro Val Pro Val Lys Lys Glu Ala Lys Leu Ser Glu
1 5 10 15

Ala Glu Leu His Asp Lys Ile Lys Asn Leu Glu Glu Glu Lys Ala Glu
20 25 30

Leu Phe Glu Lys Leu Asp Glu Glu His Pro Asp Val Val Ala Ala Arg
35 40 45

Glu Ser Val Leu Asn Asn Val Arg Val Pro Gly Thr Leu Trp Leu Arg
50 55 60

Gln Lys Glu Glu Asn Asp Lys Leu Lys Leu Glu Lys Lys Gly Leu Glu
65 70 75 80

Thr Glu Leu Gln Glu Lys Glu Gln Ala Ser Glu Glu Ala Ser Asn Asn
85 90 95

Gly Gln Leu Thr Leu Gln His Lys Asn Asn Ala Leu Thr Ser Glu Asn
100 105 110

Glu Ser Leu Arg Arg Glu Lys Asp Arg Tyr Leu Tyr Glu Lys Glu Glu
115 120 125

Leu Glu Gly Ser Glu Ser Ser Asn Asn Ala Glu Ser Ser Asn Ile Ser
130 135 140

Gln Glu Ser Lys Leu Ile Asn Thr Leu Thr Asp Glu Asn Glu Lys Leu
145 150 155 160

Arg Glu Glu Leu Gln Gln Tyr Tyr Ala Leu Ser Asp Ala Lys Glu Glu
165 170 175

Glu Pro Arg Tyr Lys Ala Leu Gln Thr Glu Val Lys Ala Ala Gly Gln
180 185 190

Ser Ala Pro Lys Gly Thr Asn Val Ser Ala Asp Leu Tyr Asn Ser Leu
195 200 205

Trp Asp Glu Asn Lys Thr Leu Arg Glu Lys Gln Glu Glu Tyr Ile Thr
210 215 220

Lys Ile Gln Asn Glu Glu Thr Lys Asn Lys Gly Thr Glu Gln Ala Lys
225 230 235 240

Asn Asn Asn Gly Glu Leu Thr Leu Gln Gln Lys Tyr Asp Ala Leu Thr
245 250 255

Asn Glu Asn Lys Ser Leu Arg Arg Glu Arg Asp Asn Tyr Leu Asn Tyr
260 265 270

Leu Tyr Glu Lys Pro Trp Glu Glu His Glu Lys Val Thr Gln Ala Arg
275 280 285

Glu Ala Val Ile Arg Glu Met Gln Gln Arg Gly Thr Asn Phe Gly Pro
290 295 300

Leu Leu Ala Ser Thr Met Arg Asp Asn His Asn Leu Lys Glu Thr Leu
305 310 315 320

Asp Lys Thr His Val Ser Lys Asn Pro Val Pro Val Lys Lys Glu Ala
325 330 335

```
Lys Leu Ser Glu Ala Glu Leu His Asp Lys Ile Lys Asn Leu Glu Glu
            340                 345                 350

Glu Lys Ala Glu Leu Phe Glu Lys Leu Glu His His His His His His
        355                 360                 365

<210> SEQ ID NO 5
<211> LENGTH: 1209
<212> TYPE: DNA
<213> ORGANISM: Artificial Sequence
<220> FEATURE:
<221> NAME/KEY: CDS
<222> LOCATION: (1)..(1206)
<220> FEATURE:
<223> OTHER INFORMATION: Description of Artificial Sequence: Nucleic
      acid encoding Hybrid of Group A Streptococci M protein
      and M-like protein

<400> SEQUENCE: 5 atg agt gac aat att aat cgt tct gtc tct gtc aaa gat aat gaa aaa        48
Met Ser Asp Asn Ile Asn Arg Ser Val Ser Val Lys Asp Asn Glu Lys
 1               5

-continued

| | | | | | | | | | | | | | | |
|---|---|---|---|---|---|---|---|---|---|---|---|---|---|---|
| Leu | Asp | Lys | Phe | Asn | Thr | Glu | Gln | Gly | Lys | Thr | Thr | Arg | Leu | Glu | Glu |
| 225 | | | | 230 | | | | | 235 | | | | | 240 | |

```
caa aat aag ctt gcg gac gcg aac tcg aaa agc gtt tct aat agt aac     768
Gln Asn Lys Leu Ala Asp Ala Asn Ser Lys Ser Val Ser Asn Ser Asn
                245                 250                 255 gtg agc ata aat cta tat aat gag cta cag gct gaa cat gat aag cta     816
Val Ser Ile Asn Leu Tyr Asn Glu Leu Gln Ala Glu His Asp Lys Leu
            260                 265                 270 cag act aaa cat gag gag cta ttg gct gaa cat gat gct ctt aaa gaa     864
Gln Thr Lys His Glu Glu Leu Leu Ala Glu His Asp Ala Leu Lys Glu
        275                 280                 285 aaa caa gat aaa aat caa gaa ttc gat gac cgg agc gtt tct act aat     912
Lys Gln Asp Lys Asn Gln Glu Phe Asp Asp Arg Ser Val Ser Thr Asn
    290                 295                 300 agt ggt agc gtg agc aca cca tat aat aac cta ttg aat gaa tat gat     960
Ser Gly Ser Val Ser Thr Pro Tyr Asn Asn Leu Leu Asn Glu Tyr Asp
305                 310                 315                 320 gac cta ttg gct aaa cat ggt gag cta ttg agt gaa tat gat gct ctt    1008
Asp Leu Leu Ala Lys His Gly Glu Leu Leu Ser Glu Tyr Asp Ala Leu
                325                 330                 335 aaa gaa aaa caa gat aaa aat caa gaa gct agc agt gac aat att aat    1056
Lys Glu Lys Gln Asp Lys Asn Gln Glu Ala Ser Ser Asp Asn Ile Asn
            340                 345                 350 cgt tct gtc tct gtc aaa gat aat gaa aaa gaa tta cat aac aaa att    1104
Arg Ser Val Ser Val Lys Asp Asn Glu Lys Glu Leu His Asn Lys Ile
        355                 360                 365 gca gac ctt gaa gag gaa agg ggt gaa cat cta gac aaa ata gat gaa    1152
Ala Asp Leu Glu Glu Glu Arg Gly Glu His Leu Asp Lys Ile Asp Glu
    370                 375                 380 cta aaa gaa gaa cta aaa gca aag gaa aaa agt tca cac cac cac cac    1200
Leu Lys Glu Glu Leu Lys Ala Lys Glu Lys Ser Ser His His His His
385                 390                 395                 400 cac cac tga                                                         1209
His His <210> SEQ ID NO 6
<211> LENGTH: 402
<212> TYPE: PRT
<213> ORGANISM: Artificial Sequence
<220> FEATURE:
<223> OTHER INFORMATION: Description of Artificial Sequence: Hybrid of
      Group A Streptococci M protein and M-like protein

<400> SEQUENCE: 6

Met Ser Asp Asn Ile Asn Arg Ser Val Ser Val Lys Asp Asn Glu Lys
1               5                  10                  15

Glu Leu His Asn Lys Ile Ala Asp Leu Glu Glu Glu Arg Gly Glu His
            20                  25                  30

```
            115                 120                 125
Leu Leu Asn Lys Leu Asp Lys Val Glu Glu His Lys Lys Asp His
    130                 135                 140
Glu Gln Gly Thr Asn Ser Lys Asn Pro Ala Pro Ala Pro Ala Ser Ala
145                 150                 155                 160
Val Pro Val Lys Lys Glu Ala Thr Lys Leu Ser Glu Ala Glu Leu Tyr
                165                 170                 175
Asn Lys Ile Gln Glu Leu Glu Glu Gly Lys Ala Glu Leu Phe Gly Ser
            180                 185                 190
Glu Glu Glu Arg Thr Phe Thr Glu Leu Pro Tyr Glu Ala Arg Tyr Lys
        195                 200                 205
Ala Trp Lys Ser Glu Asn Asp Glu Leu Arg Glu Asn Tyr Arg Arg Thr
    210                 215                 220
Leu Asp Lys Phe Asn Thr Glu Gln Gly Lys Thr Thr Arg Leu Glu Glu
225                 230                 235                 240
Gln Asn Lys Leu Ala Asp Ala Asn Ser Lys Ser Val Ser Asn Ser Asn
                245                 250                 255
Val Ser Ile Asn Leu Tyr Asn Glu Leu Gln Ala Glu His Asp Lys Leu
            260                 265                 270
Gln Thr Lys His Glu Glu Leu Leu Ala Glu His Asp Ala Leu Lys Glu
        275                 280                 285
Lys Gln Asp Lys Asn Gln Glu Phe Asp Asp Arg Ser Val Ser Thr Asn
    290                 295                 300
Ser Gly Ser Val Ser Thr Pro Tyr Asn Asn Leu Leu Asn Glu Tyr Asp
305                 310                 315                 320
Asp Leu Leu Ala Lys His Gly Glu Leu Leu Ser Glu Tyr Asp Ala Leu
                325                 330                 335
Lys Glu Lys Gln Asp Lys Asn Gln Glu Ala Ser Ser Asp Asn Ile Asn
            340                 345                 350
Arg Ser Val Ser Val Lys Asp Asn Glu Lys Glu Leu His Asn Lys Ile
        355                 360                 365
Ala Asp Leu Glu Glu Glu Arg Gly Glu His Leu Asp Lys Ile Asp Glu
    370                 375                 380
Leu Lys Glu Glu Leu Lys Ala Lys Glu Lys Ser Ser His His His His
385                 390                 395                 400
His His
```

```
<210> SEQ ID NO 7
<211> LENGTH: 1287
<212> TYPE: DNA
<213> ORGANISM: Artificial Sequence
<220> FEATURE:
<221> NAME/KEY: CDS
<222> LOCATION: (1)..(1284)
<220> FEATURE:
<223> OTHER INFORMATION: Description of Artificial Sequence: Hybrid of
      Group A Streptococci M protein and M-like protein

<400> SEQUENCE: 7 atg aac ggt gat ggt aat cct agg gaa gtt ata gaa gat ctt gca gca      48
Met Asn Gly Asp Gly Asn Pro Arg Glu Val Ile Glu Asp Leu Ala Ala
  1               5

```
                35                  40                  45
aag aga gct ctc gac gat cat agt gat tta gtc gca gaa aaa caa cgt    192
Lys Arg Ala Leu Asp Asp His Ser Asp Leu Val Ala Glu Lys Gln Arg
     50                  55                  60 tta gaa gat tta gga caa aaa ttt gaa aga ctg aaa cag cgt tca gaa    240
Leu Glu Asp Leu Gly Gln Lys Phe Glu Arg Leu Lys Gln Arg Ser Glu
 65                  70                  75                  80 ctc tac ctt cag caa tac tat gat aat aaa tca aat gga tat aaa ggt    288
Leu Tyr Leu Gln Gln Tyr Tyr Asp Asn Lys Ser Asn Gly Tyr Lys Gly
                 85                  90                  95 gac tgg tat gta caa cag tta gga tcc gat tca gta agt gga tta gag    336
Asp Trp Tyr Val Gln Gln Leu Gly Ser Asp Ser Val Ser Gly Leu Glu
            100                 105                 110 gtg gca gac ccc tct gat agt aag aaa ctt att gaa tta ggt ttg gct    384
Val Ala Asp Pro Ser Asp Ser Lys Lys Leu Ile Glu Leu Gly Leu Ala
        115                 120                 125 aaa tac ctt aat gat aaa tta ccc ttt aaa act aaa gaa gat tca gag    432
Lys Tyr Leu Asn Asp Lys Leu Pro Phe Lys Thr Lys Glu Asp Ser Glu
    130                 135                 140 att tta tca gag tta cgt gat gta tta aaa aat ctg cag gag tct cca    480
Ile Leu Ser Glu Leu Arg Asp Val Leu Lys Asn Leu Gln Glu Ser Pro
145                 150                 155                 160 aaa agt act gag act tct gct aat gga gct gat aaa tta gct gat gca    528
Lys Ser Thr Glu Thr Ser Ala Asn Gly Ala Asp Lys Leu Ala Asp Ala
                165                 170                 175 tac aac aca ttg ctt act gaa cat gag aaa ctc aga gat gag tat tat    576
Tyr Asn Thr Leu Leu Thr Glu His Glu Lys Leu Arg Asp Glu Tyr Tyr
            180                 185                 190 aca tta att gat gct aaa gaa gaa gaa cct cgc tat aaa gca ttg ggt    624
Thr Leu Ile Asp Ala Lys Glu Glu Glu Pro Arg Tyr Lys Ala Leu Gly
        195                 200                 205 acc ttg tta gat cag gtt aca caa tta tat act aaa cat aat agt aat    672
Thr Leu Leu Asp Gln Val Thr Gln Leu Tyr Thr Lys His Asn Ser Asn
    210                 215                 220 tac caa caa tat aat gca caa gct ggc aga ctt gac ctg aga caa aag    720
Tyr Gln Gln Tyr Asn Ala Gln Ala Gly Arg Leu Asp Leu Arg Gln Lys
225                 230                 235                 240 gct gaa tat cta aaa ggc ctt aat gat tgg gct gag cgc ctg tta caa    768
Ala Glu Tyr Leu Lys Gly Leu Asn Asp Trp Ala Glu Arg Leu Leu Gln
                245                 250                 255 gag tta aat ggt acc aac aat gat ggt cgt tct cgt gac gtt acg gaa    816
Glu Leu Asn Gly Thr Asn Asn Asp Gly Arg Ser Arg Asp Val Thr Glu
            260                 265                 270 gag att gca gca aac aat acc aca gta caa aat ata cgt tta cgt aac    864
Glu Ile Ala Ala Asn Asn Thr Thr Val Gln Asn Ile Arg Leu Arg Asn
        275                 280                 285 gaa aac aag aac tta aaa gcg aaa aac gag gac tta gaa gcg aga tta    912
Glu Asn Lys Asn Leu Lys Ala Lys Asn Glu Asp Leu Glu Ala Arg Leu
    290                 295                 300 gag aat gca atg aat gtt gca gga cgc gat ttt aag cgt gct gaa ttc    960
Glu Asn Ala Met Asn Val Ala Gly Arg Asp Phe Lys Arg Ala Glu Phe
305                 310                 315                 320 gca cct ctt act cgt gct aca gca gac aat aaa gac gaa tta ata aaa    1008
Ala Pro Leu Thr Arg Ala Thr Ala Asp Asn Lys Asp Glu Leu Ile Lys
                325                 330                 335 aga gct aac ggt tat gag ata cag aac cat cag tta aca gtt gag aat    1056
Arg Ala Asn Gly Tyr Glu Ile Gln Asn His Gln Leu Thr Val Glu Asn
            340                 345                 350 aaa aaa tta aaa act gat aag gaa cag tta aca aaa gag aat gat gat    1104
```

```
Lys Lys Leu Lys Thr Asp Lys Glu Gln Leu Thr Lys Glu Asn Asp Asp
        355                 360                 365 tta aaa cac gtg aac ggt gat ggt aat cct cgt gaa gtt ata gaa gat       1152
Leu Lys His Val Asn Gly Asp Gly Asn Pro Arg Glu Val Ile Glu Asp
        370                 375                 380 ctt gca gca aac aat ccc gca ata caa aat ata cgt tta cgt cac gaa       1200
Leu Ala Ala Asn Asn Pro Ala Ile Gln Asn Ile Arg Leu Arg His Glu
385                 390                 395                 400 aac aag gac tta aaa gcg aga tta gag aat gca atg gaa gtt gca gga       1248
Asn Lys Asp Leu Lys Ala Arg Leu Glu Asn Ala Met Glu Val Ala Gly
                405                 410                 415 cgt gat ttt aag cgt gct cac cac cac cac cac cac taa                   1287
Arg Asp Phe Lys Arg Ala His His His His His His
                420                 425

<210> SEQ ID NO 8
<211> LENGTH: 428
<212> TYPE: PRT
<213> ORGANISM: Artificial Sequence
<220> FEATURE:
<223> OTHER INFORMATION: Description of Artificial Sequence: Hybrid of
      Group A Streptococci M protein and M-like protein

<400> SEQUENCE: 8

Met Asn Gly Asp Gly Asn Pro Arg Glu Val Ile Glu Asp Leu Ala Ala
1               5                   10                  15

Asn Asn Pro Ala Ile Gln Asn Ile Arg Leu Arg His Glu Asn Lys Asp
            20                  25                  30

Leu Lys Ala Arg Leu Glu Asn Ala Met Glu Val Ala Gly Arg Asp Phe
        35                  40                  45

Lys Arg Ala Leu Asp Asp His Ser Asp Leu Val Ala Glu Lys Gln Arg
    50                  55                  60

Leu Glu Asp Leu Gly Gln Lys Phe Glu Arg Leu Lys Gln Arg Ser Glu
65                  70                  75                  80

Leu Tyr Leu Gln Gln Tyr Tyr Asp Asn Lys Ser Asn Gly Tyr Lys Gly
                85                  90                  95

Asp Trp Tyr Val Gln Gln Leu Gly Ser Asp Ser Val Ser Gly Leu Glu
            100                 105                 110

Val Ala Asp Pro Ser Asp Ser Lys Lys Leu Ile Glu Leu Gly Leu Ala
        115                 120                 125

Lys Tyr Leu Asn Asp Lys Leu Pro Phe Lys Thr Lys Glu Asp Ser Glu
    130                 135                 140

Ile Leu Ser Glu Leu Arg Asp Val Leu Lys Asn Leu Gln Glu Ser Pro
145                 150                 155                 160

Lys Ser Thr Glu Thr Ser Ala Asn Gly Ala Asp Lys Leu Ala Asp Ala
                165                 170                 175

Tyr Asn Thr Leu Leu Thr Glu His Glu Lys Leu Arg Asp Glu Tyr Tyr
            180                 185                 190

Thr Leu Ile Asp Ala Lys Glu Glu Pro Arg Tyr Lys Ala Leu Gly
        195                 200                 205

Thr Leu Leu Asp Gln Val Thr Gln Leu Tyr Thr Lys His Asn Ser Asn
    210                 215                 220

Tyr Gln Gln Tyr Asn Ala Gln Ala Gly Arg Leu Asp Leu Arg Gln Lys
225                 230                 235                 240

Ala Glu Tyr Leu Lys Gly Leu Asn Asp Trp Ala Glu Arg Leu Leu Gln
                245                 250                 255

Glu Leu Asn Gly Thr Asn Asn Asp Gly Arg Ser Arg Asp Val Thr Glu
```

```
                        260                 265                 270
Glu Ile Ala Ala Asn Asn Thr Thr Val Gln Asn Ile Arg Leu Arg Asn
                275                 280                 285
Glu Asn Lys Asn Leu Lys Ala Lys Asn Glu Asp Leu Glu Ala Arg Leu
            290                 295                 300
Glu Asn Ala Met Asn Val Ala Gly Arg Asp Phe Lys Arg Ala Glu Phe
305                 310                 315                 320
Ala Pro Leu Thr Arg Ala Thr Ala Asp Asn Lys Asp Glu Leu Ile Lys
                325                 330                 335
Arg Ala Asn Gly Tyr Glu Ile Gln Asn His Gln Leu Thr Val Glu Asn
            340                 345                 350
Lys Lys Leu Lys Thr Asp Lys Glu Gln Leu Thr Lys Glu Asn Asp Asp
        355                 360                 365
Leu Lys His Val Asn Gly Asp Gly Asn Pro Arg Glu Val Ile Glu Asp
        370                 375                 380
Leu Ala Ala Asn Asn Pro Ala Ile Gln Asn Ile Arg Leu Arg His Glu
385                 390                 395                 400
Asn Lys Asp Leu Lys Ala Arg Leu Glu Asn Ala Met Glu Val Ala Gly
                405                 410                 415
Arg Asp Phe Lys Arg Ala His His His His His His
                420                 425

<210> SEQ ID NO 9
<211> LENGTH: 1008
<212> TYPE: DNA
<213> ORGANISM: Artificial Sequence
<220> FEATURE:
<221> NAME/KEY: CDS
<222> LOCATION: (1)..(1005)
<220> FEATURE:
<223> OTHER INFORMATION: Description of Artificial Sequence: Nucleic
      acid encoding Hybrid of Group A Streptococci M protein
      and M-like protein

<400> SEQUENCE: 9 atg gtc gcg act agg tct cag aca gat act ctg gaa aaa gta caa gaa     48
Met Val Ala Thr Arg Ser Gln Thr Asp Thr Leu Glu Lys Val G -continued

```
aag tta cca tgg aga gtg cgt tat act agg cat acg cca gaa gat aag      432
Lys Leu Pro Trp Arg Val Arg Tyr Thr Arg His Thr Pro Glu Asp Lys
    130                 135                 140 cta aaa aaa att att gac gat ctt gac gca aaa gaa cat gaa tta caa      480
Leu Lys Lys Ile Ile Asp Asp Leu Asp Ala Lys Glu His Glu Leu Gln
145                 150                 155                 160 caa cag aat gag aag tta tct ctg cag aaa gtg tat att act agg ggt      528
Gln Gln Asn Glu Lys Leu Ser Leu Gln Lys Val Tyr Ile Thr Arg Gly
                165                 170                 175 atg aca aaa gag gac gta gaa aaa att gct aac aac ctt gac ata gaa      576
Met Thr Lys Glu Asp Val Glu Lys Ile Ala Asn Asn Leu Asp Ile Glu
            180                 185                 190 aac cat ggg tta aaa caa cag aat gaa cag tta tct act gat aaa caa      624
Asn His Gly Leu Lys Gln Gln Asn Glu Gln Leu Ser Thr Asp Lys Gln
        195                 200                 205 ggt ctt gaa gaa cag aat ggt acc gat aga gtt agt agg tct atg tca      672
Gly Leu Glu Glu Gln Asn Gly Thr Asp Arg Val Ser Arg Ser Met Ser
    210                 215                 220 aga gat gat cta tta aac agg gct cag gat ctt gaa gca aaa aac cac      720
Arg Asp Asp Leu Leu Asn Arg Ala Gln Asp Leu Glu Ala Lys Asn His
225                 230                 235                 240 ggg tta gaa cac cag aat act aag tta tct act gaa aat aaa acg ctt      768
Gly Leu Glu His Gln Asn Thr Lys Leu Ser Thr Glu Asn Lys Thr Leu
                245                 250                 255 caa gaa caa gca gaa gca cgc cag aaa gaa atc gat gtc gcg act agg      816
Gln Glu Gln Ala Glu Ala Arg Gln Lys Glu Ile Asp Val Ala Thr Arg
            260                 265                 270 tct cag aca gat act ctg gaa aaa gta caa gaa cgt gct gac aag ttt      864
Ser Gln Thr Asp Thr Leu Glu Lys Val Gln Glu Arg Ala Asp Lys Phe
        275                 280                 285 gag ata gaa aac aat acg tta aaa ctt aag aat agt gac tta agt ttt      912
Glu Ile Glu Asn Asn Thr Leu Lys Leu Lys Asn Ser Asp Leu Ser Phe
    290                 295                 300 aat aat aaa gcg tta aaa gat cat aat gat gag tta act gaa gag ttg      960
Asn Asn Lys Ala Leu Lys Asp His Asn Asp Glu Leu Thr Glu Glu Leu
305                 310                 315                 320 agt aat gct aaa gag aaa cta cgt cac cac cac cac cac cac tgc tga     1008
Ser Asn Ala Lys Glu Lys Leu Arg His His His His His His Cys
                325                 330                 335

<210> SEQ ID NO 10
<211> LENGTH: 335
<212> TYPE: PRT
<213> ORGANISM: Artificial Sequence
<220> FEATURE:
<223> OTHER INFORMATION: Description of Artificial Sequence: Hybrid of
      Group A Streptococci M protein and M-like protein

<400> SEQUENCE: 10

Met Val Ala Thr Arg Ser Gln Thr Asp Thr Leu Glu Lys Val Gln Glu
  1               5                  10                  15

Arg Ala Asp Lys Phe Glu Ile Glu Asn Asn Thr Leu Lys Leu Lys Asn
             20                  25                  30

Ser Asp Leu Ser Phe Asn Asn Lys Ala Leu Lys Asp His Asn Asp Glu
        35                  40                  45

Leu Thr Glu Glu Leu Ser Asn Ala Lys Glu Lys Leu Arg His Val Ala
     50                  55                  60

Val Thr Arg Gly Thr Ile Asn Asp Pro Gln Arg Ala Lys Glu Ala Leu
 65                  70                  75                  80

Asp Lys Tyr Glu Leu Glu Asn His Asp Leu Lys Thr Lys Gly Ser Arg
```

-continued

```
                    85                  90                  95
Val Phe Pro Arg Gly Thr Val Glu Asn Pro Asp Lys Ala Arg Glu Leu
            100                 105                 110

Leu Asn Lys Tyr Asp Val Glu Asn Ser Met Leu Gln Ala Asn Asn Asp
            115                 120                 125

Lys Leu Pro Trp Arg Val Arg Tyr Thr Arg His Thr Pro Glu Asp Lys
            130                 135                 140

Leu Lys Lys Ile Ile Asp Asp Leu Asp Ala Lys Glu His Glu Leu Gln
145                 150                 155                 160

Gln Gln Asn Glu Lys Leu Ser Leu Gln Lys Val Tyr Ile Thr Arg Gly
                165                 170                 175

Met Thr Lys Glu Asp Val Glu Lys Ile Ala Asn Asn Leu Asp Ile Glu
            180                 185                 190

Asn His Gly Leu Lys Gln Gln Asn Glu Gln Leu Ser Thr Asp Lys Gln
            195                 200                 205

Gly Leu Glu Glu Gln Asn Gly Thr Asp Arg Val Ser Arg Ser Met Ser
    210                 215                 220

Arg Asp Asp Leu Leu Asn Arg Ala Gln Asp Leu Glu Ala Lys Asn His
225                 230                 235                 240

Gly Leu Glu His Gln Asn Thr Lys Leu Ser Thr Glu Asn Lys Thr Leu
                245                 250                 255

Gln Glu Gln Ala Glu Ala Arg Gln Lys Glu Ile Asp Val Ala Thr Arg
            260                 265                 270

Ser Gln Thr Asp Thr Leu Glu Lys Val Gln Glu Arg Ala Asp Lys Phe
            275                 280                 285

Glu Ile Glu Asn Asn Thr Leu Lys Leu Lys Asn Ser Asp Leu Ser Phe
    290                 295                 300

Asn Asn Lys Ala Leu Lys Asp His Asn Asp Glu Leu Thr Glu Glu Leu
305                 310                 315                 320

Ser Asn Ala Lys Glu Lys Leu Arg His His His His His Cys
                325                 330                 335
```

<210> SEQ ID NO 11
<211> LENGTH: 1194
<212> TYPE: DNA
<213> ORGANISM: Artificial Sequence
<220> FEATURE:
<221> NAME/KEY: CDS
<222> LOCATION: (1)..(1191)
<220> FEATURE:
<223> OTHER INFORMATION: Description of Artificial Sequence: Hybrid of Group A Streptococci M protein and M-like protein

<400>

-continued

```
         65                  70                  75                  80 aaa gaa gaa aat gac aaa ctt aaa ttg gaa aag aaa ggg ctt gag act         288
Lys Glu Glu Asn Asp Lys Leu Lys Leu Glu Lys Lys Gly Leu Glu Thr
                 85                  90                  95 gag tta cag gaa aag gaa caa gct agc gaa gaa gca tca aat aat ggg         336
Glu Leu Gln Glu Lys Glu Gln Ala Ser Glu Glu Ala Ser Asn Asn Gly
                100                 105                 110 caa ctc aca tta cag cat aaa aat aat gca ttg act agt gag aat gag         384
Gln Leu Thr Leu Gln His Lys Asn Asn Ala Leu Thr Ser Glu Asn Glu
            115                 120                 125 tct ctt aga aga gaa aaa gat aga tat ttg tat gaa aaa gaa gaa tta         432
Ser Leu Arg Arg Glu Lys Asp Arg Tyr Leu Tyr Glu Lys Glu Glu Leu
        130                 135                 140 gaa gga tcc gag tca tca aat aat gcg gag tca tca aac att tct caa         480
Glu Gly Ser Glu Ser Ser Asn Asn Ala Glu Ser Ser Asn Ile Ser Gln
145                 150                 155                 160 gaa agc aaa cta ata aat aca ttg act gat gaa aat gag aaa ctc aga         528
Glu Ser Lys Leu Ile Asn Thr Leu Thr Asp Glu Asn Glu Lys Leu Arg
                165                 170                 175 gaa gag ctc caa cag tat tat gca tta agt gat gct aaa gaa gaa gaa         576
Glu Glu Leu Gln Gln Tyr Tyr Ala Leu Ser Asp Ala Lys Glu Glu Glu
                180                 185                 190 cct agg tat aaa gca ctg cag act gaa gtt aag gct gcg ggg caa agc         624
Pro Arg Tyr Lys Ala Leu Gln Thr Glu Val Lys Ala Ala Gly Gln Ser
            195                 200                 205 gct cct aaa ggt aca aac gtg agc gca gac cta tat aat tcg cta tgg         672
Ala Pro Lys Gly Thr Asn Val Ser Ala Asp Leu Tyr Asn Ser Leu Trp
        210                 215                 220 gat gaa aat aaa act ctt aga gaa aaa caa gaa gag tat ata aca aaa         720
Asp Glu Asn Lys Thr Leu Arg Glu Lys Gln Glu Glu Tyr Ile Thr Lys
225                 230                 235                 240 att caa aat gaa gag aca aaa aat aaa ggt acc gaa caa gca aaa aat         768
Ile Gln Asn Glu Glu Thr Lys Asn Lys Gly Thr Glu Gln Ala Lys Asn
                245                 250                 255 aat aat ggg gaa ctc aca tta cag caa aaa tac gat gca ttg act aat         816
Asn Asn Gly Glu Leu Thr Leu Gln Gln Lys Tyr Asp Ala Leu Thr Asn
                260                 265                 270 gag aat aag tct ctt aga aga gag aga gat aac tat tta aat tat tta         864
Glu Asn Lys Ser Leu Arg Arg Glu Arg Asp Asn Tyr Leu Asn Tyr Leu
            275                 280                 285 tat gaa aaa cca tgg gaa gag cat gaa aaa gta aca caa gcc aga gaa         912
Tyr Glu Lys Pro Trp Glu Glu His Glu Lys Val Thr Gln Ala Arg Glu
        290                 295                 300 gcg gtt atc aga gag atg caa cag agg ggg aca aat ttt gga cct ctg         960
Ala Val Ile Arg Glu Met Gln Gln Arg Gly Thr Asn Phe Gly Pro Leu
305                 310                 315                 320 tta gca agt aca atg cga gat aat cac aat tta aaa gaa acg ctt gac        1008
Leu Ala Ser Thr Met Arg Asp Asn His Asn Leu Lys Glu Thr Leu Asp
                325                 330                 335 aaa act cac gtg agt aag aac cct gtc cct gtc aaa aaa gaa gca aaa        1056
Lys Thr His Val Ser Lys Asn Pro Val Pro Val Lys Lys Glu Ala Lys
                340                 345                 350 tta agt gaa gca gaa tta cat gac aaa att aaa aac ctt gaa gag gaa        1104
Leu Ser Glu Ala Glu Leu His Asp Lys Ile Lys Asn Leu Glu Glu Glu
            355                 360                 365 aaa gca gaa tta ttc gag aaa tta gat aaa gtt gaa gaa gag cat aaa        1152
Lys Ala Glu Leu Phe Glu Lys Leu Asp Lys Val Glu Glu Glu His Lys
        370                 375                 380 aaa gtt gaa gaa gag cat cac cac cac cac cac cac tgc taa              1194
```

Lys Val Glu Glu His His His His His His Cys
385                 390                 395

<210> SEQ ID NO 12
<211> LENGTH: 397
<212> TYPE: PRT
<213> ORGANISM: Artificial Sequence
<220> FEATURE:
<223> OTHER INFORMATION: Description of Artificial Sequence: Hybrid of
      Group A Streptococci M protein and M-like protein

<400> SEQUENCE: 12

Met Ser Lys Asn Pro Val Pro Val Lys Glu Ala Lys Leu Ser Glu
1               5                   10                  15

Ala Glu Leu His Asp Lys Ile Lys Asn Leu Glu Glu Glu Lys Ala Glu
                20                  25                  30

Leu Phe Glu Lys Leu Asp Lys Val Glu Glu His Lys Lys Val Glu
        35                  40                  45

Glu Glu His Val Asp Glu His Pro Asp Val Val Ala Ala Arg Glu
    50                  55                  60

Ser Val Leu Asn Asn Val Arg Val Pro Gly Thr Leu Trp Leu Arg Gln
65                  70                  75                  80

Lys Glu Glu Asn Asp Lys Leu Lys Leu Glu Lys Lys Gly Leu Glu Thr
                85                  90                  95

Glu Leu Gln Glu Lys Glu Gln Ala Ser Glu Ala Ser Asn Asn Gly
            100                 105                 110

Gln Leu Thr Leu Gln His Lys Asn Asn Ala Leu Thr Ser Glu Asn Glu
        115                 120                 125

Ser Leu Arg Arg Glu Lys Asp Arg Tyr Leu Tyr Glu Lys Glu Glu Leu
    130                 135                 140

Glu Gly Ser Glu Ser Ser Asn Asn Ala Glu Ser Ser Asn Ile Ser Gln
145                 150                 155                 160

Glu Ser Lys Leu Ile Asn Thr Leu Thr Asp Glu Asn Glu Lys Leu Arg
                165                 170                 175

Glu Glu Leu Gln Gln Tyr Tyr Ala Leu Ser Asp Ala Lys Glu Glu Glu
            180                 185                 190

Pro Arg Tyr Lys Ala Leu Gln Thr Glu Val Lys Ala Ala Gly Gln Ser
        195                 200                 205

Ala Pro Lys Gly Thr Asn Val Ser Ala Asp Leu Tyr Asn Ser Leu Trp
    210                 215                 220

Asp Glu Asn Lys Thr Leu Arg Glu Lys Gln Glu Glu Tyr Ile Thr Lys
225                 230                 235                 240

Ile Gln Asn Glu Glu Thr Lys Asn Lys Gly Thr Glu Gln Ala Lys Asn
                245                 250                 255

Asn Asn Gly Glu Leu Thr Leu Gln Gln Lys Tyr Asp Ala Leu Thr Asn
            260                 265                 270

Glu Asn Lys Ser Leu Arg Arg Glu Arg Asp Asn Tyr Leu Asn Tyr Leu
        275                 280                 285

Tyr Glu Lys Pro Trp Glu Glu His Glu Lys Val Thr Gln Ala Arg Glu
    290                 295                 300

Ala Val Ile Arg Glu Met Gln Gln Arg Gly Thr Asn Phe Gly Pro Leu
305                 310                 315                 320

Leu Ala Ser Thr Met Arg Asp Asn His Asn Leu Lys Glu Thr Leu Asp
                325                 330                 335

Lys Thr His Val Ser Lys Asn Pro Val Pro Val Lys Lys Glu Ala Lys
            340                 345                 350

```
Leu Ser Glu Ala Glu Leu His Asp Lys Ile Lys Asn Leu Glu Glu Glu
        355                 360                 365

Lys Ala Glu Leu Phe Glu Lys Leu Asp Lys Val Glu Glu His Lys
    370                 375                 380

Lys Val Glu Glu Glu His His His His His His Cys
385                 390                 395

<210> SEQ ID NO 13
<211> LENGTH: 1212
<212> TYPE: DNA
<213> ORGANISM: Artificial Sequence
<220> FEATURE:
<221> NAME/KEY: CDS
<222> LOCATION: (1)..(1209)
<220> FEATURE:
<223> OTHER INFORMATION: Description of Artificial Sequence: Nucleic
      acid encoding Hybrid of Group A Streptococci M protein
      and M-like protein

<400> SEQUENCE: 13 atg agt gac aat att aat aga tct gtc tct gtc aaa gat aat gaa aaa       48
Met Ser Asp Asn Ile Asn Arg Ser Val Ser Val Lys Asp Asn Glu Lys
1               5                   10                  15 gaa tta cat aac aaa att gca gac ctt gaa gag gaa agg ggt gaa cat       96
Glu Leu His Asn Lys Ile Ala Asp Leu Glu Glu Glu Arg Gly Glu His
            20                  25                  30 cta gac aaa ata gat gaa cta aaa gaa gaa cta aaa gca aag gaa aaa      144
Leu Asp Lys Ile Asp Glu Leu Lys Glu Glu Leu Lys Ala Lys Glu Lys
        35                  40                  45 agt tca gga tcc gct gat cac cct agc tat acc gct gct aaa gat gaa      192
Ser Ser Gly Ser Ala Asp His Pro Ser Tyr Thr Ala Ala Lys Asp Glu
    50                  55                  60 gta cta agt aag ttc tct gta ccg ggt cat gtt tgg gca cat gaa aga      240
Val Leu Ser Lys Phe Ser Val Pro Gly His Val Trp Ala His Glu Arg
65                  70                  75                  80 gaa aaa aat gac aaa ctt agc tcg gaa aat gaa ggg ctt aag gct ggt      288
Glu Lys Asn Asp Lys Leu Ser Ser Glu Asn Glu Gly Leu Lys Ala Gly
                85                  90                  95 tta cag gaa aag gaa caa gct agc gaa ggg gtt tct gta ggt tca gat      336
Leu Gln Glu Lys Glu Gln Ala Ser Glu Gly Val Ser Val Gly Ser Asp
            100                 105                 110 gca tca cta cat aac cgc att aca gac ctt gaa gag gaa aga gaa aaa      384
Ala Ser Leu His Asn Arg Ile Thr Asp Leu Glu Glu Glu Arg Glu Lys
        115                 120                 125 tta tta aat aaa tta gat aaa gtt gaa gaa gag cat aaa aaa gat cat      432
Leu Leu Asn Lys Leu Asp Lys Val Glu Glu Glu His Lys Lys Asp His
    130                 135                 140 gaa caa ggt acc aac agt aag aac cct gcc cct gcc cct gcc tct gct      480
Glu Gln Gly Thr Asn Ser Lys Asn Pro Ala Pro Ala Pro Ala Ser Ala
145                 150                 155                 160 gtc cct gtc aaa aaa gaa gca aca aaa tta agt gaa gca gaa tta tat      528
Val Pro Val Lys Lys Glu Ala Thr Lys Leu Ser Glu Ala Glu Leu Tyr
                165                 170                 175 aac aaa att caa gaa ctt gaa gag gga aaa gca gaa tta ttc gga tcc      576
Asn Lys Ile Gln Glu Leu Glu Glu Gly Lys Ala Glu Leu Phe Gly Ser
            180                 185                 190 gaa gaa gaa cgt act ttt act gag tta cca tat gaa gca cga tac aaa      624
Glu Glu Glu Arg Thr Phe Thr Glu Leu Pro Tyr Glu Ala Arg Tyr Lys
        195                 200                 205 gca tgg aaa agt gaa aat gat gag ctt cgg gaa aat tat aga agg acc      672
Ala Trp Lys Ser Glu Asn Asp Glu Leu Arg Glu Asn Tyr Arg Arg Thr
```

-continued

```
                        210                 215                 220
tta gat aag ttt aat act gag caa ggt aag act acg aga tta gaa gaa        720
Leu Asp Lys Phe Asn Thr Glu Gln Gly Lys Thr Thr Arg Leu Glu Glu
225                 230                 235                 240 caa aat aag ctt gcg gac gcg aac tcg aaa agc gtt tct aat agt aac        768
Gln Asn Lys Leu Ala Asp Ala Asn Ser Lys Ser Val Ser Asn Ser Asn
                245                 250                 255 gtg agc ata aat cta tat aat gag cta cag gct gaa cat gat aag cta        816
Val Ser Ile Asn Leu Tyr Asn Glu Leu Gln Ala Glu His Asp Lys Leu
            260                 265                 270 cag act aaa cat gag gag cta ttg gct gaa cat gat gct ctt aaa gaa        864
Gln Thr Lys His Glu Glu Leu Leu Ala Glu His Asp Ala Leu Lys Glu
        275                 280                 285 aaa caa gat aaa aat caa gaa ttc gat gac cgg agc gtt tct act aat        912
Lys Gln Asp Lys Asn Gln Glu Phe Asp Asp Arg Ser Val Ser Thr Asn
    290                 295                 300 agt ggt agc gtg agc aca cca tat aat aac cta ttg aat gaa tat gat        960
Ser Gly Ser Val Ser Thr Pro Tyr Asn Asn Leu Leu Asn Glu Tyr Asp
305                 310                 315                 320 gac cta ttg gct aaa cat ggt gag cta ttg agt gaa tat gat gct ctt       1008
Asp Leu Leu Ala Lys His Gly Glu Leu Leu Ser Glu Tyr Asp Ala Leu
                325                 330                 335 aaa gaa aaa caa gat aaa aat caa gaa gct agc agt gac aat att aat       1056
Lys Glu Lys Gln Asp Lys Asn Gln Glu Ala Ser Ser Asp Asn Ile Asn
                340                 345                 350 aga tct gtc tct gtc aaa gat aat gaa aaa gaa tta cat aac aaa att       1104
Arg Ser Val Ser Val Lys Asp Asn Glu Lys Glu Leu His Asn Lys Ile
            355                 360                 365 gca gac ctt gaa gag gaa agg ggt gaa cat cta gac aaa ata gat gaa       1152
Ala Asp Leu Glu Glu Glu Arg Gly Glu His Leu Asp Lys Ile Asp Glu
        370                 375                 380 cta aaa gaa gaa cta aaa gca aag gaa aaa agt tca cac cac cac cac       1200
Leu Lys Glu Glu Leu Lys Ala Lys Glu Lys Ser Ser His His His His
385                 390                 395                 400 cac cac tgc tga                                                       1212
His His Cys
```

<210> SEQ ID NO 14
<211> LENGTH: 403
<212> TYPE: PRT
<213> ORGANISM: Artificial Sequence
<220> FEATURE:
<223> OTHER INFORMATION: Description of Artificial Sequence: Hybrid of Group A Streptococci M protein and M-like protein

<400> SEQUENCE: 14

Met Ser

```
                    100                 105                 110
Ala Ser Leu His Asn Arg Ile Thr Asp Leu Glu Glu Arg Glu Lys
        115                 120                 125

Leu Leu Asn Lys Leu Asp Lys Val Glu Glu His Lys Lys Asp His
130                 135                 140

Glu Gln Gly Thr Asn Ser Lys Asn Pro Ala Pro Ala Pro Ser Ala
145                 150                 155                 160

Val Pro Val Lys Lys Glu Ala Thr Lys Leu Ser Glu Ala Glu Leu Tyr
                165                 170                 175

Asn Lys Ile Gln Glu Leu Glu Glu Gly Lys Ala Glu Leu Phe Gly Ser
            180                 185                 190

Glu Glu Glu Arg Thr Phe Thr Glu Leu Pro Tyr Glu Ala Arg Tyr Lys
        195                 200                 205

Ala Trp Lys Ser Glu Asn Asp Glu Leu Arg Glu Asn Tyr Arg Arg Thr
    210                 215                 220

Leu Asp Lys Phe Asn Thr Glu Gln Gly Lys Thr Thr Arg Leu Glu Glu
225                 230                 235                 240

Gln Asn Lys Leu Ala Asp Ala Asn Ser Lys Ser Val Ser Asn Ser Asn
                245                 250                 255

Val Ser Ile Asn Leu Tyr Asn Glu Leu Gln Ala Glu His Asp Lys Leu
            260                 265                 270

Gln Thr Lys His Glu Glu Leu Leu Ala Glu His Asp Ala Leu Lys Glu
        275                 280                 285

Lys Gln Asp Lys Asn Gln Glu Phe Asp Asp Arg Ser Val Ser Thr Asn
    290                 295                 300

Ser Gly Ser Val Ser Thr Pro Tyr Asn Asn Leu Leu Asn Glu Tyr Asp
305                 310                 315                 320

Asp Leu Leu Ala Lys His Gly Glu Leu Leu Ser Glu Tyr Asp Ala Leu
                325                 330                 335

Lys Glu Lys Gln Asp Lys Asn Gln Glu Ala Ser Ser Asp Asn Ile Asn
            340                 345                 350

Arg Ser Val Ser Val Lys Asp Asn Glu Lys Glu Leu His Asn Lys Ile
        355                 360                 365

Ala Asp Leu Glu Glu Glu Arg Gly His Leu Asp Lys Ile Asp Glu
    370                 375                 380

Leu Lys Glu Glu Leu Lys Ala Lys Glu Lys Ser Ser His His His
385                 390                 395                 400

His His Cys

<210> SEQ ID NO 15
<211> LENGTH: 1290
<212> TYPE: DNA
<213> ORGANISM: Artificial Sequence
<220> FEATURE:
<221> NAME/KEY: CDS
<222> LOCATION: (1)..(1287)
<220> FEATURE:
<223> OTHER INFORMATION: Description of Artificial Sequence: Hybrid of
      Group A Streptococci M protein and M-like protein

<400> SEQUENCE: 15 atg aac ggt gat ggt aat cct agg gaa gtt ata gaa gat ctt g

-continued

| | |
|---|---|
| tta aaa gcg aga tta gag aat gca atg gaa gtt gca gga aga gat ttt<br>Leu Lys Ala Arg Leu Glu Asn Ala Met Glu Val Ala Gly Arg Asp Phe<br>35                             40                        45 | 144 |
| aag aga gct ctc gac gat cat agt gat tta gtc gca gaa aaa caa cgt<br>Lys Arg Ala Leu Asp Asp His Ser Asp Leu Val Ala Glu Lys Gln Arg<br>50                             55                        60 | 192 |
| tta gaa gat tta gga caa aaa ttt gaa aga ctg aaa cag cgt tca gaa<br>Leu Glu Asp Leu Gly Gln Lys Phe Glu Arg Leu Lys Gln Arg Ser Glu<br>65                             70                        75                        80 | 240 |
| ctc tac ctt cag caa tac tat gat aat aaa tca aat gga tat aaa ggt<br>Leu Tyr Leu Gln Gln Tyr Tyr Asp Asn Lys Ser Asn Gly Tyr Lys Gly<br>                    85                        90                        95 | 288 |
| gac tgg tat gta caa cag tta gga tcc gat tca gta agt gga tta gag<br>Asp Trp Tyr Val Gln Gln Leu Gly Ser Asp Ser Val Ser Gly Leu Glu<br>                  100                      105                      110 | 336 |
| gtg gca gac ccc tct gat agt aag aaa ctt att gaa tta ggt ttg gct<br>Val Ala Asp Pro Ser Asp Ser Lys Lys Leu Ile Glu Leu Gly Leu Ala<br>                  115                      120                      125 | 384 |
| aaa tac ctt aat gat aaa tta ccc ttt aaa act aaa gaa gat tca gag<br>Lys Tyr Leu Asn Asp Lys Leu Pro Phe Lys Thr Lys Glu Asp Ser Glu<br>130                          135                      140 | 432 |
| att tta tca gag tta cgt gat gta tta aaa aat ctg cag gag tct cca<br>Ile Leu Ser Glu Leu Arg Asp Val Leu Lys Asn Leu Gln Glu Ser Pro<br>145                          150                      155                      160 | 480 |
| aaa agt act gag act tct gct aat gga gct gat aaa tta gct gat gca<br>Lys Ser Thr Glu Thr Ser Ala Asn Gly Ala Asp Lys Leu Ala Asp Ala<br>                  165                      170                      175 | 528 |
| tac aac aca ttg ctt act gaa cat gag aaa ctc aga gat gag tat tat<br>Tyr Asn Thr Leu Leu Thr Glu His Glu Lys Leu Arg Asp Glu Tyr Tyr<br>                  180                      185                      190 | 576 |
| aca tta att gat gct aaa gaa gaa gaa cct agg tat aaa gca ttg ggt<br>Thr Leu Ile Asp Ala Lys Glu Glu Glu Pro Arg Tyr Lys Ala Leu Gly<br>                  195                      200                      205 | 624 |
| acc ttg tta gat cag gtt aca caa tta tat act aaa cat aat agt aat<br>Thr Leu Leu Asp Gln Val Thr Gln Leu Tyr Thr Lys His Asn Ser Asn<br>210                          215                      220 | 672 |
| tac caa caa tat aat gca caa gct ggc aga ctt gac ctg aga caa aag<br>Tyr Gln Gln Tyr Asn Ala Gln Ala Gly Arg Leu Asp Leu Arg Gln Lys<br>225                          230                      235                      240 | 720 |
| gct gaa tat cta aaa ggc ctt aat gat tgg gct gag agg ctg tta caa<br>Ala Glu Tyr Leu Lys Gly Leu Asn Asp Trp Ala Glu Arg Leu Leu Gln<br>                  245                      250                      255 | 768 |
| gag tta aat ggt acc aac aat gat ggt agg tct agg gac gtt acg gaa<br>Glu Leu Asn Gly Thr Asn Asn Asp Gly Arg Ser Arg Asp Val Thr Glu<br>                  260                      265                      270 | 816 |
| gag att gca gca aac aat acc aca gta caa aat ata cgt tta cgt aac<br>Glu Ile Ala Ala Asn Asn Thr Thr Val Gln Asn Ile Arg Leu Arg Asn<br>                  275                      280                      285 | 864 |
| gaa aac aag aac tta aaa gcg aaa aac gag gac tta gaa gcg aga tta<br>Glu Asn Lys Asn Leu Lys Ala Lys Asn Glu Asp Leu Glu Ala Arg Leu<br>290                          295                      300 | 912 |
| gag aat gca atg aat gtt gca gga aga gat ttt aag aga gct gaa ttc<br>Glu Asn Ala Met Asn Val Ala Gly Arg Asp Phe Lys Arg Ala Glu Phe<br>305                          310                      315                      320 | 960 |
| gca cct ctt act cgt gct aca gca gac aat aaa gac gaa tta ata aaa<br>Ala Pro Leu Thr Arg Ala Thr Ala Asp Asn Lys Asp Glu Leu Ile Lys<br>                  325                      330                      335 | 1008 |
| aga gct aac ggt tat gag ata cag aac cat cag tta aca gtt gag aat<br>Arg Ala Asn Gly Tyr Glu Ile Gln Asn His Gln Leu Thr Val Glu Asn | 1056 |

```
                    340             345             350
aaa aaa tta aaa act gat aag gaa cag tta aca aaa gag aat gat gat      1104
Lys Lys Leu Lys Thr Asp Lys Glu Gln Leu Thr Lys Glu Asn Asp Asp
            355             360             365 tta aaa cac gtg aac ggt gat ggt aat cct agg gaa gtt ata gaa gat      1152
Leu Lys His Val Asn Gly Asp Gly Asn Pro Arg Glu Val Ile Glu Asp
        370             375             380 ctt gca gca aac aat ccc gca ata caa aat ata cgt tta cgt cac gaa      1200
Leu Ala Ala Asn Asn Pro Ala Ile Gln Asn Ile Arg Leu Arg His Glu
385             390             395             400 aac aag gac tta aaa gcg aga tta gag aat gca atg gaa gtt gca gga      1248
Asn Lys Asp Leu Lys Ala Arg Leu Glu Asn Ala Met Glu Val Ala Gly
            405             410             415 aga gat ttt aag aga gct cac cac cac cac cac cac tgc taa              1290
Arg Asp Phe Lys Arg Ala His His His His His His Cys
            420             425
```

<210> SEQ ID NO 16
<211> LENGTH: 429
<212> TYPE: PRT
<213> ORGANISM: Artificial Sequence
<220> FEATURE:
<223> OTHER INFORMATION: Description of Artificial Sequence: Hybrid of
      Group A Streptococci M protein and M-like protein

<400> SEQUENCE: 16

```
Met Asn Gly Asp Gly Asn Pro Arg Glu Val Ile Glu Asp Leu Ala Ala
  1               5                  10                  15

Asn Asn Pro Ala Ile Gln Asn Ile Arg Leu Arg His Glu Asn Lys Asp
             20                  25                  30

Leu Lys Ala Arg Leu Glu Asn Ala Met

```
                      245                 250                 255
Glu Leu Asn Gly Thr Asn Asn Asp Gly Arg Ser Arg Asp Val Thr Glu
                260                 265                 270

Glu Ile Ala Ala Asn Asn Thr Thr Val Gln Asn Ile Arg Leu Arg Asn
            275                 280                 285

Glu Asn Lys Asn Leu Lys Ala Lys Asn Glu Asp Leu Glu Ala Arg Leu
        290                 295                 300

Glu Asn Ala Met Asn Val Ala Gly Arg Asp Phe Lys Arg Ala Glu Phe
305                 310                 315                 320

Ala Pro Leu Thr Arg Ala Thr Ala Asp Asn Lys Asp Glu Leu Ile Lys
                325                 330                 335

Arg Ala Asn Gly Tyr Glu Ile Gln Asn His Gln Leu Thr Val Glu Asn
            340                 345                 350

Lys Lys Leu Lys Thr Asp Lys Glu Gln Leu Thr Lys Glu Asn Asp Asp
        355                 360                 365

Leu Lys His Val Asn Gly Asp Gly Asn Pro Arg Glu Val Ile Glu Asp
    370                 375                 380

Leu Ala Ala Asn Asn Pro Ala Ile Gln Asn Ile Arg Leu Arg His Glu
385                 390                 395                 400

Asn Lys Asp Leu Lys Ala Arg Leu Glu Asn Ala Met Glu Val Ala Gly
                405                 410                 415

Arg Asp Phe Lys Arg Ala His His His His His His Cys
            420                 425

<210> SEQ ID NO 17
<211> LENGTH: 5347
<212> TYPE: DNA
<213> ORGANISM: Artificial Sequence
<220> FEATURE:
<223> OTHER INFORMATION: Description of Artificial Sequence: Vector

<400> SEQUENCE: 17
tggcgaatgg gacgcgccct gtagcggcgc attaagcgcg gcgggtgtgg tggttacgcg    60
cagcgtgacc gctacacttg ccagcgccct agcgcccgct cctttcgctt tcttcccttc   120
ctttctcgcc acgttcgccg gctttccccg tcaagctcta atcggggggc tccctttagg   180
gttccgattt agtgctttac ggcacctcga ccccaaaaaa cttgattagg gtgatggttc   240
acgtagtggg ccatcgccct gatagacggt ttttcgccct ttgacgttgg agtccacgtt   300
ctttaatagt ggactcttgt tccaaactgg aacaacactc aaccctatct cggtctattc   360
ttttgattta agggattt tgccgatttc ggcctattgg ttaaaaaatg agctgattta   420
acaaaaattt aacgcgaatt ttaacaaaat attaacgttt acaatttcag tggcacttt   480 tcggggaaat gtgcgcggaa cccctatttg tttatttttc taaatacatt caaatatgta   540
tccgctcatg aattaattct tagaaaaact catcgagcat caaatgaaac tgcaattta   600 tcatatcagg attatcaata ccatattttt gaaaaagccg tttctgtaat gaaggagaaa   660
actcaccgag gcagttccat aggatggcaa gatcctggta tcggtctgcg attccgactc   720
gtccaacatc aatacaacct attaatttcc cctcgtcaaa ataaggtta tcaagtgaga   780 aatcaccatg agtgacgact gaatccggtg agaatggcaa aagtttatgc atttcttc    840 agacttgttc aacaggccag ccattacgct cgtcatcaaa atcactcgca tcaaccaaac   900
cgttattcat tcgtgattgc gcctgagcga gacgaaatac gcgatcgctg ttaaaaggac   960
aattacaaac aggaatcgaa tgcaaccggc gcaggaacac tgccagcgca tcaacaatat  1020
```

-continued

```
tttcacctga atcaggatat tcttctaata cctggaatgc tgttttcccg gggatcgcag    1080
tggtgagtaa ccatgcatca tcaggagtac ggataaaatg cttgatggtc ggaagaggca    1140
taaattccgt cagccagttt agtctgacca tctcatctgt aacatcattg gcaacgctac    1200 cttttgccatg tttcagaaac aactctggcg catcgggctt cccatacaat cgatagattg    1260
tcgcacctga ttgcccgaca ttatcgcgag cccatttata cccatataaa tcagcatcca    1320
tgttggaatt taatcgcggc ctagagcaag acgtttcccg ttgaatatgg ctcataacac    1380
cccttgtatt actgtttatg taagcagaca gttttattgt tcatgaccaa aatcccttaa    1440
cgtgagtttt cgttccactg agcgtcagac cccgtagaaa agatcaaagg atcttcttga    1500
gatccttttt ttctgcgcgt aatctgctgc ttgcaaacaa aaaaaccacc gctaccagcg    1560
gtggtttgtt tgccggatca agagctacca actcttttc cgaaggtaac tggcttcagc    1620
agagcgcaga taccaaatac tgtccttcta gtgtagccgt agttaggcca ccacttcaag    1680
aactctgtag caccgcctac atacctcgct ctgctaatcc tgttaccagt ggctgctgcc    1740
agtggcgata agtcgtgtct taccgggttg gactcaagac gatagttacc ggataaggcg    1800
cagcggtcgg gctgaacggg gggttcgtgc acacagccca gcttggagcg aacgacctac    1860
accgaactga gatacctaca gcgtgagcta tgagaaagcg ccacgcttcc gaagggaga    1920 aaggcggaca ggtatccggt aagcggcagg gtcggaacag gagagcgcac gagggagctt    1980
ccagggggaa acgcctggta tctttatagt cctgtcgggt ttcgccacct ctgacttgag    2040
cgtcgatttt tgtgatgctc gtcagggggg cggagcctat ggaaaaacgc cagcaacgcg    2100 gccttttac ggttcctggc cttttgctgg ccttttgctc acatgttctt tcctgcgtta    2160
tcccctgatt ctgtggataa ccgtattacc gcctttgagt gagctgatac cgctcgccgc    2220
agccgaacga ccgagcgcag cgagtcagtg agcgaggaag cggaagagcg cctgatgcgg    2280 tatttttctcc ttacgcatct gtgcggtatt tcacaccgca tatatggtgc actctcagta    2340
caatctgctc tgatgccgca tagttaagcc agtatacact ccgctatcgc tacgtgactg    2400
ggtcatggct gcgccccgac acccgccaac acccgctgac gcgccctgac gggcttgtct    2460
gctcccggca tccgcttaca gacaagctgt gaccgtctcc gggagctgca tgtgtcagag    2520
gttttcaccg tcatcaccga aacgcgcgag gcagctgcgg taaagctcat cagcgtggtc    2580
gtgaagcgat tcacagatgt ctgcctgttc atccgcgtcc agctcgttga gtttctccag    2640
aagcgttaat gtctggcttc tgataaagcg ggccatgtta agggcggttt tttcctgttt    2700
ggtcactgat gcctccgtgt aagggggatt tctgttcatg ggggtaatga taccgatgaa    2760
acgagagagg atgctcacga tacgggttac tgatgatgaa catgcccggt tactggaacg    2820
ttgtgagggt aaacaactgg cggtatggat gcggcgggac cagagaaaaa tcactcaggg    2880
tcaatgccag cgcttcgtta atacagatgt aggtgttcca cagggtagcc agcagcatcc    2940
tgcgatgcag atccggaaca taatggtgca gggcgctgac ttccgcgttt ccagactta    3000 cgaaacacgg aaaccgaaga ccattcatgt tgttgctcag gtcgcagacg ttttgcagca    3060
gcagtcgctt cacgttcgct cgcgtatcgg tgattcattc tgctaaccag taaggcaacc    3120
ccgccagcct agccgggtcc tcaacgacag gagcacgatc atgcgcaccc gtggggccgc    3180
catgccggcg ataatggcct gcttctcgcc gaaacgtttg gtggcgggac cagtgacgaa    3240
ggcttgagcg agggcgtgca agattccgaa taccgcaagc gacaggccga tcatcgtcgc    3300
gctccagcga aagcggtcct cgccgaaaat gacccagagc gctgccggca cctgtcctac    3360
gagttgcatg ataaagaaga cagtcataag tgcggcgacg atagtcatgc cccgcgccca    3420
```

```
ccggaaggag ctgactgggt tgaaggctct caagggcatc ggtcgagatc cggtgcctc      3480
atgagtgagc taacttacat taattgcgtt gcgctcactg cccgctttcc agtcgggaaa      3540
cctgtcgtgc cagctgcatt aatgaatcgg ccaacgcgcg gggagaggcg gtttgcgtat      3600
tgggcgccag ggtggttttt cttttcacca gtgagacggg caacagctga ttgcccttca      3660
ccgcctggcc ctgagagagt tgcagcaagc ggtccacgct ggtttgcccc agcaggcgaa      3720
aatcctgttt gatggtggtt aacggcggga tataacatga gctgtcttcg gtatcgtcgt      3780
atcccactac cgagatatcc gcaccaacgc gcagcccgga ctcggtaatg cgcgcattg       3840
cgcccagcgc catctgatcg ttggcaacca gcatcgcagt gggaacgatg ccctcattca      3900
gcatttgcat ggtttgttga aaaccggaca tggcactcca gtcgccttcc cgttccgcta      3960
tcggctgaat ttgattgcga gtgagatatt tatgccagcc agccagacgc agacgcgccg      4020
agacagaact taatgggccc gctaacagcg cgatttgctg gtgacccaat gcgaccagat      4080
gctccacgcc cagtcgcgta ccgtcttcat gggagaaaat aatactgttg atgggtgtct      4140
ggtcagagac atcaagaaat aacgccggaa cattagtgca ggcagcttcc acagcaatgg      4200
catcctggtc atccagcgga tagttaatga tcagcccact gacgcgttgc gcgagaagat      4260
tgtgcaccgc cgctttacag gcttcgacgc cgcttcgttc taccatcgac accaccacgc      4320
tggcacccag ttgatcggcg cgagatttaa tcgccgcgac aatttgcgac ggcgcgtgca      4380
gggccagact ggaggtggca acgccaatca gcaacgactg tttgcccgcc agttgttgtg      4440
ccacgcggtt gggaatgtaa ttcagctccg ccatcgccgc ttccactttt tcccgcgttt      4500
tcgcagaaac gtggctggcc tggttcacca cgcgggaaac ggtctgataa gagacaccgg      4560
catactctgc gacatcgtat aacgttactg gtttcacatt caccaccctg aattgactct      4620
cttccgggcg ctatcatgcc ataccgcgaa aggttttgcg ccattcgatg gtgtccggga      4680
tctcgacgct ctcccttatg cgactcctgc attaggaagc agcccagtag taggttgagg      4740
ccgttgagca ccgccgccgc aaggaatggt gcatgcaagg agatggcgcc caacagtccc      4800
ccggccacgg ggcctgccac catacccacg ccgaaacaag cgctcatgag cccgaagtgg      4860
cgagcccgat cttccccatc ggtgatgtcg gcgatatagg cgccagcaac cgcacctgtg      4920
gcgccggtga tgccggccac gatgcgtccg gcgtagagga tcgagatcta atcataaaaa      4980
atttatttgc tttgtgagcg gataacaatt ataatagatt caattgtgag cggataacaa      5040
ttataataga ttcaattcta aatttacaag aatttcacac agaattcatt aaagaggaga      5100
aattacatat ggctagcatg actggtggac agcaaatggg tcgcggatcc gaattcgagc      5160
tccgtcgaca gcttcggcc cgcactcgag caccaccacc accaccactg agatccggct      5220
gctaacaaag cccgaaagga agctgagttg gctgctgcca ccgctgagca ataactagca      5280
taaccccttg ggcctctaa acgggtcttg aggggttttt tgctgaaagg aggaactata      5340
tccggat                                                               5347
```

<210> SEQ ID NO 18
<211> LENGTH: 8
<212> TYPE: PRT
<213> ORGANISM: Artificial Sequence
<220> FEATURE:
<223> OTHER INFORMATION: Carboxy terminal tag sequence

<400> SEQUENCE: 18

Asp Tyr Lys Asp Asp Asp Asp Lys
 1               5

```
<210> SEQ ID NO 19
<211> LENGTH: 8
<212> TYPE: PRT
<213> ORGANISM: Artificial Sequence
<220> FEATURE:
<223> OTHER INFORMATION: Carboxy terminal tag sequence

<400> SEQUENCE: 19

Asp Leu Tyr Asp Asp Asp Asp Lys
1               5
```